United States Patent
Dalton et al.

(10) Patent No.: US 7,772,433 B2
(45) Date of Patent: Aug. 10, 2010

(54) SARMS AND METHOD OF USE THEREOF

(75) Inventors: James T. Dalton, Upper Arlington, OH (US); Duane D. Miller, Germantown, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 550 days.

(21) Appl. No.: 11/785,250

(22) Filed: Apr. 16, 2007

(65) Prior Publication Data

US 2008/0057068 A1  Mar. 6, 2008

Related U.S. Application Data

(60) Continuation-in-part of application No. 10/861,905, filed on Jun. 7, 2004, which is a continuation-in-part of application No. 10/371,155, filed on Feb. 24, 2003, application No. 11/785,250, which is a continuation-in-part of application No. 11/723,957, filed on Mar. 22, 2007, now abandoned, which is a division of application No. 10/683,125, filed on Oct. 14, 2003, now Pat. No. 7,214,693, application No. 11/785,250, which is a continuation-in-part of application No. 11/510,844, filed on Aug. 28, 2006.

(60) Provisional application No. 60/453,736, filed on Feb. 28, 2002, provisional application No. 60/423,381, filed on Nov. 4, 2002, provisional application No. 60/418,173, filed on Oct. 15, 2002, provisional application No. 60/712,390, filed on Aug. 31, 2005, provisional application No. 60/839,665, filed on Aug. 24, 2006.

(51) Int. Cl.
*C07C 233/05* (2006.01)
*A61K 31/165* (2006.01)

(52) U.S. Cl. ................. 564/175; 558/414; 514/522; 514/617

(58) Field of Classification Search ............... 564/175; 558/414; 514/522, 617
See application file for complete search history.

(56) References Cited

U.S. PATENT DOCUMENTS

| | | | |
|---|---|---|---|
| 3,875,229 A | 4/1975 | Gold | |
| 4,139,638 A | 2/1979 | Neri et al. | |
| 4,191,775 A | 3/1980 | Glen | |
| 4,239,776 A | 12/1980 | Glen et al. | |
| 4,282,218 A | 8/1981 | Glen et al. | |
| 4,386,080 A | 5/1983 | Crossley et al. | |
| 4,411,890 A | 10/1983 | Momany et al. | |
| 4,465,507 A | 8/1984 | Konno et al. | |
| 4,636,505 A | 1/1987 | Tucker | |
| 4,880,839 A | 11/1989 | Tucker | |
| 5,162,504 A | 11/1992 | Horoszewicz | |
| 5,179,080 A | 1/1993 | Rothkopf et al. | |
| 5,609,849 A | 3/1997 | Kung | |
| 5,612,359 A | 3/1997 | Murugesan et al. | |
| 5,656,651 A | 8/1997 | Sovak et al. | |
| 6,019,957 A | 2/2000 | Miller et al. | |
| 6,043,265 A | 3/2000 | Murugesan et al. | |
| 6,071,957 A | 6/2000 | Miller et al. | |
| 6,160,011 A | 12/2000 | Miller et al. | |
| 6,482,861 B2 | 11/2002 | Miller et al. | |
| 6,492,554 B2 | 12/2002 | Dalton et al. | |
| 6,548,529 B1 | 4/2003 | Robl et al. | |
| 6,569,896 B2 | 5/2003 | Dalton et al. | |
| 6,777,427 B2 | 8/2004 | Miyakawa et al. | |
| 6,838,484 B2 | 1/2005 | Steiner et al. | |
| 6,960,474 B2 | 11/2005 | Salvati et al. | |
| 7,026,500 B2 | 4/2006 | Dalton et al. | |
| 2001/0012839 A1 | 8/2001 | Miller et al. | |
| 2002/0173445 A1 | 11/2002 | Salvati et al. | |
| 2004/0214790 A1 | 10/2004 | Borgens et al. | |

FOREIGN PATENT DOCUMENTS

| | | |
|---|---|---|
| EP | 0 040 932 | 12/1981 |
| EP | 0 100 172 | 2/1984 |
| EP | 000 2892 | 2/1985 |
| EP | 0 253 503 | 1/1988 |
| EP | 1221439 | 7/2002 |
| GB | 1360001 | 3/1970 |
| JP | 52-128329 | 10/1977 |
| JP | 54-63047 | 12/1980 |
| WO | WO 89/07110 | 8/1989 |
| WO | WO 89/07111 | 8/1989 |
| WO | WO 93/04081 | 3/1993 |
| WO | WO 95/19770 | 7/1995 |
| WO | WO 98 05962 | 2/1998 |

(Continued)

OTHER PUBLICATIONS

U.S. Appl. No. 09/644,970, filed Aug. 2, 2000, Dalton et al.

(Continued)

*Primary Examiner*—Shailendra Kumar
(74) *Attorney, Agent, or Firm*—Mark S. Cohen; Pearl Cohen Zedek Latzer, LLP

(57) ABSTRACT

This invention provides SARM compounds and uses thereof in treating a variety of diseases or conditions in a subject, including, inter-alia, muscle wasting diseases and/or disorders, bone-related diseases and/or disorders, diabetes, cardiovascular disease, renal disease and others.

7 Claims, 15 Drawing Sheets

FOREIGN PATENT DOCUMENTS

| WO | WO 98/53826 | 12/1998 |
|----|----|----|
| WO | WO 98/55153 | 12/1998 |
| WO | WO/01/27086 | 4/2001 |
| WO | WO 01 27622 | 4/2001 |
| WO | WO 01 28990 | 4/2001 |
| WO | WO 01 34563 | 5/2001 |
| WO | WO 0168603 | 9/2001 |
| WO | WO 02 00617 | 1/2002 |
| WO | WO 02/16310 | 2/2002 |
| WO | WO/02/22585 | 3/2002 |
| WO | WO/03/077919 | 9/2003 |

OTHER PUBLICATIONS

U.S. Appl. No. 09/935,044, filed Aug. 23, 2001, Dalton et al.
U.S. Appl. No. 09/935,045, filed Aug. 23, 2001, Dalton et al.
U.S. Appl. No. 10/298,229, filed Nov. 28, 2002, Miller et al.
U.S. Appl. No. 10/270,232, filed Oct. 15, 2002, Dalton et al.
U.S. Appl. No. 10/277,108, filed Oct. 23, 2002, Dalton et al.
U.S. Appl. No. 10/270,233, filed Oct. 15, 2002, Dalton et al.
U.S. Appl. No. 10/270,732, filed Oct. 15, 2002, Dalton et al.
U.S. Appl. No. 10/310,150, filed Dec. 5, 2002, Steiner et al.
Howard Tucker and Glynne J. Chesterson, J. Med Chem, 1988, 31, pp. 885-887, "Resolution of the Nonsteroidal Antiandrogen -4'-Cyano-3-[(4-fluorophenyl)-sulfonyl]-2-hydroxy-2-methyl-3'-(trifluoromethyl)-propionanilide and the Determination of the Absolute Configuration of the Active Enantiomer".
D. McKillop, et al., "Enantioselective metabolism and pharmacokinetics of Casodex in the male rat", Xenobiotica, 1995, vol. 25, No. 6, 623-634.
Leonid Kirkovsky, et al., "[$^{125}$I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.
David T. Baird and Anna F. Glasier, "Hormonal Contraception—Drug Therapy", The New England Journal of Medicine, May 27, 1993, pp. 1543-1549.
F.C. W. Wu, "Male Contraception: Current Status and Future Prospects", Clinical Endocrinology, (1988), 29, pp. 443-465.
Carl Djerassi and S.P. Leibo, "A new look at male contraception", Nature, vol. 370, pp. 11-12.
World Health Organisation Task Force on Methods for the Regulation of Male Fertility, "Contraceptive efficacy of testosterone-induced azoospermia in normal men", The Lancet, vol. 336, Oct. 20, 1990, pp. 955-959 and 1517-1518.
C. G. Francisco, et al., "Long-acting contraceptive agents: testosterone esters of unsaturated acids", Steroids, Jan. 1990, vol. 55, Butterworths.
John M. Hoberman and Charles E. Yesalis, "The History of Synthetic Testosterone", Scientific American, Feb. 1995, pp. 76-81.
Leonid Kirkovsky, et al., "Approaches to Irreversible non-steroidal chiral antiandrogens", Department of Pharmaceutical Sciences, University of Tennessee, 47th Southeast/51st Southwest Joint Regional Meeting of the American Chemical Society, Memphis, TN, Nov. 29-Dec. 1, 1995.
David J. Handelsman, "Bridging the gender gap in contraception: another hurdle cleared" The Medical Journal of Australia, vol. 154, Feb. 18, 1996, pp. 230-233.
Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4-(trifluoromethyl)-2II-pyrano[3,2-g]quinolin-2-one. Bioorg. Med. Chem. Lett., 9: 1003, 1999.
Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009, 1999.
Higuchi RI, Edwards JP, Caferro TR, Ringgenberg JD, Kong JW, Hamann LG, Arienti KL, Marschke KB, Davis RL, Farmer LJ, and Jones TK. 4-Alkyl- and 3,4-diakyl-1,2,3,4-tetrahydro-8-pyridono[5,6-g]quinolines: potent, nonsteroidal androgen receptor agonists. Bioorg. Med. Chem. Lett., 9:1335,1999.
Hamann LG, Mani NS, Davis RL, Wang XN, Marschke KB, and Jones TK. Discovery of a potent, orally active nonsteroidal androgen receptor agonists: 4-ethyl-1,2,3,4-tetrahydro-6-(trifluoromethyl)-8-pyridono[5,6-g]-quinoline (LG121071). J. Med. Chem., 42: 210, 1999.
Rosen J, Day A, Jones TK, Jones ET, Nadzan AM, and Stein RB. Intracellular receptors and signal transducers and activators of transcription superfamilies: novel targets for small-molecule drug discovery. J. Med. Chem., 38: 4855, 1995.
Dalton JT, Mukherjee A, Zhu Z, Kirkovsky L, and Miller DD. Discovery of Nonsteroidal Androgens. Biochem. Biophys. Res. Commun.,244(1):1-4, 1998.
Edwards JP, West SJ, Pooley CLF, Marschke KB, Farmer LJ, and Jones TK. New nonsteroidal androgen receptor modulators based on 4-(trifluoromethyl)-2-(III)-Pyrololidino[3,2-g]quinolone. Bioorg. Med. Chem. Lett., 8: 745, 1998.
Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.
Berger et al., "Concepts and limitations in the application of radiolabeled antiandrogens, estrogens, or androgens as isotropic scanning agents for the prostate", Invest. Urol. (1975), 1391, 10-16.
Wahner, et al (1984) "Assesment of Bone Mineral Part I" J Nucl. Medicine, 1134-1141.
Wahner, et al (1985) "Bone Mineral Density of the Radius" J. Nucl Medicine 26 13-39.
Faulkner KG, et al (1991) "Noninvasive measurements of bone mass, structure, and strength: current methods and experimental techniques." Am J Rosentgenology 157:1229-1237.
Hanada, K., et al (2003) "Bone anabolic effects of S-40503, a novel nonsteroidal selective androgen receptor modulator (SARM), in rat models of osteoperosis." Biol. Pharm. Bull. 26:1563-1569.
Kalu, DN, (1991) "The ovariectomized rat model of postmenopausal bone loss. Bone Miner." 15 175-91.
Langer (1990) "New methods of drug delivery," Science 249:1527-1533.
Negro-Vilar, A, (1999) "Selective androgen receptor modulators (SARMs): a novel approach to androgen therapy for the new illennium." J. Clin. Endocrin Metabol. 84: 3459-3462.
Koski GK, Kariko K, Xu S, Weissman D, Cohen PA, Czerniecki BJ. Cutting edge: innate immune system discriminates between RNA containing bacterial versus eukaryotic structural features that prime for high-level 11-12 secretion by dendritic cells. J Immunol. Apr. 1, 2004:172(7):3989-93.
Heil F, Hemmi H, Hochrein H, Ampenberger F, Kirschning C, Akiru S, Lipford G, Wagner H, Bauer S. Species-specific recognition of single-stranded RNA via toll-like receptor 7 and 8. Science. Mar. 5, 2004:303(5663):1526-9.
Diebold SS, Kaisho T, Hemmi H, Akiru S, Reis e Sousa C. Innate antiviral responses by means of TLR7-mediated recognition of single-stranded RNA. Science. Mar. 5, 2004:303(5663):1529-31.
Campfield et al., 1995, "Recombinant mouse OB protein: evidence for a peripheral signal linking adiposity and central neural networks" *Science* 269:546-549.
Considine et al., 1995, "Evidence against either a premature stop endon or the absence of obese gene mRNA in human obesity," J. Clin. Invest. 95:2986-2988.
Grundy, 1990, *Disease-a-Month* 36:645-696.
Halaas et al., 1995, "Weight-Reducing effects of the plasma protein encoded by the obese gene." *Science* 269:543-546.
Hamilton et al., 1995, <<Increased obese mRNA expression in omental fat cells from massively obese humans. Nature Med. 1:953.
Lonnquist et al., 1995, Nature Med. 1:950.
Matsumoto, 1994, "Hormonal therapy of male hypogonadism" Endocrinol. Met. Clin. N. Am. 23:857-75.
Pelleymounter et al., 1995, "Effects of the obese gene product on body weight regulation in ob/ob mice." *Science* 269:540-543.

Singh et al., 2003, "Androgens stimulate myogenic differentiation and inhibit adipogenesis in C3H I0TI/2 pluripotent cells through an androgen receptor-mediated pathway." *Endocringology,* 144(11):5081-8.

Sefton, 1987, "Implantable pumps." CRC Cric. Ref. Biomed. Eng. 14:201.

Narayanan, et al "Steroidal Androgens and Nonsteroidal, Tissue Selective Androgen Receptor Modulators (SARM) Regulate Androgen Receptor Function Through Distinct Genomic and Non-Genomic Signaling Pathways." The Endocrine Society—Programs and Abstracts—89th Annual Meeting Paper P1-595.

Yepuru, et al "AN Androgen Receptor-b Specific Selective Estrogen Receptor Modulator (SERM) Inhibits the Growth of the Prostate Cancer Cells and Stromal-Epithilial Tumor Xenograft" The Endocrine Society Programs and Abstracts—89th Annual Meeting—Paper OR6-3.

Dalton, et al "Therapeutic Promise of Selective Androgen Receptor Modulators (SARSs): Preclinical and Clinical Proof-of-Concept Studies."The Endocrine Society—Programs and Abstracts 89th Annual Meeting—Paper S41-2.

Edwards, J. P. et. al., Bio. Med. Chem. Let., 9, 1003-1008 (1999).

Hamann, L. G. et. al., J. Med. Chem., 42, 210-212 (1999).

I. Synthetic Scheme for (S)-[[III]] II Compound:

II. Synthetic Scheme for (R)- [[III]] II Compound:

III. Synthetic Scheme for (S)- [[III]] II (oxirane intermediate) Compound:

IV. Synthetic Scheme for (R)- [[III]] II (oxirane intermediate) Compound:

V. Synthetic Scheme for (S)- [[III]] II involving B-ring addition prior to A-ring addition:

VI. Synthetic Scheme of (R)- [[III]] II Involving B-ring Addition Prior to A-ring Addition:

VII. Synthetic Scheme of (S)- [[III]] II Using Chiral Intermediate and Involving B-ring Addition prior to A-ring Addition:

VIII. Synthetic Scheme for (R)- [[III]] II Using Chiral Intermediate and Involving B-ring Addition Prior to A-ring Addition:

IX. Synthetic Scheme for Racemic Compound [[III]] II Involving Oxazolidinedione Intermediate:
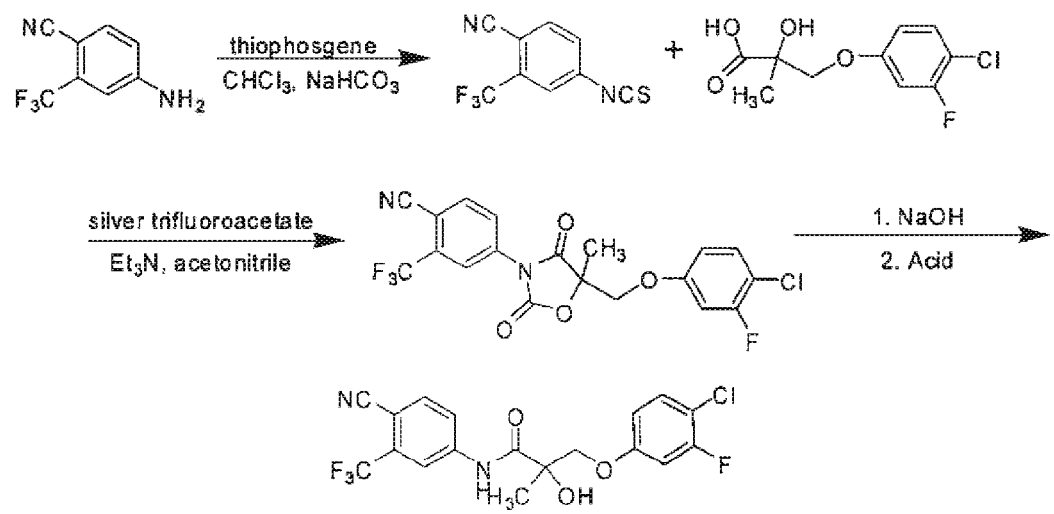
Figure II X. Racemic Synthetic Scheme for Compound [[III]] II:

XI. Large-scale Synthetic Scheme for (S)- [[III]] II:

XII. Large-Scale Synthetic Scheme for (S)- [[III]] II:

SARMS AND METHOD OF USE THEREOF

CROSS REFERENCE TO RELATED APPLICATIONS

This application is a Continuation-In-Part Application of U.S. patent application Ser. No. 10/861,905 filed Jun. 7, 2004, which is a Continuation-In-Part Application of U.S. patent application Ser. No. 10/371,155 filed Feb. 24, 2003, which claims the benefit of U.S. Provisional Patent Application Ser. No. 60/453,736 filed Feb. 28, 2002 and U.S. Provisional Patent Application Ser. No. 60/423,381, filed Nov. 4, 2002; and this Application is a Continuation-In-Part Application of U.S. patent application Ser. No. 11/723,957, filed on Mar. 22, 2007, now abandoned which is a Divisional Application of U.S. patent application Ser. No. 10/683,125, filed on Oct. 14, 2003, now U.S. Pat. No. 7,214,693 which claims the benefit of U.S. Provisional Patent Application Ser. No. 60/418,173, filed Oct. 15, 2002; and this Application is a Continuation-In-Part Application of U.S. patent application Ser. No. 11/510,844, filed on Aug. 28, 2006, which claims the benefit of U.S. Provisional Patent Application No. 60/712,390, filed Aug. 31, 2005; and this Application claims the benefit of U.S. Provisional Application Ser. No. 60/839,665, filed Aug. 24, 2006, all of which are hereby incorporated by reference in their entirety.

GOVERNMENT INTEREST STATEMENT

This invention was made in whole or in part with government support under grant number R01 DK598006, awarded by the National Institute of Health; under grant number R29 CA068096 awarded by the National Cancer Institute, National Institute of Health; under grant number R15 HD35329, awarded by the National Institute of Child Health and Human Development, National Institute of Health and under grant number R01 DK59800, awarded by the National Institute of Health. The government may have certain rights in the invention.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857-75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208-18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone (MENT): The Optimal Androgen For Male Contraception," Ann. Med., 25:199-205 (1993) ("Sundaram"). Because the AR is involved in male sexual development and function, the AR is a likely target for effecting male contraception or other forms of hormone replacement therapy.

Worldwide population growth and social awareness of family planning have stimulated a great deal of research in contraception. Contraception is a difficult subject under any circumstance. It is fraught with cultural and social stigma, religious implications, and, most certainly, significant health concerns. This situation is only exacerbated when the subject focuses on male contraception. Despite the availability of suitable contraceptive devices, historically, society has looked to women to be responsible for contraceptive decisions and their consequences. Although concern over sexually transmitted diseases has made men more aware of the need to develop safe and responsible sexual habits, women still often bear the brunt of contraceptive choice. Women have a number of choices, from temporary mechanical devices such as sponges and diaphragms to temporary chemical devices such as spermicides. Women also have at their disposal more permanent options, such as physical devices including IUDs and cervical caps as well as more permanent chemical treatments such as birth control pills and subcutaneous implants. However, to date, the only options available for men include the use of condoms and vasectomy. Condom use, however is not favored by many men because of the reduced sexual sensitivity, the interruption in sexual spontaneity, and the significant possibility of pregnancy caused by breakage or misuse. Vasectomies are also not favored. If more convenient methods of birth control were available to men, particularly long-term methods which require no preparative activity immediately prior to a sexual act, such methods could significantly increase the likelihood that men would take more responsibility for contraception.

Administration of the male sex steroids (e.g., testosterone and its derivatives) has shown particular promise in this regard due to the combined gonadotropin-suppressing and androgen-substituting properties of these compounds (Steinberger et al., "Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320-28 (1977)). Chronic administration of high doses of testosterone completely abolishes sperm production (azoospermia) or reduces it to a very low level (oligospermia). The degree of spermatogenic suppression necessary to produce infertility is not precisely known. However, a recent report by the World Health Organization showed that weekly intramuscular injections of testosterone enanthate result in azoospermia or severe oligospermia (i.e., less than 3 million sperm per ml) and infertility in 98% of men receiving therapy (World Health Organization Task Force on Methods And Regulation of Male Fertility, "Contraceptive Efficacy of Testosterone-Induced Azoospermia and Oligospermia in Normal Men," Fertility and Sterility 65:821-29 (1996)).

A variety of testosterone esters have been developed which are more slowly absorbed after intramuscular injection and thus result in greater androgenic effect. Testosterone enanthate is the most widely used of these esters. While testosterone enanthate has been valuable in terms of establishing the feasibility of hormonal agents for male contraception, it has several drawbacks, including the need for weekly injections and the presence of supraphysiologic peak levels of testosterone immediately following intramuscular injection (Wu, "Effects of Testosterone Enanthate in Normal Men: Experience From a Multicenter Contraceptive Efficacy Study," Fertility and Sterility 65:626-36 (1996)).

Bone mineral density (BMD) decreases with age in both males and females. Decreased amounts of bone mineral content (BMC) and BMD correlate with decreased bone strength and predispose patients to fracture.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake. However, osteoporosis also occurs frequently in males. It is well established that the bone mineral density of males decrease with age. Decreased amounts of bone mineral content and density correlates with decreased bone strength, and predisposes to fracture. The molecular mechanisms underlying the pleiotropic effects of sex-hormones in non-reproductive tissues are only beginning to be understood, but it is clear that physiologic concentrations of androgens and estrogens play an important role in maintaining bone homeostasis throughout the life-cycle. Consequently, when androgen or estrogen deprivation occurs there is a resultant increase in the rate of bone remodeling that tilts the balance of resorption and formation to the favor of resorption that contributes to the overall loss of bone mass. In males, the natural decline in sex-hormones at maturity (direct decline in androgens as well as lower levels of estrogens derived from peripheral aromatization of androgens) is associated with the frailty of bones. This effect is also observed in males who have been castrated.

Muscle wasting refers to the progressive loss of muscle mass and/or to the progressive weakening and degeneration of muscles, including the skeletal or voluntary muscles, which control movement, cardiac muscles, which control the heart (cardiomyopathics), and smooth muscles. Chronic muscle wasting is a chronic condition (i.e. persisting over a long period of time) characterized by progressive loss of muscle mass, weakening and degeneration of muscle.

The loss of muscle mass that occurs during muscle wasting can be characterized by muscle protein degradation by catabolism. Protein catabolism occurs because of an unusually high rate of protein degradation, an unusually low rate of protein synthesis, or a combination of both. Muscle protein catabolism, whether caused by a high degree of protein degradation or a low degree of protein synthesis, leads to a decrease in muscle mass and to muscle wasting.

Muscle wasting is associated with chronic, neurological, genetic or infectious pathologies, diseases, illnesses or conditions. These include Muscular Dystrophies such as Duchenne Muscular Dystrophy and Myotonic Dystrophy; Muscle Atrophies such as Post-Polio Muscle Atrophy (PPMA); Cachexias such as Cardiac Cachexia, AIDS Cachexia and Cancer Cachexia, malnutrition, Leprosy, Diabetes, Renal Disease, Chronic Obstructive Pulmonary Disease (COPD), Cancer, end stage Renal failure, Sarcopenia, Emphysema, Osteomalacia, HIV Infection, AIDS, and Cardiomyopathy.

In addition, other circumstances and conditions are linked to and can cause muscle wasting. These include chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, disuse deconditioning that occurs when a limb is immobilized, long term hospitalization due to illness or injury, and alcoholism.

An intact androgen receptor (AR) signaling pathway is crucial for appropriate development of skeletal muscles. Furthermore, an intact AR-signaling pathway increases lean muscle mass, muscle strength and muscle protein synthesis.

Muscle wasting, if left unabated, can have dire health consequences. For example, the changes that occur during muscle wasting can lead to a weakened physical state that is detrimental to an individual's health, resulting in increased susceptibility to infraction and poor performance status. In addition, muscle wasting is a strong predictor of morbidity and mortality in patients suffering from cachexia and AIDS.

New innovative approaches are urgently needed at both the basic science and clinical levels to develop compounds which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; e) decreasing the incidence of, halting or causing a regression of prostate cancer; f) oral androgen replacement and/or other clinical therapeutic and/or diagnostic areas.

A wide variety of diseases and/or conditions are affected by hypogonadism, and catabolic effects, including kidney disease, central nervous system injuries, burns and chronic wounds.

In the United States (US), there is a rising incidence and prevalence of kidney failure. The number of patients enrolled in end-stage renal disease (ESRD) Medicare-funded programs has increased from approximately 10,000 beneficiaries in 1973 to 86,354 in 1983, and to 431,284 as of Dec. 31, 2002. In 2002 alone, 100,359 patients entered the US ESRD program. Chronic kidney disease (CKD) is a precursor to ESRD and occurs when the kidneys are not able to adequately remove wastes from the body. CKD is a slowly progressing disease, in which diabetes, hypertension and anemia may be co-morbid conditions.

CKD is diagnosed using a staging system that demonstrates the amount of kidney function available (stage 1=normal kidney function) and patients often do not present symptoms in the early stages. Stage 5 of CKD is ESRD, which is a complete or near complete failure of the kidneys and usually occurs when kidney function is less than 10% of baseline.

Accompanying symptoms associated with ESRD include hypogonadism, involuntary weight loss, fatigue and others.

Burns result in a testosterone reduction, nitrogen level reduction and a reduction in bone mineral density (BMD), which may persist even as long one year following the injury and is associated with impaired wound healing, increased infection risks, erosion of lean body mass, hampered rehabilitation, and delayed reintegration of burn survivors into society. Catabolic effects initiated as a result of the burn lead to significant involuntary weight loss, further compounding the problem.

Spinal cord injuries may result in the alteration central neurotransmitter secretion or production, which in turn may cause a hypothalamus-pituitary-adrenal axis dysfunction, leading to decreases in testosterone and other hormone levels. SCI or other acute illness or trauma characteristically includes heightened catabolism in conjunction with the lowered anabolic activity resulting in a condition that is prone to loss of lean body tissue. As long as the catabolic process goes uninterrupted, disturbed nutrient utilization will continue. The effects of the loss of lean body mass include the development of wounds and impaired healing mechanisms. Because of poor nutrition and protein combined with immobilization, patients with spinal cord injury are at high risk for bed sores.

Chronic wounds may be caused by any number of conditions, including diabetes, circulatory problems, immobilization and others. Compounding the problem, for example in diabetes, is the presence of neuropathy, which increases the risk of foot ulceration.

While there are many treatments and therapies for these conditions, none are ideal. Since the androgen receptor (AR) signaling pathway has been shown to increase lean muscle mass, muscle strength and muscle protein synthesis, and since hypogonadism accompanies these conditions, molecules targeting the AR signaling pathway may be useful in treating these diseases and/or conditions.

SUMMARY OF THE INVENTION

In one embodiment, the present invention provides, a compound represented by the structure of formula (I):

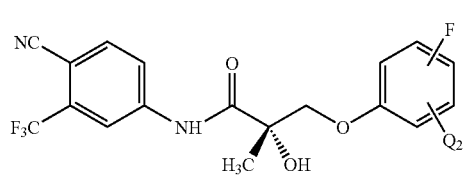

(I)

wherein $Q_2$ is alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; and R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

or its isomer, pharmaceutically acceptable salt, pharmaceutical product, N-oxide, hydrate or any combination thereof.

In one embodiment, the present invention provides, a compound represented by the structure of formula II:

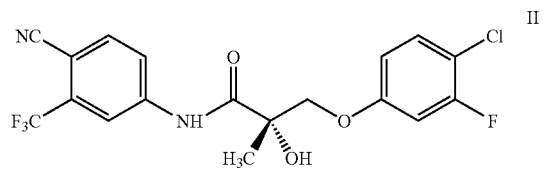

II or its isomer, pharmaceutically acceptable salt, pharmaceutical product, N-oxide, hydrate or any combination thereof.

In one embodiment, the present invention provides, a compound represented by the structure of formula III:

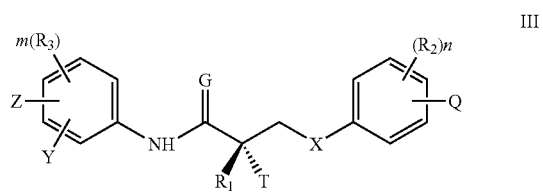

III wherein X is a bond, O, $CH_2$, NH, Se, PR, NO or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl or OH;

$R_1$ is $CH_3$, $CH_2F$, $CHF_2$, $CF_3$, $CH_2CH_3$, or $CF_2CF_3$;

$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, SR;

$R_3$ is H, F, Cl, Br, I, CN, $NO_2$, COR, COOH, CONHR, $CF_3$, $Sn(R)_3$, or $R_3$ together with the benzene ring to which it is attached forms a fused ring system represented by the structure:

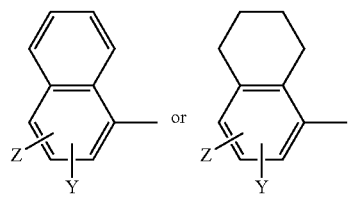

Z is $NO_2$, CN, Cl, F, Br, I, H, COR, COOH, or CONHR;

Y is $CF_3$, alkoxy, alkyl, hydroxyalkyl, alkylaldehyde, formyl, H, F, Br, Cl, I, CN, or $Sn(R)_3$;

Q is H, alkyl, halogen, $CF_3$, CN $CR_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OH, OR, COR, OCOR, $OSO_2R$, $SO_2R$, SR; or Q together with the benzene ring to which it is attached is a fused ring system represented by structure A, B or C:

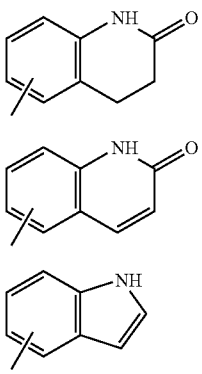

n is an integer of 1-4; and m is an integer of 1-3;

or its isomer, pharmaceutically acceptable salt, pharmaceutical product, N-oxide, hydrate or any combination thereof.

In one embodiment, Z, Y and Q are not H. In one embodiment, Z, Y, Q and $R_2$ are not H, if $R_3$ is H. In one embodiment, Z, Y, Q and $R_3$ are not H, if $R_2$ is H.

In one embodiment, Z is $NO_2$, CN, Cl, F, Br, I, COR, COOH, or CONHR; Y is $CF_3$, alkoxy, alkyl, hydroxyalkyl, alkylaldehyde, formyl, F, Br, Cl, I, CN, or $Sn(R)_3$; and $R_3$ is H, F, Cl, Br, I, CN, $NO_2$, COR, COOH, CONHR, $CF_3$, $Sn(R)_3$. According to this aspect, and in one embodiment, neither $R_2$ nor Q is H.

In one embodiment, the present invention provides a compound characterized by the structure of formula IV:

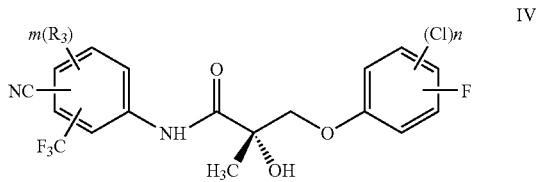

In one embodiment, the present invention provides a composition comprising the compound of formula (I), (II), (III) or (IV) and/or its derivative, isomer, pharmaceutically acceptable salt, pharmaceutical product, crystal, hydrate, N-oxide or any combination thereof.

In one embodiment, the compounds of this invention are selective androgen receptor modulators.

In one embodiment, the compositions of this invention further comprise a therapeutic agent, which in one embodiment is an anti-cancer agent, an immunomodulating agent, an agent treating diabetes, an agent treating the nervous system, an agent treating the cardiovascular system, an agent treating the gastrointestinal system, an agent treating a dermatological disease, or condition, an anti-infective agent, an agent treating the liver, an agent treating the kidney, an agent treating a metabolic disease, an agent treating a wasting disease, a gene therapy agent, an agent treating the endocrine system, a vitamin, a stomatognathic agent, a urogenital agent, behavior-modulating agent, an agent treating the respiratory system, an agent treating the hemic system, an agent treating an ophthalmic disease, or any combination thereof.

In one embodiment, the therapeutic agent is an anti-androgen, an antiestrogen, a monoclonal antibody, a chemotherapeutic agent, an immunosuppressive or anti-inflammatory agent, an immunostimulatory agent, a sulfonylurea, meglitnide, insulin, biguanide, thiazolidinedione, or alpha-glucosidase inhibitor, an adrenomimetic agent, adrenoceptor antagonist, cholinomimetic agent, a muscarinic blocker, a ganglionic blocker, an anesthetic agent, an analgesic agent, an agent treating neuromuscular transmission, a nervous system stimulant, a sedative agent, neurodegenerative disorder medication, antiepileptic agent, antipsychotic agent, anti-addiction agent, an anti-arrhythmic agent, an anti-anginal agent, a vasocative agent, a calcium channel blocker, an antihypertensive agent, a diuretic agent, an anticoagulant or fibrinolytic agent, a hypocholesterolemic agent, an opioid, 5-HT3 receptor antagonist, adsorbent agent, bulking agent, a stool softening or laxative agent, cathartic agent, an antiemetic agent, an emetic agent, an antacid agent, an H2-receptor antagonist, a proton pump inhibitor, a 5-aminosalicylate agent, a prostaglandin, a glucocorticosteroid, a retinoid, photochemotherapeutic agent, a photodynamic agent, aminolevulinic acid, dapsone, pyrethrin, pyrethroid, thalidomide, an antimalarial agent, an antimicrobial agent, an antifungal agent, an antiviral agent, a sulfonamide, a trimethoprim agent, a quinolone agent, an oxazolidinone agent, an antiseptic agent, a beta-lactam agent, an aminoglycoside agent, a tetracycline agent, a chloramphenicol agent, a macrolide agent, a lincosamide agent, a bacitracin agent, a glycopeptide agent, a polymyxin agent, an antiprotozoal agent, an antithelmintic agent, a cortisone, a colchicine, a methotrexate, a ursodeoxycholic acid, a penicillamine, a vitamin, glucosidase alpha, sodium bicarbonate, bisphosphonate, biotin, allopurinol, levodopa, diazepam, phenobarbital, haloperidol, folic acid, haptoglobin, carnitine, a steroid, cannabinoid metoclopramid, cisapride, medroxyprogesterone acetate, megestrol acetate, cyproheptadine, hydrazine sulfate, pentoxifylline, thalidomide, anticytokine antibodies, cytokine inhibitors, eicosapentaenoic acid, indomethacin, ibuprofen, melatonin, insulin, growth hormone, clenbuterol, pancreas extract, cabergoline, bromocriptine, thyroxine, gonadotropin, glucocorticoid, glucocorticoid analogue, corticotrophin, metyrapone, aminoglutethimide, mitotane, ketoconazole, mifepristone, dexamethasone somatostatin analogue, gonadotropin-releasing hormone analogue, leuprolide, goserelin, antidiuretic hormone, antidiuretic hormone analogue, oxytocin, estrogen, progestin, specific estrogen receptor modulator (SERM), uterine, stimulant, uterine relaxant, androgen, antiandrogen, prostaglandin, dopamine receptor agonist, alpha-adrenoreceptor blocker, anabolic steroid, an antianxiety agent, an antipsychotic agent, an antidepressant, beta-2 agonist, anticholinergic bronchodilator, theophylline, aminophylline, nedocromil sodium, sodium cromoglycate, leukotriene receptor antagonist, corticosteroid, expectorant, mucolytic agent, antihistamine, pseudoephedrine, or a neuraminidase inhibitor, betagan, betimol, timoptic, betoptic, betoptic, ocupress, optipranolol, xalatan, alphagan, azopt, trusopt, cospot, pilocar, pilagan, propine, opticrom, acular, livostin, alomide, emadine, patanol, alrex, dexacidin, maxitrol, tobradex, blephamide, ocufen, voltaren, profenal, pred forte, econpred plus, eflone, flarex, inflamase forte, inflamase mild, lotemax, vexol, polytrim, illotycin, ciloxan, ocuflox, tobrex, or garamycin, or any combination thereof.

In one embodiment, this invention provides a method of binding a selective androgen receptor modulator compound to an androgen receptor, comprising the step of contacting the androgen receptor with the compound of this invention or its isomer, pharmaceutically acceptable salt, pharmaceutical product, polymorph, crystal, hydrate, N-oxide or any combination thereof, or a composition comprising the same, in an amount effective to bind the selective androgen receptor modulator compound to the androgen receptor.

In one embodiment, this invention provides a method of suppressing spermatogenesis in a subject comprising contacting an androgen receptor of the subject with the compound of this invention or its isomer, pharmaceutically acceptable salt, pharmaceutical product, crystal, hydrate, N-oxide or any combination thereof, or a composition comprising the same, in an amount effective to suppress sperm production.

In one embodiment, this invention provides a method of contraception in a male subject, comprising the step of administering to the subject a compound of this invention or its isomer, pharmaceutically acceptable salt, pharmaceutical product, crystal, hydrate, N-oxide or any combination thereof, or a composition comprising the same, in an amount effective to suppress sperm production in the subject, thereby effecting contraception in the subject.

In one embodiment, this invention provides a method of hormone therapy comprising the step of contacting an androgen receptor of a subject a compound of this invention or its isomer, pharmaceutically acceptable salt, pharmaceutical product, crystal, hydrate, N-oxide or any combination thereof, or a composition comprising the same, in an amount effective to effect a change in an androgen-dependent condition.

In one embodiment, this invention provides a method of treating a subject suffering from prostate cancer, comprising the step of administering to said subject a compound of this invention, or its isomer, pharmaceutically acceptable salt, pharmaceutical product, crystal, hydrate, N-oxide or any combination thereof, or a composition comprising the same in an amount effective to treat prostate cancer in the subject.

In one embodiment, this invention provides a method of delaying the progression of prostate cancer in a subject suffering from prostate cancer, comprising the step of administering to said subject a compound of this invention or its isomer, pharmaceutically acceptable salt, pharmaceutical product, crystal, N-oxide, hydrate, or any combination thereof, or a composition comprising the same in an amount effective to delay the progression of prostate cancer in the subject.

In one embodiment, this invention provides a method of treating a bone-related disorder in a subject, or increasing a bone mass in a subject, promoting bone formation in a subject, administering an effective amount of a compound of this invention or its isomer, pharmaceutically acceptable salt, pharmaceutical product, crystal, hydrate, N-oxide or any combination thereof, or a composition comprising the same, in an amount effective to treat said bone-related disorder.

According to this aspect, and in one embodiment, the subject suffers from osteoporosis, osteopenia, increased bone resorption, bone fracture, bone frailty, loss of bone mineral density (BMD), or any combination thereof. In one embodiment, the method increases the strength of a bone of said subject. In one embodiment, the compound stimulates or enhances osteoblastogenesis, or in another embodiment the compound inhibits osteoclast proliferation.

In one embodiment, this invention provides a method of treating, reducing the incidence of, delaying progression of, reducing the severity of, or alleviating symptoms associated with a muscle wasting disorder in a subject, comprising the step of administering to said a compound of this invention or its isomer, pharmaceutically acceptable salt, pharmaceutical product, crystal, hydrate, N-oxide or any combination thereof, or a composition comprising the same, in an amount effective to treat the muscle wasting disorder in said subject.

According to this aspect, and in one embodiment, the muscle wasting disorder is due to a pathology, illness, disease or condition. In one embodiment, the pathology, illness, disease or condition is neurological, infectious, chronic or genetic. In one embodiment, the pathology, illness, disease or condition is a Muscular Dystrophy, a Muscular Atrophy, X-linked spinal-bulbar Muscular Atrophy (SBMA), a Cachexia, malnutrition, Leprosy, Diabetes, Renal Disease, Chronic Obstructive Pulmonary Disease (COPD), Cancer, end stage Renal failure, Sarcopenia, Emphysema, Osteomalacia, HIV Infection, AIDS, or Cardiomyopathy.

In one embodiment, the muscle wasting disorder is an age-associated muscle wasting disorder; a disuse deconditioning-associated muscle wasting disorder; or the muscle wasting disorder is due to chronic lower back pain; burns; central nervous system (CNS) injury or damage; peripheral nerve injury or damage; spinal cord injury or damage; chemical injury or damage; or alcoholism.

In one embodiment, this invention provides a method of treating, reducing the severity of, reducing the incidence of, delaying the onset of, or reducing pathogenesis of diabetes in a human subject, comprising administering an effective amount of a compound of this invention or its isomer, pharmaceutically acceptable salt, pharmaceutical product, crystal, N-oxide, hydrate or any combination thereof, to said subject.

In one embodiment, this invention provides, a method of treating, reducing the severity of, reducing the incidence of, delaying the onset of, or reducing pathogenesis of glucose intolerance in a human subject, comprising the step of administering an effective amount of a compound of this invention or its isomer, pharmaceutically acceptable salt, pharmaceutical product, crystal, N-oxide, hydrate or any combination thereof to said subject.

In one embodiment, this invention provides a method of treating, reducing the severity of, reducing the incidence of, delaying the onset of, or reducing pathogenesis of hyperinsulinemia in a human subject, comprising the step of administering an effective amount of a compound of this invention or its isomer, pharmaceutically acceptable salt, pharmaceutical product, crystal, N-oxide, hydrate or any combination thereof to said subject.

In one embodiment, this invention provides a method of treating, reducing the severity of, reducing the incidence of, delaying the onset of, or reducing pathogenesis of insulin resistance in a human subject, comprising the step of administering an effective amount of a compound of this invention or its isomer, pharmaceutically acceptable salt, pharmaceutical product, crystal, N-oxide, hydrate or any combination thereof to said subject.

In one embodiment, this invention provides a method of treating, reducing the severity of, reducing the incidence of, delaying the onset of, or reducing pathogenesis of diseases associated with diabetes comprising the step of administering an effective amount of a compound of this invention or its isomer, pharmaceutically acceptable salt, pharmaceutical product, crystal, N-oxide, hydrate or any combination thereof to said subject.

In one embodiment, this invention provides a method of treating, reducing the severity of, reducing the incidence of, delaying the onset of, or reducing pathogenesis of fatty liver conditions in a human subject, comprising the step of administering an effective amount of a compound of this invention or its isomer, pharmaceutically acceptable salt, pharmaceutical product, crystal, N-oxide, hydrate or any combination thereof to said subject.

In one embodiment, this invention provides a method of treating, reducing the severity of, reducing the incidence of, delaying the onset of, or reducing the pathogenesis of cardiovascular disease in a human subject, comprising the step of administering an effective amount of a compound of this invention or its isomer, pharmaceutically acceptable salt, pharmaceutical product, crystal, N-oxide, hydrate or any combination thereof to said subject.

In one embodiment, this invention provides a method of treating reducing the severity of, reducing the incidence of, delaying the onset of, or reducing the pathogenesis of cachexia in a subject, comprising the step of administering an effective amount of a compound of this invention or its isomer, pharmaceutically acceptable salt, pharmaceutical product, crystal, N-oxide, hydrate or any combination thereof to said subject.

In one embodiment, this invention provides a method of treating a disease or condition of the eye of a subject, comprising the step of administering an effective amount of a compound of this invention or its isomer, pharmaceutically acceptable salt, pharmaceutical product, crystal, N-oxide, hydrate or any combination thereof to the subject. In one embodiment, the disease or condition of the eye comprises Sjogren's syndrome, or xerophthalmia.

In one embodiment, the present invention provides a method of reducing a fat mass in a subject comprising the step of administering an effective amount of a compound of this invention or its isomer, pharmaceutically acceptable salt, pharmaceutical product, crystal, N-oxide, hydrate or any combination thereof to the subject.

In one embodiment, the present invention provides a method of increasing a lean mass in a subject comprising the step of administering an effective amount of a compound of this invention or its isomer, pharmaceutically acceptable salt, pharmaceutical product, crystal, N-oxide, hydrate or any combination thereof to the subject.

In another embodiment, this invention provides a method of suppressing spermatogenesis; contraception in a male; hormone therapy; treating prostate cancer; delaying the progression of prostate cancer; treating a bone-related disorder in a subject, or increasing a bone mass in a subject and/or promoting bone formation in a subject; treating, reducing the incidence of, delaying progression of, reducing the severity of, or alleviating symptoms associated with a muscle wasting disorder; treating, reducing the severity of, reducing the incidence of, delaying the onset of, or reducing pathogenesis of diabetes; treating, reducing the severity of, reducing the incidence of, delaying the onset of, or reducing pathogenesis of glucose intolerance; treating, reducing the severity of, reducing the incidence of, delaying the onset of, or reducing pathogenesis of hyperinsulinemia; treating, reducing the severity of, reducing the incidence of, delaying the onset of, or reducing pathogenesis of insulin resistance; treating, reducing the severity of, reducing the incidence of, delaying the onset of, or reducing pathogenesis of diseases associated with diabetes; treating, reducing the severity of, reducing the incidence of, delaying the onset of, or reducing pathogenesis of fatty liver conditions; treating, reducing the severity of, reducing the incidence of, delaying the onset of, or reducing pathogenesis of cardiovascular disease; treating reducing the severity of, reducing the incidence of, delaying the onset of, or reducing pathogenesis of cachexia; treating a disease or condition of the eye; reducing a fat mass; or increasing a lean mass in a subject, comprising the step of administering an effective amount of a compound of this invention or its isomer, pharmaceutically acceptable salt, pharmaceutical product, crystal, N-oxide, hydrate or any combination thereof to the subject as herein described.

BRIEF DESCRIPTION OF THE DRAWINGS

The present invention will be understood and appreciated more fully from the following detailed description taken in conjunction with the appended drawings in which:

FIG. 1: Synthetic schemes for the preparation of compound of formula II. FIG. 1I is a synthetic scheme for preparation of a racemic mixture of a compound of formula II, involving oxazolidinedione intermediate and B ring addition prior to A ring.

DETAILED DESCRIPTION OF THE PRESENT INVENTION

Figure 1A:
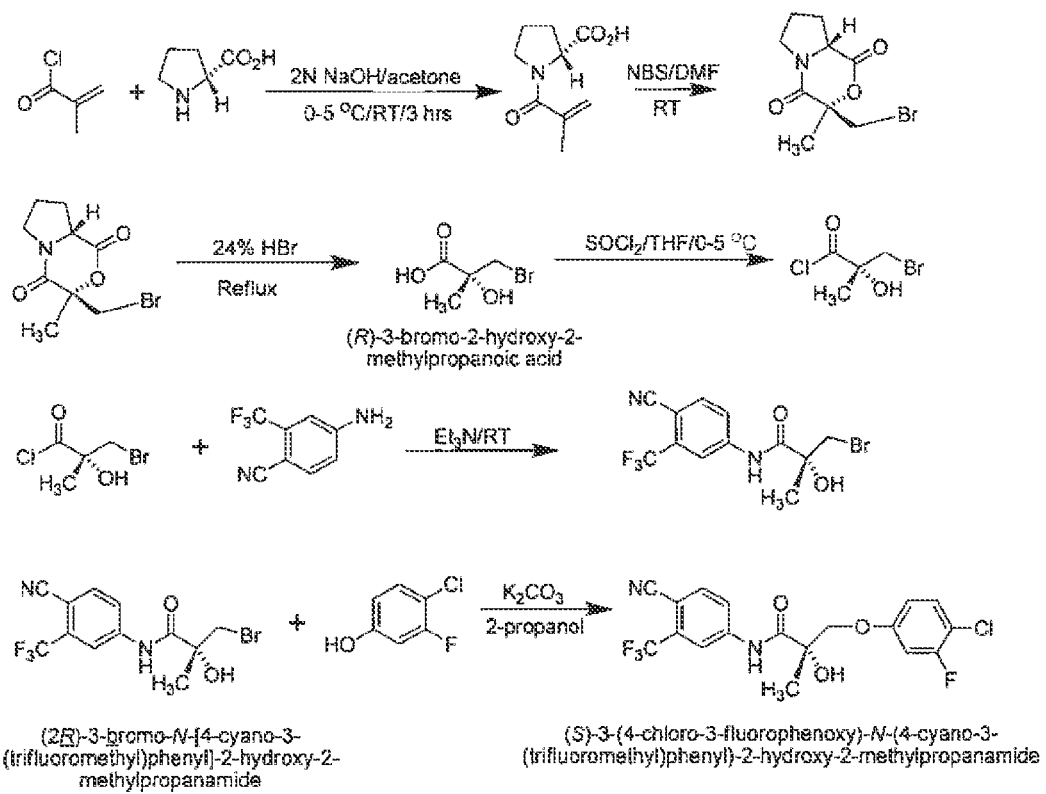
FIG. 1A is a synthetic scheme for the preparation of an (S) enantiomer of a compound of formula II (S-II).

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention provides, in one embodiment, a substituted acylanilide characterized by the structure of Formula I. In one embodiment, the compound is a SARM. IN one embodiment, the compound is useful in treating a variety of conditions or diseases, including, inter alia, oral testosterone replacement therapy, male contraception, maintaining sexual desire in women, osteoporosis, treating prostate cancer and/or imaging prostate cancer. In some embodiments, the compounds of this invention are nonsteroidal ligands for the AR and exhibit androgenic and/or anabolic activity. In some embodiments, the compounds are partial agonists or partial antagonists in a tissue selective manner. In some embodiments, the compounds are full agonists or full antagonists in a tissue selective manner, which in some embodiments, allows for tissue-selective androgenic and/or anabolic effects. These agents may be active alone or in combination with progestins or estrogens, or other agents, as herein described. In other embodiments, the agents are agonists, antagonists, partial agonists or partial antagonists.

In some embodiments, this invention provides compounds, which are useful in androgen replacement therapy (ART), useful in a) improving body composition; b) increasing bone mineral density (BMD); c) increasing bone mass; d) increasing bone strength; e) improving bone function; f) decreasing fracture risk; g) increasing muscle strength; h) increasing muscle function; i) improving exercise tolerance; j) enhancing libido; k) improving sexual performance; and/or l) improving mood and/or m) improving cognition.

In some embodiments, this invention provides synthetic processes of preparation of the SARM compounds of this invention. In some embodiments, the invention provides compositions comprising the selective androgen modulator compounds or use of the same for binding an AR, modulating spermatogenesis, bone formation and/or resorption, treating muscle wasting or diseases associated with muscle wasting, treating prostate cancer, and/or providing hormonal therapy for androgen-dependent conditions.

In one embodiment, the present invention provides, a compound represented by the structure of formula (I):

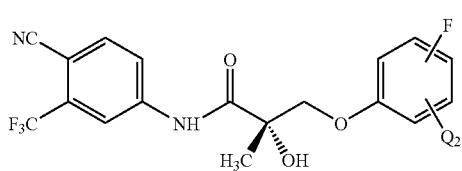
(I)

wherein $Q_2$ is alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; and R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

or its isomer, pharmaceutically acceptable salt, pharmaceutical product, N-oxide, hydrate or any combination thereof.

In one embodiment, the present invention provides, a compound represented by the structure of formula II:

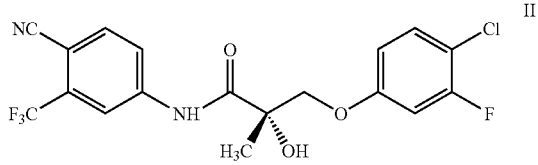
II or its isomer, pharmaceutically acceptable salt, pharmaceutical product, N-oxide, hydrate or any combination thereof.

In one embodiment, the present invention provides, a compound represented by the structure of formula III:

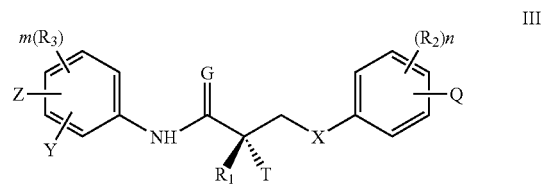
III wherein X is a bond, O, $CH_2$, NH, Se, PR, NO or NR;
G is O or S;
T is OH, OR, —$NHCOCH_3$, or NHCOR;
R is alkyl, haloalkyl, dihaloalkyl, trihaloalkyl, $CH_2F$, $CHF_2$, $CF_3$, $CF_2CF_3$, aryl, phenyl, halogen, alkenyl or OH;
$R_1$ is $CH_3$, $CH_2F$, $CHF_2$, $CF_3$, $CH_2CH_3$, or $CF_2CF_3$;
$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, SR;
$R_3$ is H, F, Cl, Br, I, CN, $NO_2$, COR, COOH, CONHR, $CF_3$, $Sn(R)_3$, or
$R_3$ together with the benzene ring to which it is attached forms a fused ring system represented by the structure:

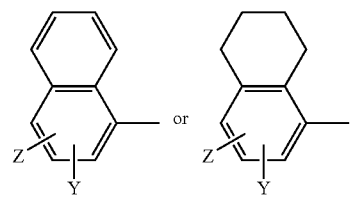

Z is $NO_2$, CN, Cl, F, Br, I, H, COR, COOH, or CONHR;
Y is $CF_3$, alkoxy, alkyl, hydroxyalkyl, alkylaldehyde, formyl, H, F, Br, Cl, I, CN, or $Sn(R)_3$;
Q is H, alkyl, halogen, $CF_3$, CN $CR_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OH, OR, COR, OCOR, $OSO_2R$, $SO_2R$, SR; or Q together with the benzene ring to which it is attached is a fused ring system represented by structure A, B or C:

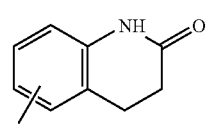
A

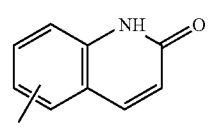
B

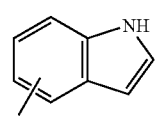
C n is an integer of 1-4; and m is an integer of 1-3;

wherein if $R_3$ is H, then none of Z or Y or $R_2$ or Q are H;

or an isomer, pharmaceutically acceptable salt, pharmaceutical product, N-oxide, hydrate thereof or any combination thereof.

In one embodiment, the present invention provides a compound of formula II wherein X is O. In another embodiment, the present invention provides a compound of formula II wherein T is OH. In another embodiment, the present invention provides a compound of formula II wherein $R_1$ is $CH_3$. In another embodiment, the present invention provides a compound of formula II wherein Z is CN. In another embodiment, the present invention provides a compound of formula II wherein Z is F. In another embodiment, the present invention provides a compound of formula II wherein Z is $NO_2$. In another embodiment, the present invention provides a compound of formula II, wherein Y is $CH_3$. In another embodiment, the present invention provides a compound of formula II, wherein Y is H. In another embodiment, the present invention provides a compound of formula II wherein Y is $CF_3$. In another embodiment, the present invention provides a compound of formula II, wherein Y is Cl. In another embodiment, the present invention provides a compound of formula II wherein $R_3$ is H and none of Y, Z, Q or $R_2$ are H. In another embodiment, the present invention provides a compound of formula II wherein $R_3$ is CN. In another embodiment, the present invention provides a compound of formula II wherein $R_3$ is Cl. In another embodiment, the present invention provides a compound of formula II wherein $R_3$ is F. In another embodiment, the present invention provides a compound of formula II wherein Q is CN. In another embodiment, the present invention provides a compound of formula II wherein Q is F. In another embodiment, the present invention provides a compound of formula II wherein Q is Cl.

In one embodiment, the present invention provides a compound characterized by the structure of formula IV:

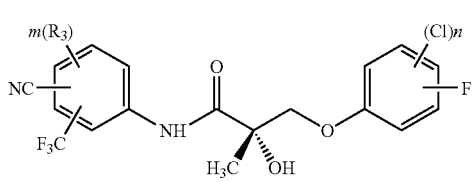

IV wherein $R_3$, m and n are as described for the structure of formula III.

In one embodiment, the present invention provides a compound characterized by the structure of formula V:

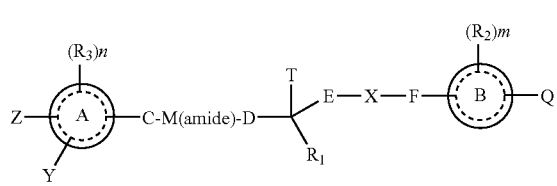

V wherein

A and B rings are independently carbocyclic, heterocyclic, aryl, heteroaryl, bicyclic, polycyclic, or spiro rings.

T is OH, OR, —$NHCOCH_3$, or NHCOR;

X is bond, O, $CH_2$, NH, S, SO, $SO_2$, Se, PR, NO or NR;

Z is $NO_2$, CN, COR, COOH, or CONHR;

Y is $CF_3$, alkoxy, hydroxyalkyl, alkylaldehyde, formyl, F, Br, Cl, I, CN, alkyl or $Sn(R)_3$;

Q is H, alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, SR;

R is alkyl, haloalkyl, dihaloalkyl, trihaloalkyl, $CH_2F$, $CHF_2$, $CF_3$, $CF_2CF_3$; aryl, phenyl, halogen, alkenyl, alkynyl, haloalkenyl, haloalkynyl, perhaloalkyl, or OH;

$R_1$ $CH_3$, $CH_2F$, $CHF_2$, $CF_3$, $CH_2CH_3$, or $CF_2CF_3$;

$R_2$ is F, Cl, Br, I, $CH_3$, $CF_3$, OH, CN, $NO_2$, $NHCOCH_3$, $NHCOCF_3$, NHCOR, alkyl, arylalkyl, allyl, alkenyl, alkynyl, OR, $NH_2$, NHR, $N(R)_2$, SR;

$R_3$ is H, F, Cl, Br, I, CN, $NO_2$, COR, COOH, CONHR, $CF_3$, alkyl, arylalkyl, allyl, alkenyl, alkynyl, $Sn(R)_3$;

C, D, E and F are independently a bond, alkyl ($C_1$-$C_5$), alkenyl ($C_1$-$C_5$), alkynyl ($C_1$-$C_5$), alkoxy ($C_1$-$C_5$), alkylester ($C_1$-$C_5$), alkylether ($C_1$-$C_5$), alkylamide ($C_1$-$C_5$), alkylcarbamate ($C_1$-$C_5$), alkyl amine ($C_1$-$C_5$), alkyl ketone ($C_1$-$C_5$), alkyl-COOH($C_1$-$C_5$);

M is substituted or unsubstituted amide, substituted or unsubstituted thioamide substituted or unsubstituted reverse amide, substituted or unsubstituted reverse thioamide, substituted or unsubstituted amine, substituted or unsubstituted carbamate, substituted or unsubstituted urea, substituted or unsubstituted thiourea substituted or unsubstituted ester, substituted or unsubstituted reverse ester, or substituted or unsubstituted ether; n is 1-3; and m is 1-4.

In another embodiment, the present invention provides a compound represented by the structure of formula V:

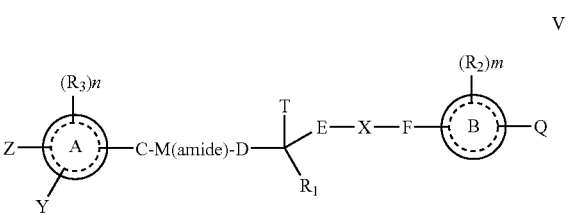

V wherein

A and B rings are independently carbocyclic, heterocyclic, aryl, heteroaryl, bicyclic, polycyclic, or spiro rings.

T is OH, OR, —$NHCOCH_3$, or NHCOR;

X is bond, O, $CH_2$, NH, S, SO, $SO_2$, Se, PR, NO or NR;

Z is $NO_2$, CN, COR, COOH, or CONHR;

Y is $CF_3$, alkoxy, hydroxyalkyl, alkylaldehyde, formyl, F, Br, Cl, I, CN, alkyl or $Sn(R)_3$;

Q is H, alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, SR;

R is alkyl, haloalkyl, dihaloalkyl, trihaloalkyl, $CH_2F$, $CHF_2$, $CF_3$, $CF_2CF_3$; aryl, phenyl, halogen, alkenyl, alkynyl, haloalkenyl, haloalkynyl, perhaloalkyl, or OH;

$R_1$ $CH_3$, $CH_2F$, $CHF_2$, $CF_3$, $CH_2CH_3$, or $CF_2CF_3$;

$R_2$ is F, Cl, Br, I, $CH_3$, $CF_3$, OH, CN, $NO_2$, $NHCOCH_3$, $NHCOCF_3$, NHCOR, alkyl, arylalkyl, allyl, alkenyl, alkynyl, OR, $NH_2$, NHR, $N(R)_2$, SR;

$R_3$ is hydrogen;

C, D, E and F are independently a bond, alkyl ($C_1$-$C_5$), alkenyl ($C_1$-$C_5$), alkynyl ($C_1$-$C_5$), alkoxy ($C_1$-$C_5$), alkylester ($C_1$-$C_5$), alkylether ($C_1$-$C_5$), alkylamide ($C_1$-$C_5$), alkylcarbamate ($C_1$-$C_5$), alkyl amine ($C_1$-$C_5$), alkyl ketone ($C_1$-$C_5$), alkyl-COOH($C_1$-$C_5$);

M is substituted or unsubstituted amide, substituted or unsubstituted thioamide substituted or unsubstituted reverse amide, substituted or unsubstituted reverse thioamide, substituted or unsubstituted amine, substituted or unsubstituted carbamate, substituted or unsubstituted urea, substituted or unsubstituted thiourea substituted or unsubstituted ester, substituted or unsubstituted reverse ester, or substituted or unsubstituted ether;

n is 1-3; and m is 1-4.

In another embodiment, preferred examples of ring A of formula V include carbazoles, norharmans, saccharins, isatins, purines, isatoic anhydrides, benzisoxazoles, benzisthiazoles, quinolines, quinolinones, tetrahydroquinolines, isoquinolines, tetrahydroisoquinolines, azulenes, 1-aza-azulenes, and 1,3-diaza-azulenes.

In one embodiment, preferred examples of ring B, of formula V, include pyridines, pyrazines, pyrimidines, pyridazines, thiophenes, pyrroles, furans, triazines, tetrazines, isothiazoles, thiazoles, isoxazoles, oxazoles, furazans, imidazoles, pyrazoles, thiadiazoles, triazoles, and tetrazoles.

In another embodiment, less preferred examples of rings A and B include the following: aromatics such as benzene, thiophenes, pyrroles, furans, isothiazoles, thiazoles, isoxazoles, oxazoles, furazans, imidazoles, pyrazoles, thiadiazoles, 1,2,3-triazoles, 1,2,4-triazoles, tetrazoles, pyridines, pyrazines, pyrimidines, pyridazines, 1,3,5-triazines, tetrazines, bicyclics such as indolines, isoindolines, indenes, pentalenes, isoindoles, indolenines, idolizines, indazoles, oxindoles, isatins, saccharins, quinolizidines, pyrrolizidines, tetrahydroquinolines, tetrahydroisoquinolines, decahydroquinolines, decahydroisoquinolines, heterocyclics and carbocyclics such as 1,2,4-oxadiazoles, aziridines, azetidines, pyrrolidines, pyrrolidinones, piperidines, piperidinones, piperazines, 2,5-dioxopiperazines, Δ2- and Δ3-thiazolines, oxiranes, oxetans, tetrahydrofurans, tetrahydropyrans, thiirans, thietans, thiolans, tetrahydrothiopyrans, azepines, oxepines, sultones, isoxazolidines, sultams, 5-oxazolones, oxazolidines, succinimides, ethylene, ureas, imidazolines, thioimidazolidines, hydantoins, thiohydantoins, oxazolidinediones, 1,4-dihydropyridines, cyclopentadieneones, cyclopentadienes, 1,3-oxathioles, 1,3-oxazinan-2-ones, fulvenes, fulvalenes, pyrans, 1,4-thiazines, 4-pyridthiones, 4-pyrones, 2-pyrimidones, uracils, barbituric acids, and 3-pyrazolidones.

In one embodiment, the present invention provides a compound represented by the structure of formula VI:

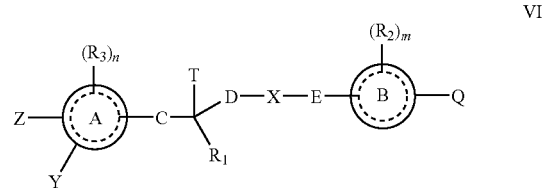

VI

In another embodiment, the present invention provides a compound represented by the structure of formula VI:

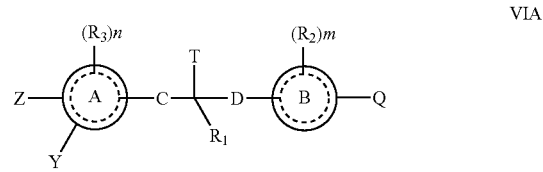

VI wherein $R_3$ is hydrogen, A and B rings, Y, Z, Q, $R_2$, C, D, E, T, $R_1$, X n, and m are as defined in compound of formula V.

In one embodiment, the present invention provides a compound represented by the structure of formula 15A:

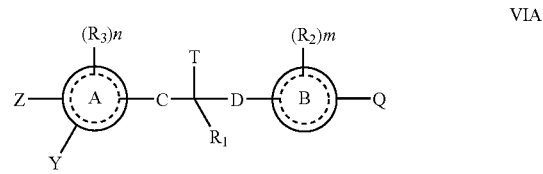

VIA wherein A and B rings, Y, Z, Q, $R_2$, $R_3$, C, D, E, T, $R_1$, X, n, and m are as defined in compound of formula V.

In another embodiment, the present invention provides a compound represented by the structure of formula 15A:

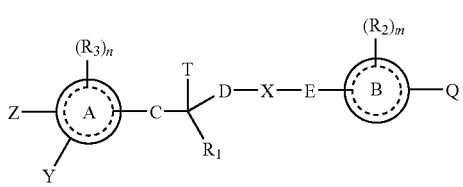

VIA wherein $R_3$ is hydrogen, A and B rings, Y, Z, Q, $R_2$, C, D, E, T, $R_1$, X n, and m are as defined in compound of formula V.

In another embodiment, preferred examples of ring A of formula VI and VIA include carbazoles, norharmans, saccharins, indoles, isoindoles, indene, benzothiophene, benzofuran, α and β naphthenes, dihydronaphthenes, tetrahydronaphthylenes, azepines, diazepines, isatins, purines, isatoic anhydrides, benzisoxazoles, benzisthiazoles, benzoxazole, benzthiazoles, quinolines, quinolinones, tetrahydroquinolines, isoquinolines, tetrahydroisoquinolines, azulenes, 1-aza-azulenes, and 1,3-diaza-azulenes.

In one embodiment, the present invention provides a compound represented by the structure of formula VII:

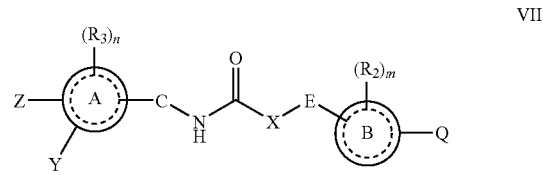

VII wherein
  A and B rings are independently carbocyclic, heterocyclic, aryl, heteroaryl, bicyclic, polycyclic, or spiro rings.
  X is bond, O, $CH_2$, NH, S, SO, $SO_2$, Se, PR, NO or NR;
  Z is $NO_2$, CN, COR, COOH, or CONHR;
  Y is $CF_3$, alkoxy, hydroxyalkyl, alkylaldehyde, formyl, F, Br, Cl, I, CN, alkyl or $Sn(R)_3$;
  Q is H, alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, SR;
  R is alkyl, haloalkyl, dihaloalkyl, trihaloalkyl, $CH_2F$, $CHF_2$, $CF_3$, $CF_2CF_3$; aryl, phenyl, halogen, alkenyl, alkynyl, haloalkenyl, haloalkynyl, perhaloalkyl, or OH;
  $R_1$ $CH_3$, $CH_2F$, $CHF_2$, $CF_3$, $CH_2CH_3$, or $CF_2CF_3$;
  $R_2$ is F, Cl, Br, I, $CH_3$, $CF_3$, OH, CN, $NO_2$, $NHCOCH_3$, $NHCOCF_3$, NHCOR, alkyl, arylalkyl, allyl, alkenyl, alkynyl, OR, $NH_2$, NHR, $N(R)_2$, SR;
  $R_3$ is H, F, Cl, Br, I, CN, $NO_2$, COR, COOH, CONHR, $CF_3$, alkyl, arylalkyl, allyl, alkenyl, alkynyl, $Sn(R)_3$;
  C, D, E and F are independently a bond, alkyl ($C_1$-$C_5$), alkenyl ($C_1$-$C_5$), alkynyl ($C_1$-$C_5$), alkoxy ($C_1$-$C_5$), alkylester ($C_1$-$C_5$), alkylether ($C_1$-$C_5$), alkylamide ($C_1$-$C_5$), alkylcarbamate ($C_1$-$C_5$), alkyl amine ($C_1$-$C_5$), alkyl ketone ($C_1$-$C_5$), alkyl-COOH($C_1$-$C_5$);
n is 1-3; and
m is 1-4; wherein
if C and E are bonds, X is $CH_2$ or a bond than ring B is not a 5 membered ring comprising one sulfur atom and one nitrogen atom; and
if each of C, D, E and F is a bond, and each of A and B is a phenyl ring, and $R_3$ is H, then none of Z, Y, Q or $R_2$ are H.

In another embodiment, the present invention provides a compound represented by the structure of formula VII:

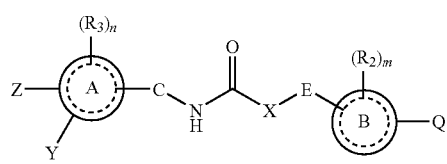

VII wherein $R_3$ is hydrogen, A and B rings, Y, Z, Q, $R_2$, C, E, X, n, and m are as defined hereinabove.

In another embodiment, the thiazine may include thiazolidine, thiazolidinone, or thiazole.

In one embodiment, the present invention provides a compound represented by the structure of formula VIII:

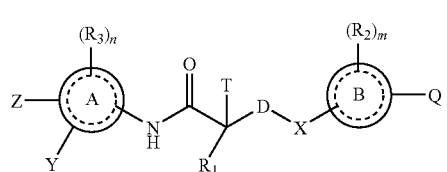

VIII wherein A and B rings, Y, Z, Q, $R_2$, $R_3$, D, T, $R_1$, X, n and m are as defined in compound of formula V.

In another embodiment, the present invention provides a compound represented by the structure of formula VIII:

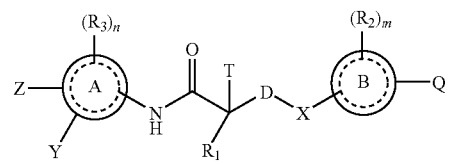

VIII wherein $R_3$ is hydrogen, A and B rings, Y, Z, Q, $R_2$, D, T, $R_1$, X, n and m are as defined in compound of formula V.

In one embodiment, the present invention provides a compound represented by the structure of formula IX:

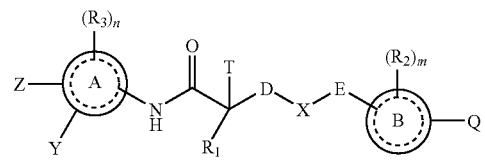

IX wherein A and B rings, Y, Z, Q, $R_2$, $R_3$, D, E T, $R_1$, X, n and m are as defined in compound of formula V.

In another embodiment, the present invention provides a compound represented by the structure of formula IX:

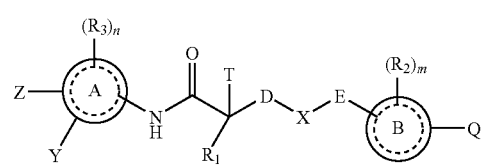

IX wherein $R_3$ is hydrogen, A and B rings, Y, Z, Q, $R_2$, D, E T, $R_1$, X, n and m are as defined in compound of formula V.

In one embodiment, the present invention provides a compound represented by the structure of formula X:

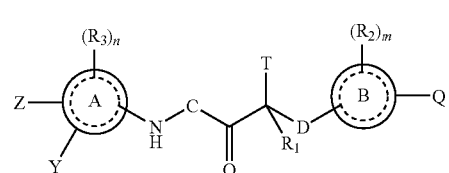

X wherein A and B rings, Y, Z, Q, $R_2$, $R_3$, C, D, T, $R_1$, n and m are as defined in compound of formula V.

In another embodiment, the present invention provides a compound represented by the structure of formula X:

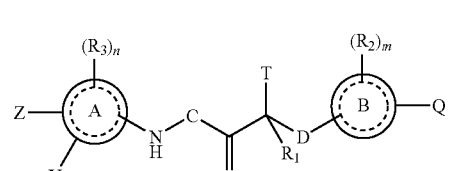

X wherein $R_3$ is hydrogen, A and B rings, Y, Z, Q, $R_2$, C, D, T, $R_1$, n and m are as defined in compound of formula V.

In one embodiment, the present invention provides a compound represented by the structure of formula XI:

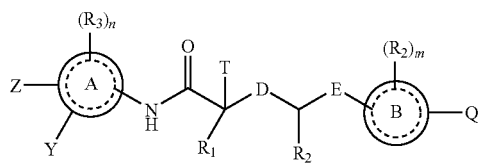

XI wherein A and B rings, Y, Z, Q, $R_2$, $R_3$, D, E, T, $R_1$, n and m are as defined in compound of formula V.

In another embodiment, the present invention provides a compound represented by the structure of formula XI:

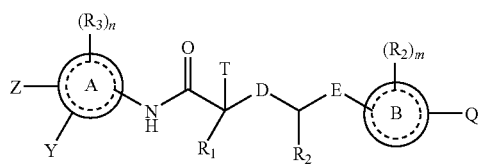

XI wherein $R_3$ is hydrogen and A and B rings, Y, Z, Q, $R_2$, D, E, T, $R_1$, n and m are as defined in compound of formula V.

In one embodiment, the present invention provides a compound represented by the structure of formula XII:

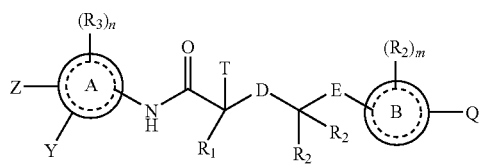

XII wherein A and B rings, Y, Z, Q, $R_2$, $R_3$, D, E, T, $R_1$, n and m are as defined in compound of formula V.

In another embodiment, the present invention provides a compound represented by the structure of formula XII:

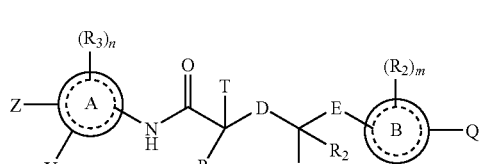

XII wherein A and B rings, Y, Z, Q, $R_2$, $R_3$, D, E, T, $R_1$, n and m are as defined in compound of formula V.

In one embodiment, the present invention provides a compound represented by the structure of formula XIII:

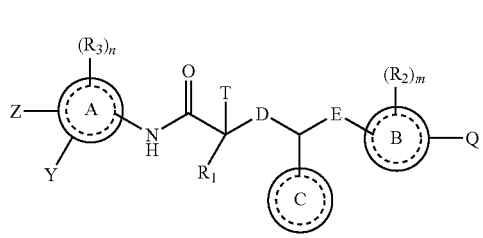

XIII wherein A and B rings, Y, Z, Q, $R_2$, $R_3$, D, E, T, $R_1$, n and m are as defined in compound of formula V; and wherein ring C is benzene, phenyl, benzyl, thiophenes, pyrroles, furans, isothiazoles, thiazoles, isoxazoles, oxazoles, furazans, imidazoles, pyrazoles, thiadiazoles, 1,2,3-triazoles, 1,2,4-triazoles, tetrazoles, pyridines, pyrazines, pyrimidines, pyridazines, 1,3,5-triazines, tetrazines, hydantoin, thiohydantoin, oxazolidinedione, cyclopentadieneone, cyclopentadiene, 1,3-oxathiole, fulvene, thiophene, pyrrole, furan, isoxazole, pyrazole, isothiazole, thiazole, oxazole, imidazole, imidazoline, pyridazine, pyrazine, pyrimidine, pyridine, fulvalene, quinazoline, phthalazine, cinnoline, quinoxaline, quinoline, isoquinoline, quinolinone, isoquinolinone, chroman, chromene, coumarin, isocoumarin.

In another embodiment, the present invention provides a compound represented by the structure of formula XIII:

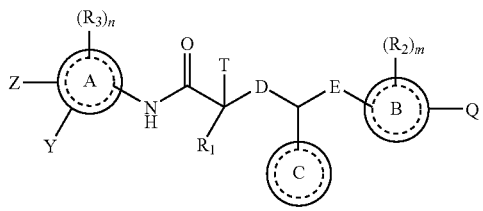

XIII

Wherein $R_3$ is hydrogen, A and B rings, Y, Z, Q, $R_2$, D, E, T, $R_1$, n and m are as defined in compound of formula V; and wherein ring C is benzene, phenyl, benzyl, thiophenes, pyrroles, furans, isothiazoles, thiazoles, isoxazoles, oxazoles, furazans, imidazoles, pyrazoles, thiadiazoles, 1,2,3-triazoles, 1,2,4-triazoles, tetrazoles, pyridines, pyrazines, pyrimidines, pyridazines, 1,3,5-triazines, tetrazines, hydantoin, thiohydantoin, oxazolidinedione, cyclopentadieneone, cyclopentadiene, 1,3-oxathiole, fulvene, thiophene, pyrrole, furan, isoxazole, pyrazole, isothiazole, thiazole, oxazole, imidazole, imidazoline, pyridazine, pyrazine, pyrimidine, pyridine, fulvalene, quinazoline, phthalazine, cinnoline, quinoxaline, quinoline, isoquinoline, quinolinone, isoquinolinone, chroman, chromene, coumarin, isocoumarin.

In one embodiment, the present invention provides a compound represented by the structure of formula XIV:

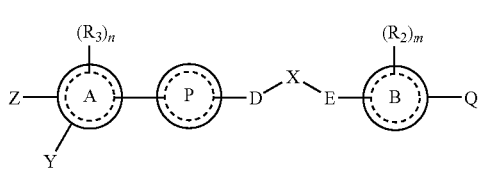

XIV wherein A and B rings, Y, Z, Q, $R_2$, $R_3$, D, E, X, n and m are as defined in compound of formula V; and wherein Ⓟ is hydantoin, thiohydantoin, oxazolidinedione, cyclopentadieneone, cyclopentadiene, 1,3-oxathiole, fulvene, thiophene, pyrrole, furan, isoxazole, pyrazole, isothiazole, thiazole, oxazole, imidazole, imidazoline, pyridazine, pyrazine, pyrimidine, pyridine, fulvalene, quinazoline, phthalazine, cinnoline, quinoxaline, quinoline, isoquinoline, quinolinone, isoquinolinone, chroman, chromene, coumarin, isocoumarin.

In another embodiment, the present invention provides a compound represented by the structure of formula XIV:

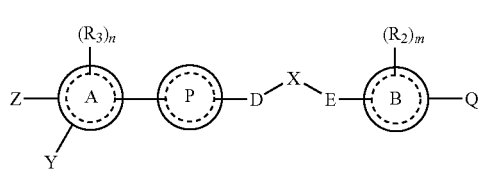

XIV wherein $R_3$ is hydrogen, and A and B rings, Y, Z, Q, $R_2$, $R_3$, D, E, X, n and m are as defined in compound of formula V; and wherein Ⓟ is hydantoin, thiohydantoin, oxazolidinedione, cyclopentadieneone, cyclopentadiene, 1,3-oxathiole, fulvene, thiophene, pyrrole, furan, isoxazole, pyrazole, isothiazole, thiazole, oxazole, imidazole, imidazoline, pyridazine, pyrazine, pyrimidine, pyridine, fulvalene, quinazoline, phthalazine, cinnoline, quinoxaline, quinoline, isoquinoline, quinolinone, isoquinolinone, chroman, chromene, coumarin, isocoumarin.

In one embodiment, the present invention provides a compound represented by the structure of formula XV:

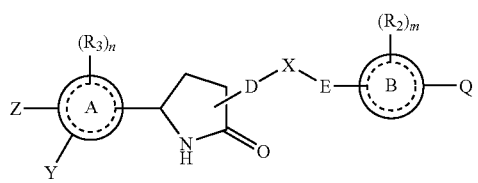

XV wherein A and B rings, Y, Z, Q, $R_2$, $R_3$, D, E, X, n and m are as defined in compound of formula V.

In another embodiment, the present invention provides a compound represented by the structure of formula XV:

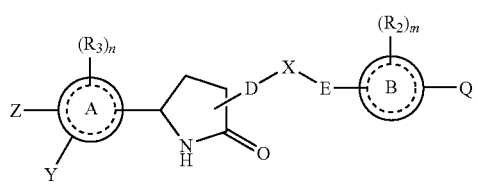

XV wherein $R_3$ is hydrogen, and A and B rings, Y, Z, Q, $R_2$, D, E, X, n and m are as defined in compound of formula V.

In one embodiment, the present invention provides a compound represented by the structure of formula XVI:

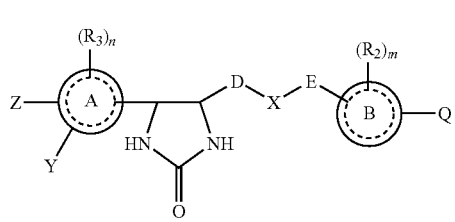

XVI wherein A and B rings, Y, Z, Q, $R_2$, $R_3$, D, E, X, n and m are as defined in compound of formula V.

In another embodiment, the present invention provides a compound represented by the structure of formula XVI:

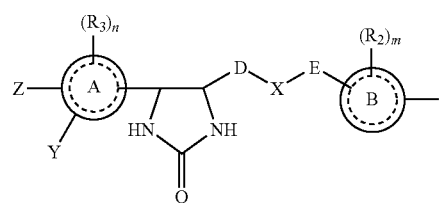

XVI wherein $R_3$ is hydrogen, and A and B rings, Y, Z, Q, $R_2$, D, E, X, n and m are as defined in compound of formula V.

In one embodiment, the present invention provides a compound represented by the structure of formula XVII:

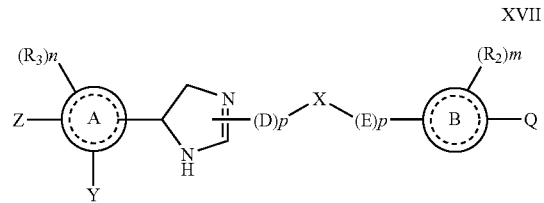

XVII wherein A and B rings, Y, Z, Q, $R_2$, $R_3$, D, E, X, n and m are as defined in compound of formula XVII.

In another embodiment, the present invention provides a compound represented by the structure of formula XVII:

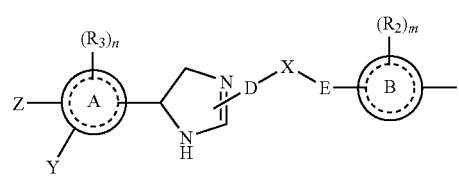

XVII wherein $R_3$ is hydrogen and A and B rings, Y, Z, Q, $R_2$, D, E, X, n and m are as defined in compound of formula V.

In one embodiment, the present invention provides a compound represented by the structure of formula XVIII:

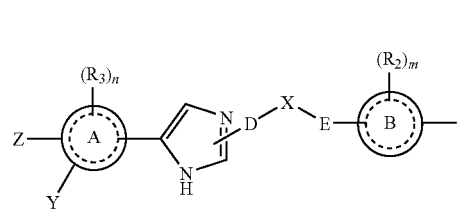

XVIII wherein A and B rings, Y, Z, Q, $R_2$, $R_3$, D, E, X, n and m are as defined in compound of formula V.

In another embodiment, the present invention provides a compound represented by the structure of formula XVIII:

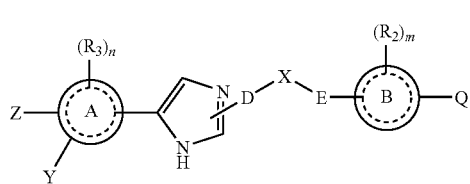

XVIII wherein $R_3$ is hydrogen and A and B rings, Y, Z, Q, $R_2$, D, E, X, n and m are as defined in compound of formula V.

In one embodiment, the present invention provides a compound represented by the structure of formula XIX:

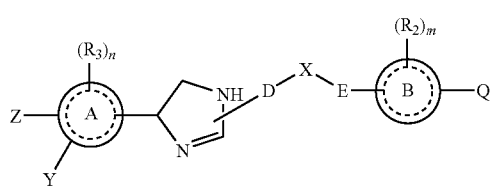

XIX wherein A and B rings, Y, Z, Q, $R_2$, $R_3$, D, E, X, n and m are as defined in compound of formula V.

In another embodiment, the present invention provides a selective androgen receptor modulator (SARM) compound represented by the structure of formula XIX:

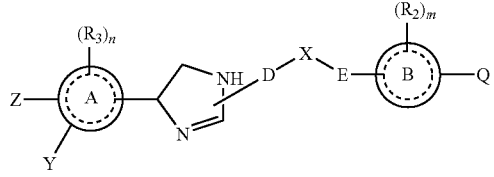

XIX wherein $R_3$ is hydrogen and A and B rings, Y, Z, Q, $R_2$, D, E, X, n and m are as defined in compound of formula V.

In one embodiment, the present invention provides a compound represented by the structure of formula XX:

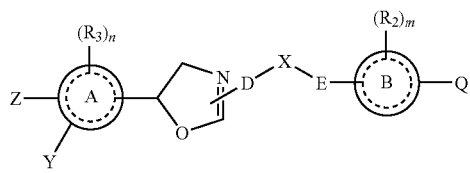

XX wherein A and B rings, Y, Z, Q, $R_2$, $R_3$, D, E, X, n and m are as defined in compound of formula V.

In another embodiment, the present invention provides a compound represented by the structure of formula XX:

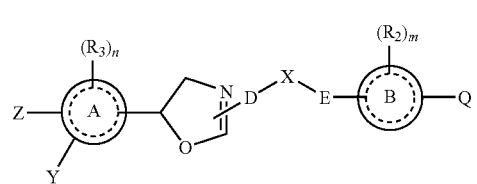

XX wherein $R_3$ is hydrogen and A and B rings, Y, Z, Q, $R_2$, D, E, X, n and m are as defined in compound of formula V.

In one embodiment, the present invention provides a compound represented by the structure of formula XXI:

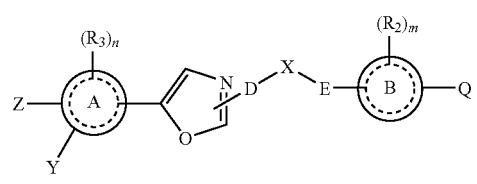

XXI wherein A and B rings, Y, Z, Q, $R_2$, $R_3$, D, E, X, n and m are as defined in compound of formula V.

In another embodiment, the present invention provides a compound represented by the structure of formula XXI:

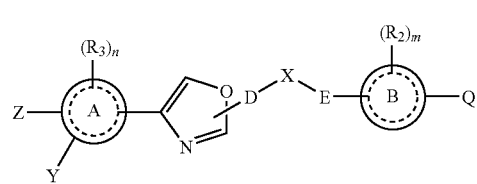

XXI wherein $R_3$ is hydrogen, A and B rings, Y, Z, Q, $R_2$, D, E, X, n and m are as defined in compound of formula V.

In one embodiment, the present invention provides a compound represented by the structure of formula XXII:

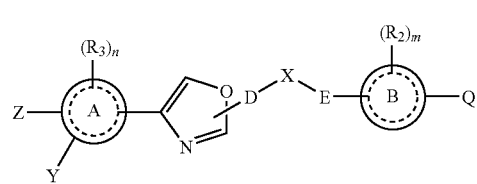

XXII wherein A and B rings, Y, Z, Q, $R_2$, $R_3$, D, E, X, n and m are as defined in compound of formula V.

In another embodiment, the present invention provides a compound represented by the structure of formula XXII:

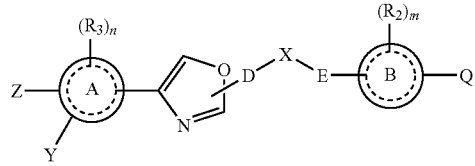

XXII wherein $R_3$ is hydrogen and A and B rings, Y, Z, Q, $R_2$, D, E, X, n, and m are as defined in compound of formula V.

In other specific non-limiting embodiments, ring A and its substituents include the following schematic structures:

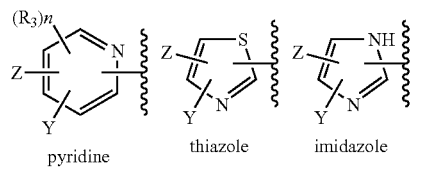

pyridine    thiazole    imidazole

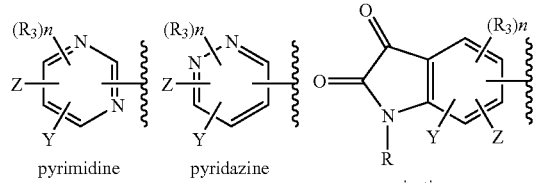

pyrimidine    pyridazine    isatin

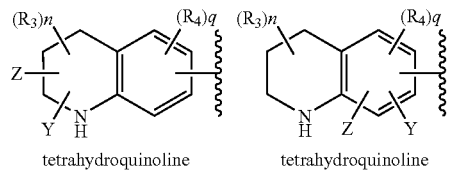

tetrahydroquinoline    tetrahydroquinoline

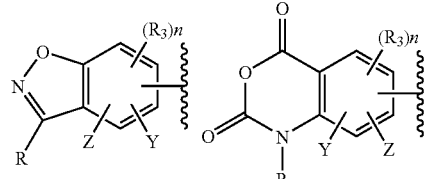

benzisoxazole    isatonic anhydride

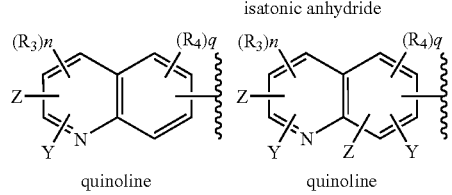

quinoline    quinoline

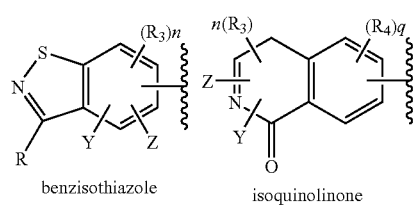

benzisothiazole    isoquinolinone

-continued

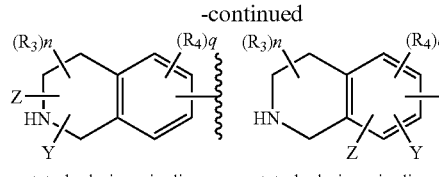

tetrahydroisoquinoline    tetrahydroisoquinoline

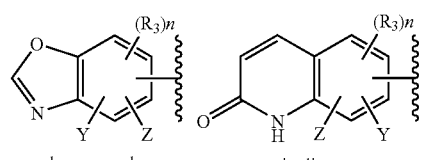

benzoxazole    quinolinone

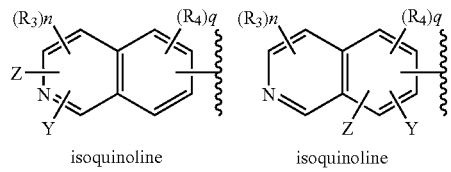

isoquinoline    isoquinoline

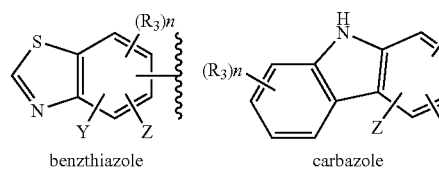

benzthiazole    carbazole

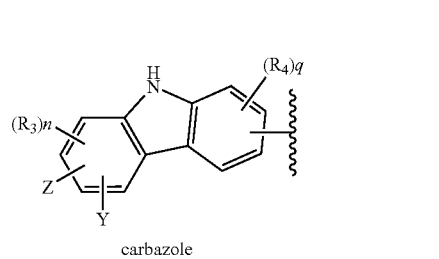

carbazole

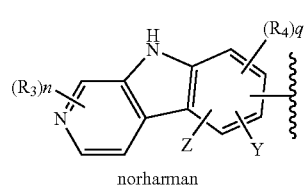

norharman

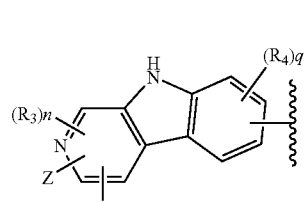

norharman wherein $R_3$ and $R_4$ are independently H, F, Cl, Br, I, CN, $NO_2$, COR, COOH, CONHR, $CF_3$, alkyl, arylalkyl, allyl, alkenyl, alkynyl, $Sn(R)_3$;

n and q are independently 1-3; and

R, Z and Y are as defined for structure V.

In other non-limiting embodiments, ring B and its substituents include the following schematic structures:
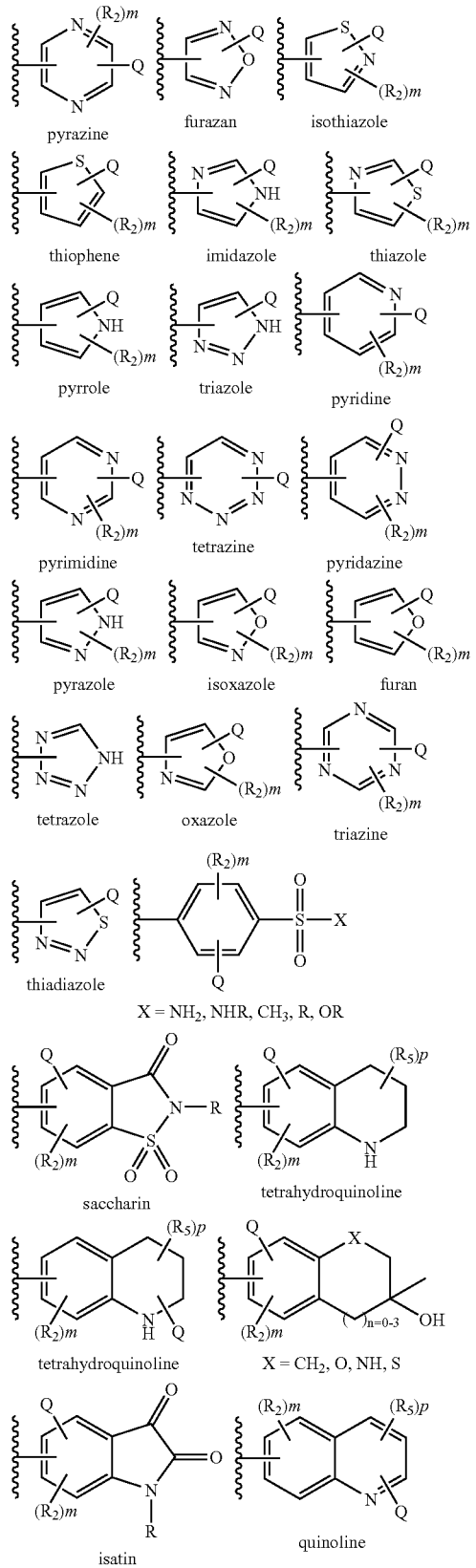
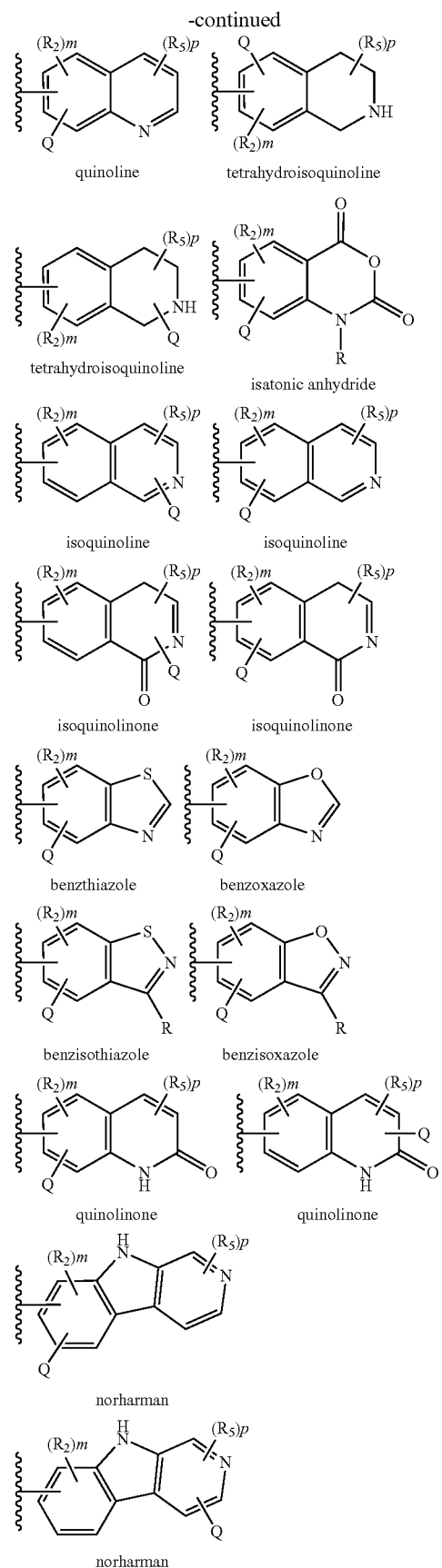

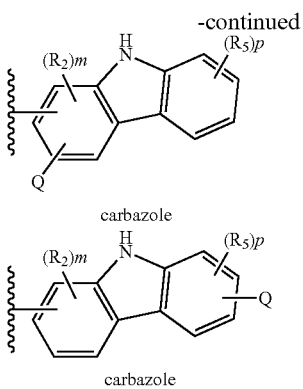

carbazole carbazole wherein
$R_2$ and $R_5$ are independently H, F, Cl, Br, I, CN, $NO_2$, COR, COOH, CONHR, $CF_3$, alkyl, arylalkyl, allyl, alkenyl, alkynyl, $Sn(R)_3$;
m and p are independently 1-3; and
R and Q are as defined for structure V.

In other non-limiting embodiments amide M include the following schematic structures:

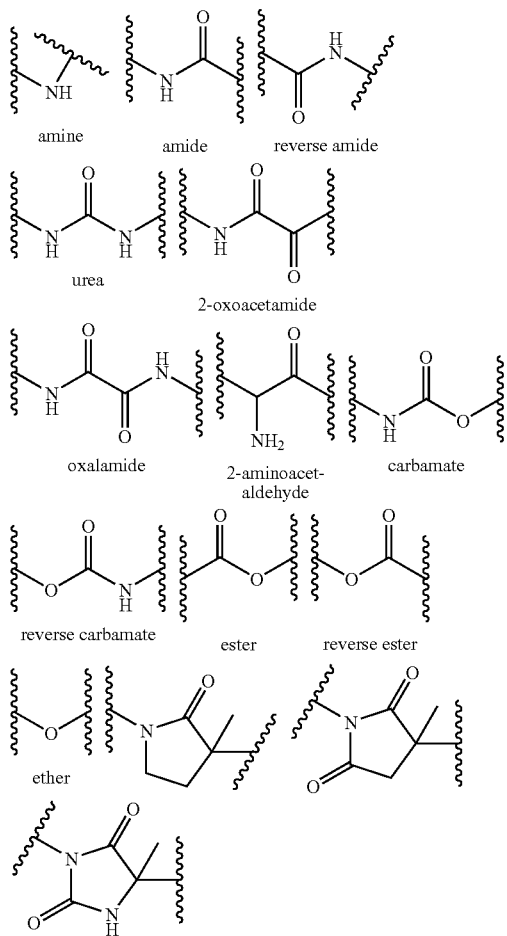

wherein each NH or $NH_2$ groups can be optionally substituted with an R group, and oxygen atoms may be also replaced with sulfur atoms; wherein R is alkyl, haloalkyl, dihaloalkyl, trihaloalkyl, $CH_2F$, $CHF_2$, $CF_3$, $CF_2CF_3$; aryl, phenyl, halogen, alkenyl, alkynyl, haloalkenyl, haloalkynyl, alkoxy, perhaloalkyl, or OH.

In one embodiment, the present invention provides a compound of any of formulas I-XXII wherein $R_2$ is F. In another embodiment, the present invention provides a compound of any of formulas I-XXII wherein $R_2$ is Cl. In another embodiment, the present invention provides a compound of any of formulas I-XXII wherein $R_2$ is Br. In another embodiment, the present invention provides a compound of any of formulas I-XXII wherein $R_2$ is I. In another embodiment, the present invention provides a compound of any of formulas I-XXII wherein $R_2$ is $CH_3$. In another embodiment, the present invention provides a compound of any of formulas I-XXII wherein $R_2$ is OH. In another embodiment, the present invention provides a compound of any of formulas I-XXII wherein $R_2$ is $CF_3$. In another embodiment, the present invention provides a compound of any of formulas I-XXII wherein $R_2$ is CN. In another embodiment, the present invention provides a compound of any of formulas I-XXII wherein $R_2$ is $NO_2$. In another embodiment, the present invention provides a compound of any of formulas I-XXII wherein $R_2$ is $NHCOCH_3$. In another embodiment, the present invention provides a compound of any of formulas I-XXII wherein $R_2$ is $NHCOCF_3$. In another embodiment, the present invention provides a compound of any of formulas I-XXII wherein $R_2$ is NHCOR In another embodiment, the present invention provides a compound of any of formulas I-XXII wherein $R_2$ is alkyl. In another embodiment, the present invention provides a compound of any of formulas I-XXII wherein $R_2$ is arylalkyl. In another embodiment, the present invention provides a compound of any of formulas I-XXII wherein $R_2$ is alkenyl. In another embodiment, the present invention provides a compound of any of formulas I-XXII wherein $R_2$ is alkynyl. In another embodiment, the present invention provides a compound of any of formulas I-XXII wherein $R_2$ is OR. In another embodiment, the present invention provides a compound of any of formulas I-XXII wherein $R_2$ is $NH_2$. In another embodiment, the present invention provides a compound of any of formulas I-XXII wherein $R_2$ is NHR. In another embodiment, the present invention provides a compound of any of formulas I-XXII wherein $R_2$ is $N(R)_2$. In another embodiment, the present invention provides a compound of any of formulas I-XXII wherein $R_2$ is SR.

In one embodiment, the present invention provides a compound of any of formulas I-XXII wherein $R_3$ is F. In another embodiment, the present invention provides a compound of any of formulas I-XXII wherein $R_3$ is Cl. In another embodiment, the present invention provides a compound of any of formulas I-XXII wherein $R_3$ is Br. In another embodiment, the present invention provides a compound of any of formulas I-XXII wherein $R_3$ is I. In another embodiment, the present invention provides a compound of any of formulas I-XXII wherein $R_3$ is CN. In another embodiment, the present invention provides a compound of any of formulas I-XXII wherein $R_3$ is $NO_2$. In another embodiment, the present invention provides a compound of any of formulas I-XXII wherein $R_3$ is H. In another embodiment, the present invention provides a compound of any of formulas I-XXII wherein $R_3$ is COR. In another embodiment, the present invention provides a compound of any of formulas I-XXII wherein $R_3$ is COOH. In another embodiment, the present invention provides a compound of any of formulas I-XXII wherein $R_3$ is CONHR. In another embodiment, the present invention provides a compound of any of formulas I-XXII $R_3$ is $CF_3$. In another embodiment, the present invention provides a compound of any of formulas I-XXII wherein $R_3$ is $Sn(R)_3$. In another embodiment, the present invention provides a compound of any of formulas I-XXII wherein $R_3$ together with the benzene ring to which it is attached forms a compound represented by the structure:

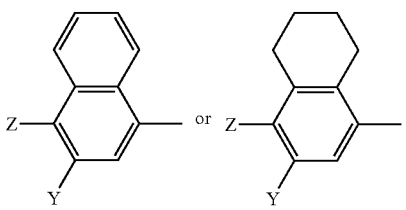

In one embodiment, the present invention provides a compound of any of formulas I-XXII wherein m is 1. In another embodiment, the present invention provides a compound of any of formulas I-XXII wherein m is 2. In another embodiment, the present invention provides a compound of any of formulas I-XXII wherein m is 3. In another embodiment, the present invention provides a compound of any of formulas I-XXII wherein n is 1. In another embodiment, the present invention provides a compound of any of formulas I-XXII wherein n is 2. In another embodiment, the present invention provides a compound of any of formulas I-XXII wherein n is 3. In another embodiment, the present invention provides a compound of any of formulas I-XXII wherein n is 4.

In one embodiment, this invention provides an analog of the compound of formula I-XXII. In another embodiment, this invention provides a derivative of the compound of formula I-XXII. In another embodiment, this invention provides a prodrug of the compound of formula I-XXII. In another embodiment, this invention provides a metabolite of the compound of formula I-XXII. In another embodiment, this invention provides a pharmaceutically acceptable salt of the compound of formula I-XXII. In another embodiment, this invention provides a pharmaceutical product of the compound of formula I-XXII. In another embodiment, this invention provides a hydrate of the compound of formula I-XXII. In another embodiment, this invention provides an N-oxide of the compound of formula I-XXII. In another embodiment, this invention provides a polymorph of the compound of formula I-XXII. In another embodiment, this invention provides a crystal of the compound of formula I-XXII. In another embodiment, this invention provides an impurity of the compound of formula I-XXII. In another embodiment, this invention provides a combination of any of an analog, derivative, metabolite, isomer, prodrug, pharmaceutically acceptable salt, pharmaceutical product, polymorph, crystal, impurity, hydrate, N-oxide of the compound of formula I-XXII.

As contemplated herein, the present invention relates to the use of a SARM compound and/or its analog, derivative, isomer, metabolite, pharmaceutically acceptable salt, pharmaceutical product, hydrate, N-oxide, polymorph, crystal, impurity or combinations thereof. In one embodiment, the invention relates to the use of an analog of the SARM compound. In another embodiment, the invention relates to the use of a derivative of the SARM compound. In another embodiment, the invention relates to the use of an isomer of the SARM compound. In another embodiment, the invention relates to the use of a metabolite of the SARM compound. In another embodiment, the invention relates to the use of a pharmaceutically acceptable salt of the SARM compound. In another embodiment, the invention relates to the use of a pharmaceutical product of the SARM compound. In another embodiment, the invention relates to the use of a hydrate of the SARM compound. In another embodiment, the invention relates to the use of an N-oxide of the SARM compound. In another embodiment, the invention relates to the use of a polymorph of the SARM compound. In another embodiment, the invention relates to the use of a crystal of the SARM compound. In another embodiment, the invention relates to the use of an impurity of the SARM compound.

As defined herein, the term "isomer" includes, but is not limited to, optical isomers and analogs, structural isomers and analogs, conformational isomers and analogs, and the like. In one embodiment, the term "isomer" is meant to encompass optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

In one embodiment, this invention encompasses the use of various optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the compounds of this invention, which may be produced, by reaction of a compound of this invention with an acid or base.

Suitable pharmaceutically-acceptable salts of amines of Formula I-V may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrate, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilate, algenate, alkane carboxylates, substituted alkane carboxylates, alginates, benzenesulfonates, benzoates, bisulfates, butyrates, bicarbonates, bitartrates, carboxilate, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonate gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoate, hydrofluorate, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, mitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, cesium; alkaline earch metals to include calcium, magnesium, aluminium; zinc, barium, cholines, quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the invention also includes N-oxides of the amino substituents of the compounds described herein. Also, esters of the phenolic compounds can be made with aliphatic and aromatic carboxylic acids, for example, acetic acid and benzoic acid esters.

This invention provides derivatives of the SARM compounds. In one embodiment, "derivatives" includes but is not limited to ether derivatives, acid derivatives, amide derivatives, ester derivatives and the like. In another embodiment, this invention further includes hydrates of the SARM compounds.

In one embodiment, "hydrate" includes but is not limited to hemihydrate, monohydrate, dihydrate, trihydrate and the like.

This invention provides, in other embodiments, metabolites of the SARM compounds. In one embodiment, "metabolite" means any substance produced from another substance by metabolism or a metabolic process.

This invention provides, in other embodiments, pharmaceutical products of the SARM compounds. The term "pharmaceutical product" refers, in other embodiments, to a composition suitable for pharmaceutical use (pharmaceutical composition), for example, as described herein.

An "alkyl" group refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. In one embodiment, the alkyl group is $CH_3$.

An "alkenyl" group refers, in another embodiment, to an unsaturated hydrocarbon, including straight chain, branched chain and cyclic groups having one or more double bond. The alkenyl group may have one double bond, two double bonds, three double bonds etc. Examples of alkenyl groups are ethenyl, propenyl, butenyl, cyclohexenyl etc. In one embodiment, the alkylene group has 1-12 carbons. In another embodiment, the alkylene group has 1-7 carbons. In another embodiment, the alkylene group has 1-6 carbons. In another embodiment, the alkylene group has 1-4 carbons. The alkenyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, in one embodiment by F, in another embodiment by Cl, in another embodiment by Br, in another embodiment by I.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system.

A "hydroxyl" group refers to an OH group. It is understood by a person skilled in the art that when T is OR, R is not OH.

In one embodiment, the term "halogen refers to in one embodiment to F, in another embodiment to Cl, in another embodiment to Br, in another embodiment to I.

An "arylalkyl" group refers, in another embodiment, to an alkyl bound to an aryl, wherein alkyl and aryl are as defined above. An example of an arylalkyl group is a benzyl group.

In one embodiment, the term "amide" refers to carbonyl group attached to an amine group. In another embodiment the amide group has the following schematic structure:

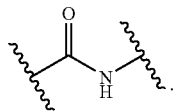

In another embodiment, the amide group is unsubstituted or substituted via the nitrogen atom by alkyl ($C_1$-$C_8$), aryl ($C_1$-$C_8$) group, phenyl, carbocyclic ($C_1$-$C_8$) group, heterocyclic ($C_1$-$C_8$) group, acyl, alkyl ($C_1$-$C_8$) halide, alkenyl ($C_1$-$C_8$) group.

In one embodiment, the term "thioamide" refers to C=S group attached to an amine group. In another embodiment the thioamide group has the following schematic structure:

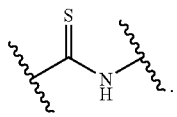

In another embodiment, the thioamide group is unsubstituted or substituted via the nitrogen atom by alkyl ($C_1$-$C_8$), aryl ($C_1$-$C_8$) group, phenyl, carbocyclic ($C_1$-$C_8$) group, heterocyclic($C_1$-$C_8$) group, acyl, alkyl ($C_1$-$C_8$) halide, alkenyl ($C_1$-$C_8$) group.

In one embodiment, the term "reverse amide" refers to amine group attached to a carbonyl group. In another embodiment the reverse amide group has the following schematic structure:

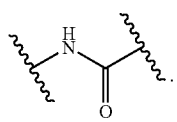

In another embodiment, the reverse amide group is unsubstituted or substituted via the nitrogen atom by alkyl ($C_1$-$C_8$), aryl ($C_1$-$C_8$) group, phenyl, carbocyclic ($C_1$-$C_8$) group, heterocyclic($C_1$-$C_8$) group, acyl, alkyl ($C_1$-$C_8$) halide, alkenyl ($C_1$-$C_8$) group.

In one embodiment, the term "reverse thioamide" refers to amine group attached to a C=S group. In another embodiment the reverse thioamide group has the following schematic structure:

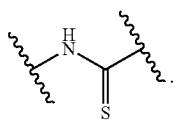

In another embodiment, the reverse thioamide group is unsubstituted or substituted via the nitrogen atom by alkyl ($C_1$-$C_8$), aryl ($C_1$-$C_8$) group, phenyl, carbocyclic ($C_1$-$C_8$) group, heterocyclic($C_1$-$C_8$) group, acyl, alkyl ($C_1$-$C_8$) halide, alkenyl ($C_1$-$C_8$) group.

In one embodiment, the term "carbamate" refers to an ester of a carbamic acid ($NH_2COOH$). In another embodiment the carbamate group has the following schematic structure:

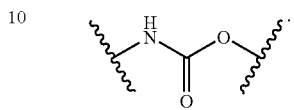

In another embodiment, the carbamate group is unsubstituted or substituted via the nitrogen atom by alkyl ($C_1$-$C_8$), aryl ($C_1$-$C_8$) group, phenyl, carbocyclic ($C_1$-$C_8$) group, heterocyclic($C_1$-$C_8$) group, acyl, alkyl ($C_1$-$C_8$) halide, alkenyl ($C_1$-$C_8$) group.

In one embodiment, the term "urea" refers to carbonyl-diamide group. In another embodiment the urea group has the following schematic structure:

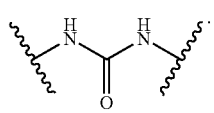

In another embodiment, the urea group is unsubstituted or substituted, independently via each or both of the nitrogen atoms by alkyl ($C_1$-$C_8$), aryl ($C_1$-$C_8$) group, phenyl, carbocyclic ($C_1$-$C_8$) group, heterocyclic($C_1$-$C_8$) group, acyl, alkyl ($C_1$-$C_8$) halide, alkenyl ($C_1$-$C_8$) group.

In one embodiment, the term "thiourea" refers to an C=S-diamide group. In another embodiment the urea group has the following schematic structure:

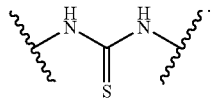

In another embodiment, the thiourea group is unsubstituted or substituted, independently via each or both of the nitrogen atoms by alkyl ($C_1$-$C_8$), aryl ($C_1$-$C_8$) group, phenyl, carbocyclic ($C_1$-$C_8$) group, heterocyclic($C_1$-$C_8$) group, acyl, alkyl ($C_1$-$C_8$) halide, alkenyl ($C_1$-$C_8$) group.

In one embodiment, the term "ester" refers to carboxylate (—CO—O—), phosphonate (PO—(OR)—O—) or to thioesters (—SO—O—) groups. In one embodiment, the term "reverse ester" refers to the reverse of the ester groups for example: —O—CO—.

In another embodiment, the present invention provides process for preparing a selective androgen receptor modulator (SARM) compound represented by the structure of formula III:

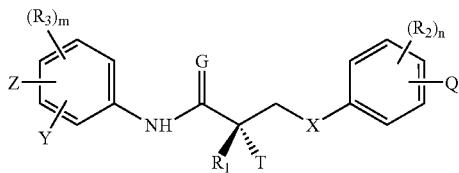

III wherein X is a bond, O, CH$_2$, NH, Se, PR, NO or NR;

G is O or S;

T is OH, OR, —NHCOCH$_3$, or NHCOR;

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;

R$_1$ is CH$_3$, CH$_2$F, CHF$_2$, CF$_3$, CH$_2$CH$_3$, or CF$_2$CF$_3$;

R$_2$ is H, F, Cl, Br, I, CH$_3$, CF$_3$, OH, CN, NO$_2$, NHCOCH$_3$, NHCOCF$_3$, NHCOR, alkyl, arylalkyl, OR, NH$_2$, NHR, N(R)$_2$, SR;

R$_3$ is H, F, Cl, Br, I, CN, NO$_2$, COR, COOH, CONHR, CF$_3$, Sn(R)$_3$, or

R$_3$ together with the benzene ring to which it is attached forms a fused ring system represented by the structure:

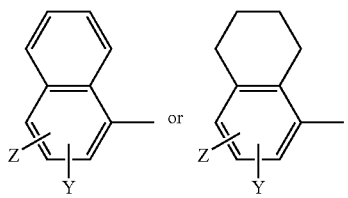

Z is NO$_2$, CN, Cl, F, Br, I, H, COR, COOH, or CONHR;

Y is CF$_3$, alkoxy, alkyl, hydroxyalkyl, alkylaldehyde, formyl, H, F, Br, Cl, I, CN, or Sn(R)$_3$;

Q is H, alkyl, halogen, CF$_3$, CN CR$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OH, OR, COR, OCOR, OSO$_2$R, SO$_2$R, SR; or Q together with the benzene ring to which it is attached is a fused ring system represented by structure A, B or C:

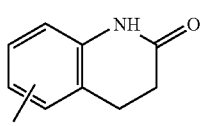

A

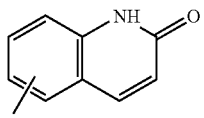

B

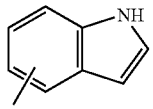

C n is an integer of 1-4; and m is an integer of 1-3;

the process comprising the step of coupling a compound of formula (10):

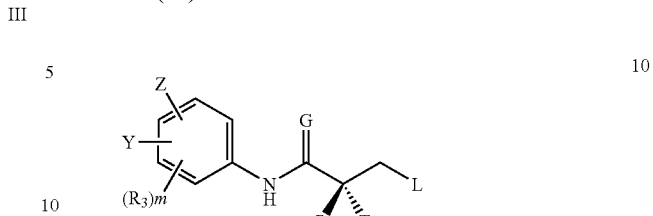

10 wherein Z, Y, G, R$_1$, T, R$_3$ and m are as defined above and L is a leaving group, with a compound of formula 11:

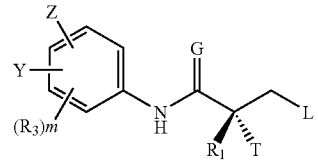

11 wherein Q, X, R$_2$ and n are as defined above.

In one embodiment, the coupling step is carried out in the presence of a base. In another embodiment, the leaving group L is Br.

In another embodiment, the compound of formula 10 is prepared by:

a) preparing a compound of formula 13 by ring opening of a cyclic compound of formula 12:

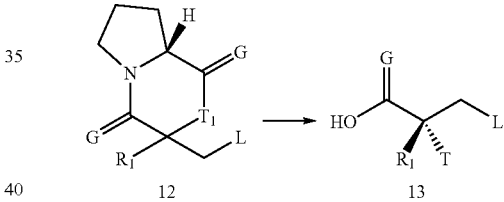

wherein L, R$_1$, G and T are as defined above, and T$_1$ is O or NH; and b) reacting an amine of formula 14:

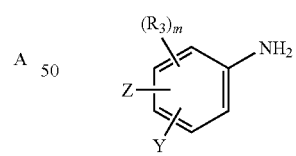

14 wherein Z, Y, R$_3$ and m are as defined above, with the compound of formula 13, in the presence of a coupling reagent, to produce the compound of formula 10.

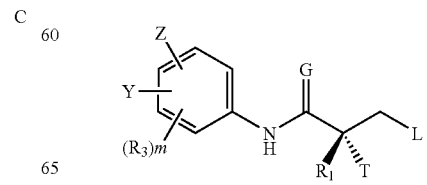

10

It is understood to a person skilled in the art that when $T_1$ is O or NH, T in compound 13 is O or $NH_2$. Thus, when T in compound 13 is OR, the reaction will involve a further step of converting the OH to OR by a reaction with, for example, an alkyl halide R—X. When T in compound 13 is NHCOR, $NHCOCH_3$, the reaction will involve a further step of converting the $NH_2$ to NHCOR or $NHCOCH_3$, by a reaction with, for example, the corresponding acyl chloride ClCOR or $ClCOCH_3$.

In one embodiment, step (a) is carried out in the presence of HBr.

In one embodiment, whereby compound 13 of step (a) is reacted with a coupling agent prior to step (b).

In one embodiment, the coupling step is carried out in the presence of a base. In another embodiment, the leaving group L is Br.

In another embodiment, the process further comprises the step of converting the selective androgen receptor modulator (SARM) compound to its analog, isomer, metabolite, derivative, pharmaceutically acceptable salt, pharmaceutical product, polymorph, crystal, impurity, N-oxide, hydrate or any combination thereof.

In another embodiment, this invention provides a large scale process for the preparation of compound of formula III, wherein the process comprises the same steps as described herein above, wherein compound of formula 12 is prepared according to the following scheme, in the presence of 4N NaOH:

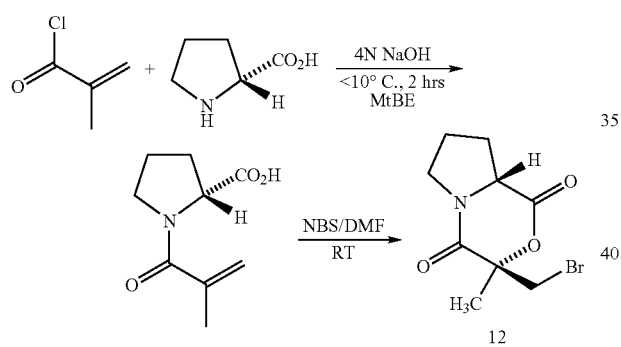

Figure 1B:
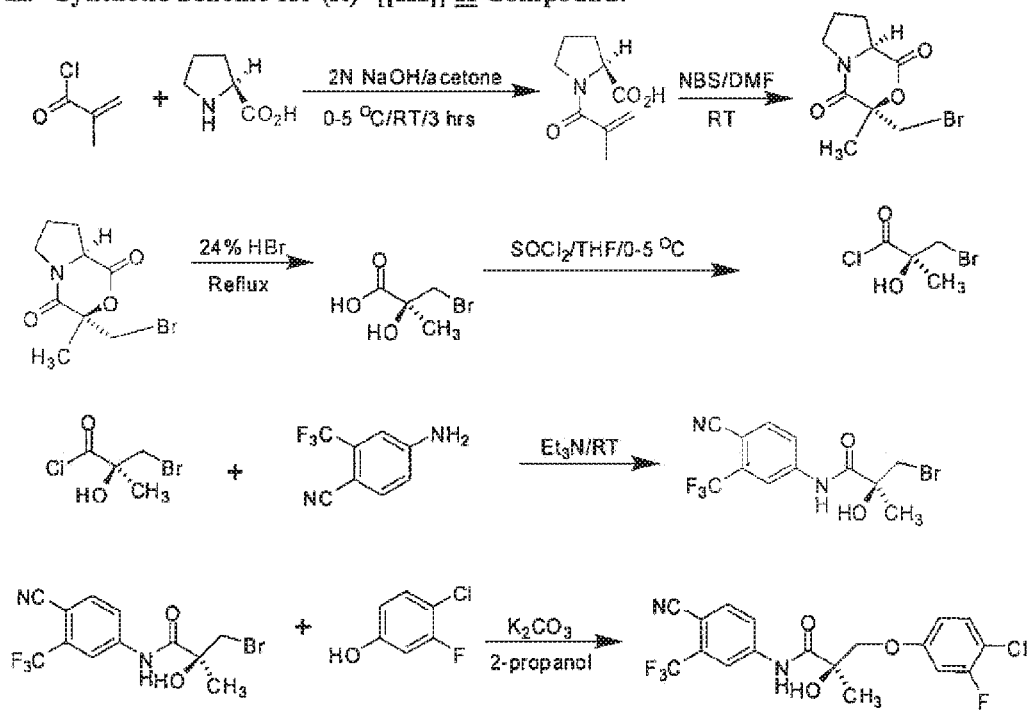
FIG. 1B is a synthetic scheme for the preparation of an (R) enantiomer of a compound of formula II (R-II).
Figure 1C:
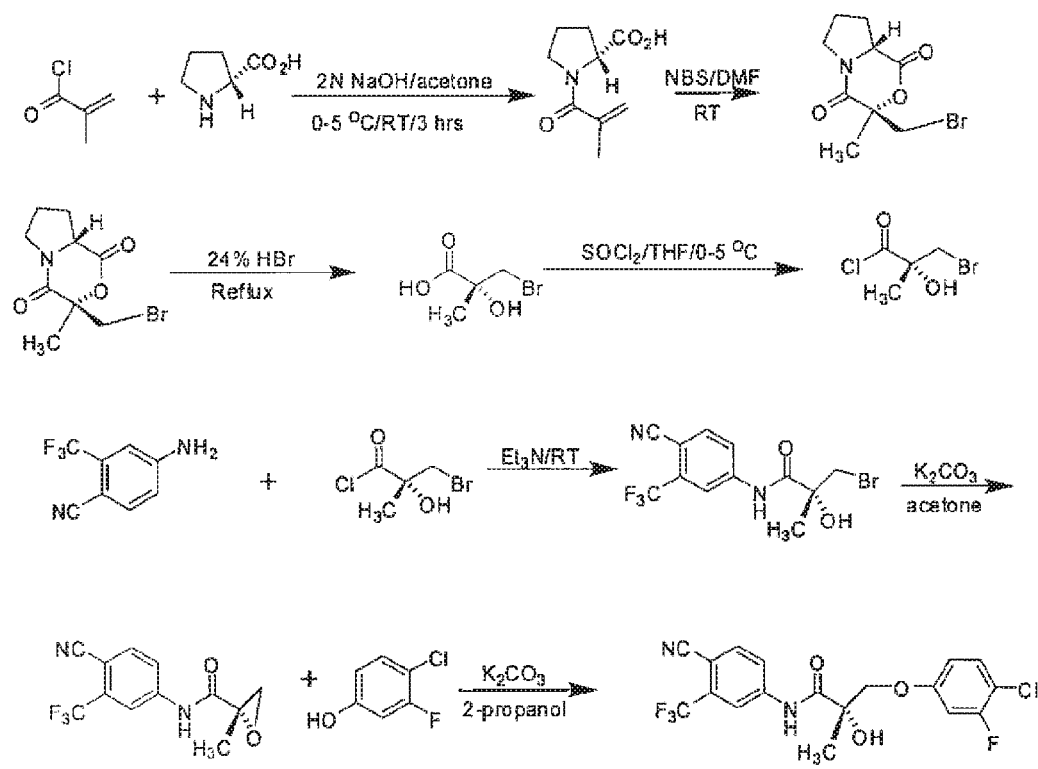
FIG. 1C is a synthetic scheme for the preparation of an (S) enantiomer of a compound of formula II (S-II) including an oxirane intermediate.
Figure 1D:
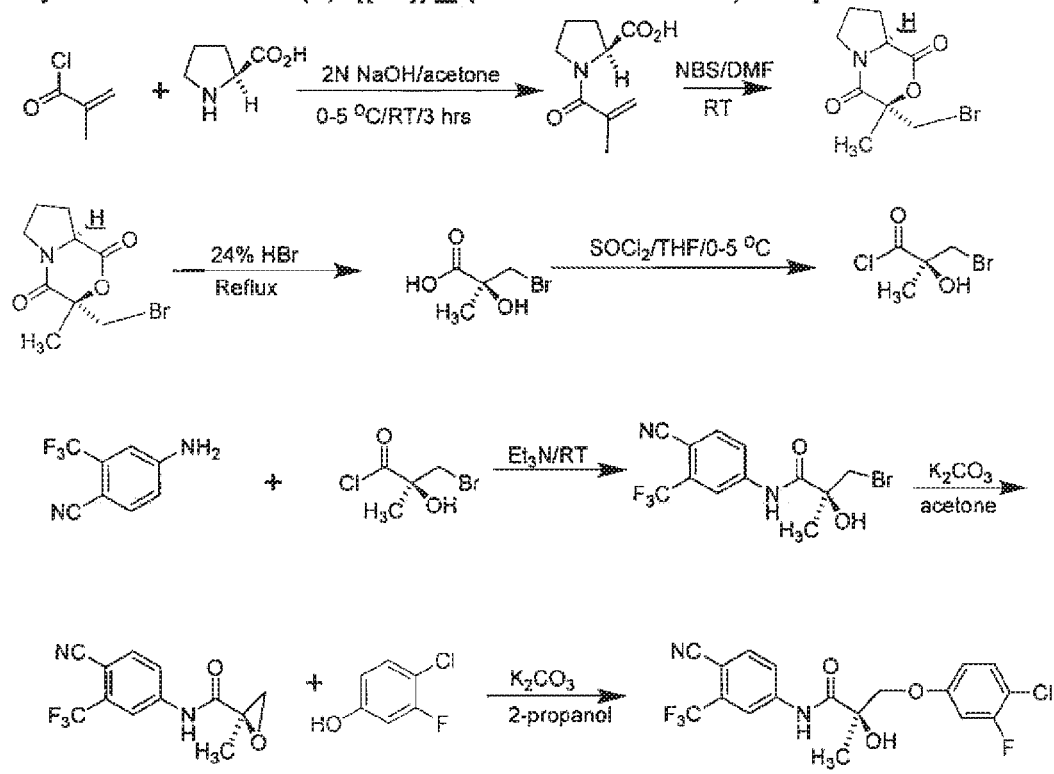
FIG. 1D is a synthetic scheme for the preparation of an (R) enantiomer of a compound of formula II (R-II) including an oxirane intermediate.
Figure 1E:
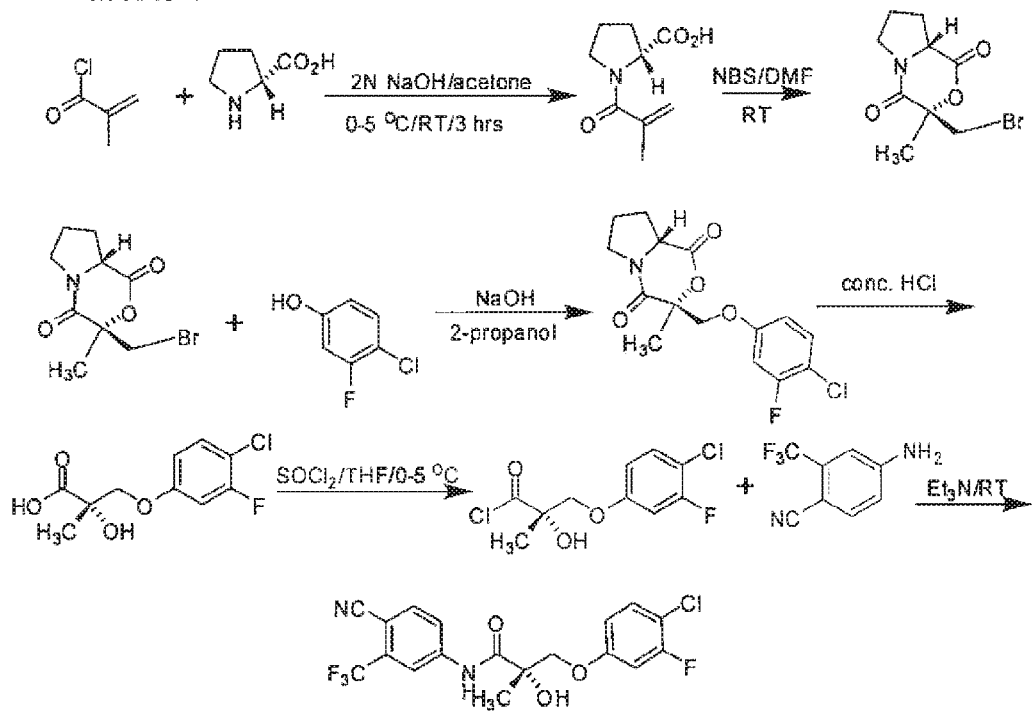
FIG. 1E is a synthetic scheme for the preparation of an (S) enantiomer of a compound of formula II (S-II) involving B-ring addition prior to A-ring addition.
Figure 1F:
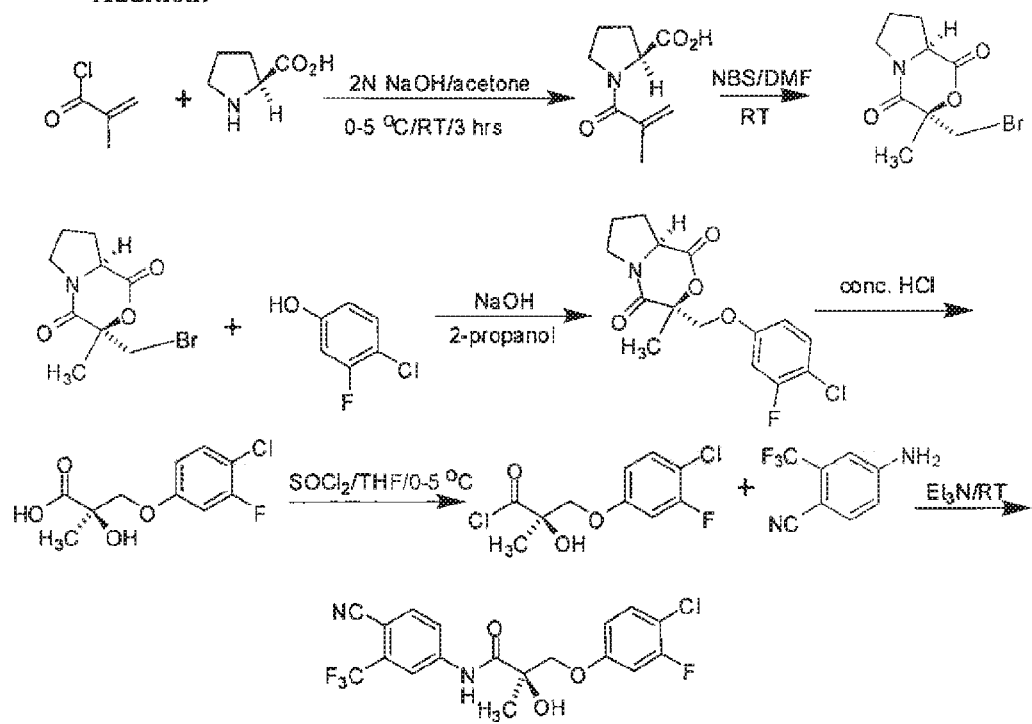
FIG. 1F is a synthetic scheme for the preparation of an (R) enantiomer of a compound of formula II (R-II) involving B-ring addition prior to A-ring addition.
Figure 1G:
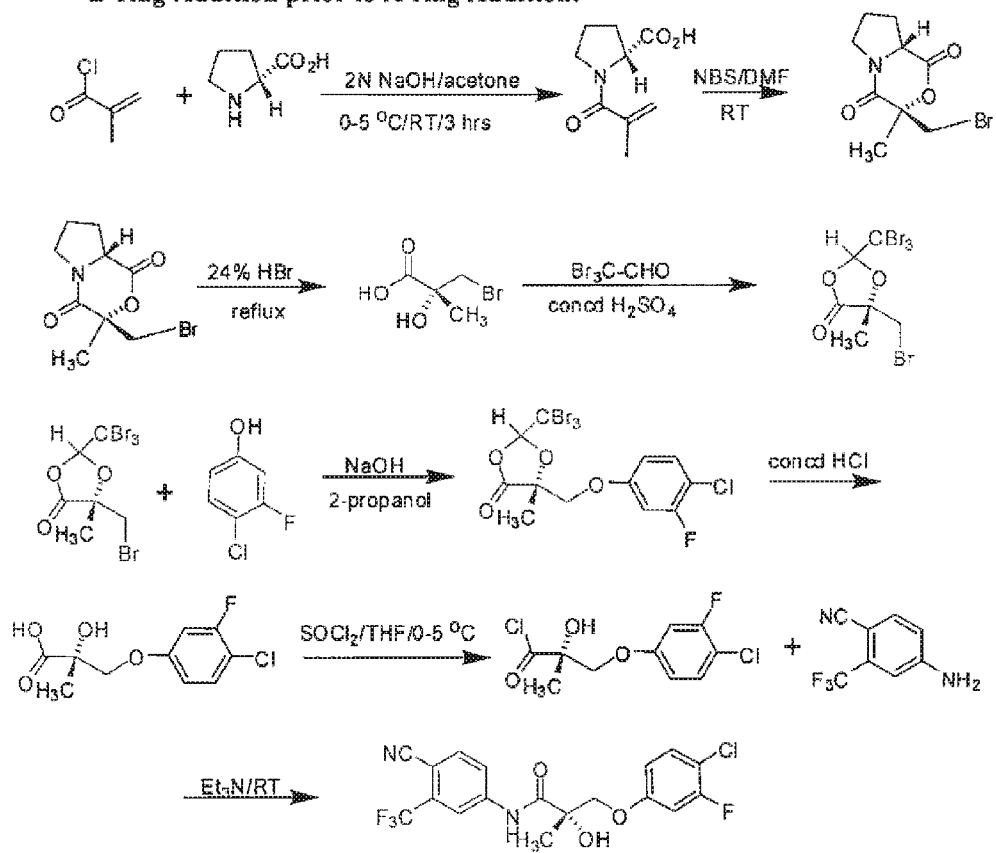
FIG. 1G is a synthetic scheme for the preparation of an (S) enantiomer of a compound of formula II (S-II) using 2-tribromomethyl-[1,3]dioxolan-4-one intermediate and involving B-ring addition prior to A-ring addition.
Figure 1H:
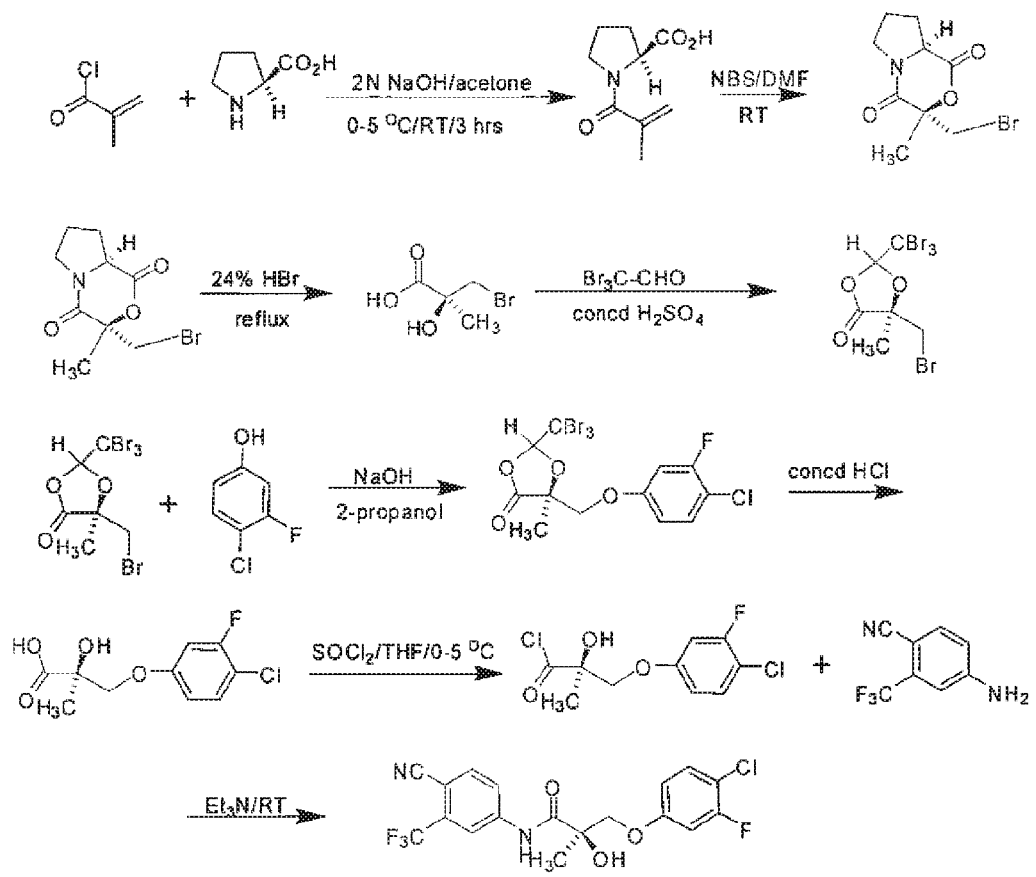
FIG. 1H is a synthetic scheme for the preparation of an (R) enantiomer of a compound of formula II (R-II) using 2-tribromomethyl-[1,3]dioxolan-4-one intermediate and involving B-ring addition prior to A-ring addition.
Figure 1J:
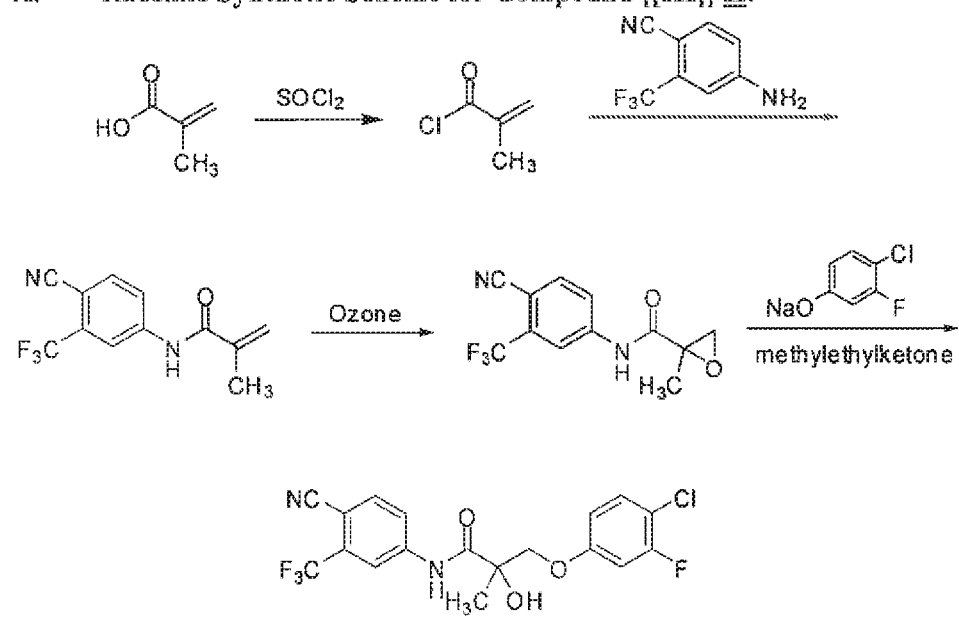
FIG. 1J is a synthetic scheme for preparation of a racemic mixture of a compound of formula II, involving an oxirane intermediate and A ring addition prior to B ring.
Figure 1K:
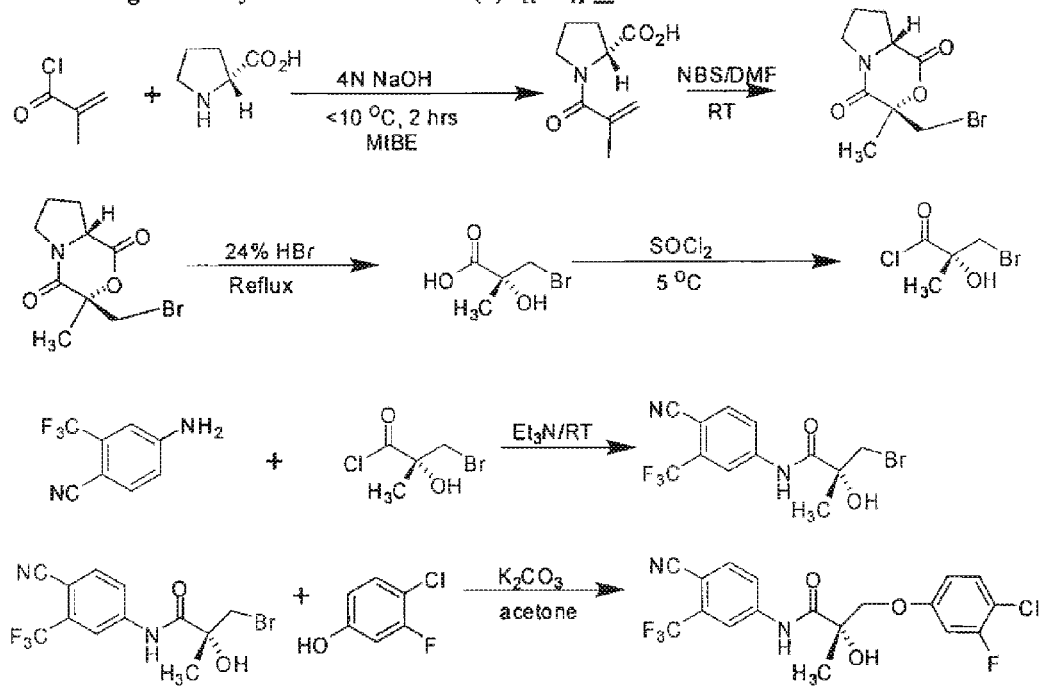
FIG. 1K is a synthetic scheme for preparation of a large scale of an (S) enantiomer of a compound of formula II (S-II).
Figure 1L:
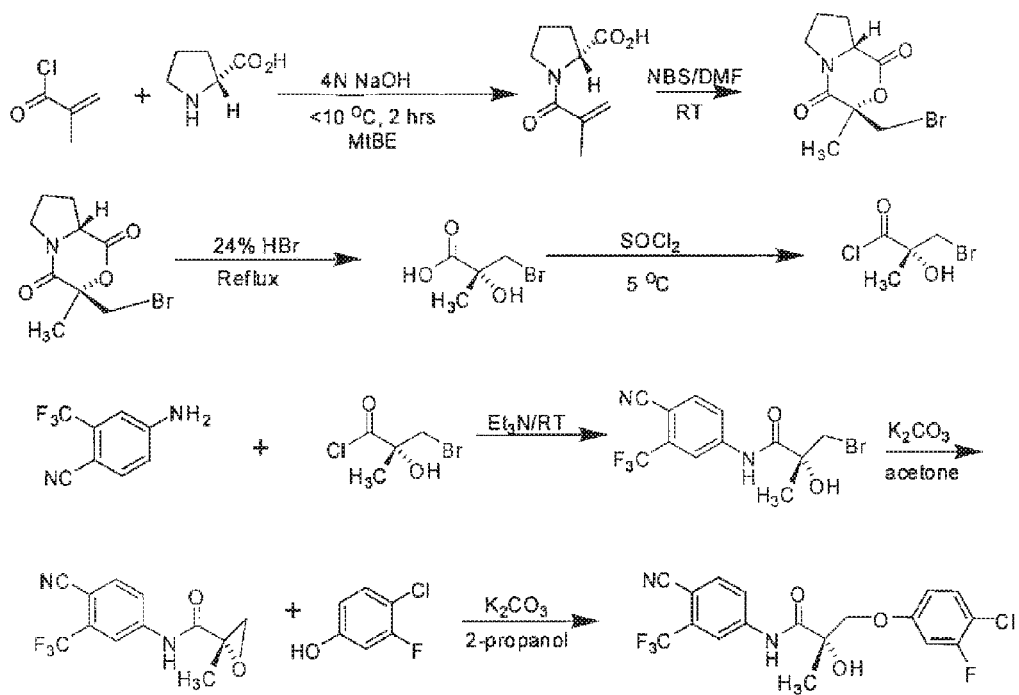
FIG. 1L is a synthetic scheme for preparation of a large scale of an (S) enantiomer of a compound of formula II (S-II), including an oxirane intermediate.

FIGS. 1K and 1L provide one embodiment of a large scale process for the preparation of a large scale synthesis of compounds of formulas S-II.

In one embodiment, the present invention provides a process for preparing a compound of formula III wherein is X is O. In another embodiment, the present invention provides a process for preparing a compound of formula III wherein is T is OH. In another embodiment, the present invention provides a process for preparing a compound of formula III wherein is $R_1$ is $CH_3$. In another embodiment, the present invention provides a process for preparing a compound of formula III wherein Z is CN, and/or Cl and/or F. In another embodiment, the present invention provides a process for preparing a compound of formula III, wherein Z is CN. In another embodiment, the present invention provides a process for preparing a compound of formula III wherein Y is $CF_3$ and/or $CH_3$, and/or H and/or Cl. In another embodiment, the present invention provides a process for preparing a compound of formula III wherein $R_3$ is H, and/or CN, and/or Cl and/or F. In another embodiment, the present invention provides a process for preparing a compound of formula III wherein Q is CN. In another embodiment, the present invention provides a process for preparing a compound of formula III wherein Q is F. In another embodiment, the present invention provides a process for preparing a compound of formula III wherein Q is Cl.

In another embodiment, the present invention provides a process for preparing a selective androgen modulator compound represented by the structure of formula I:

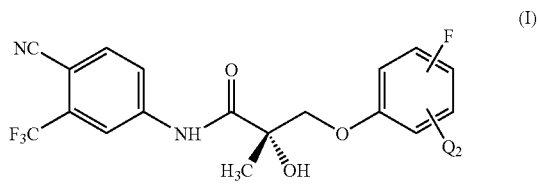

wherein $Q_2$ is hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; and R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

In another embodiment, the present invention provides a process for preparing a selective androgen modulator compound represented by the structure of formula II, as depicted in FIG. 1 and Example 1:

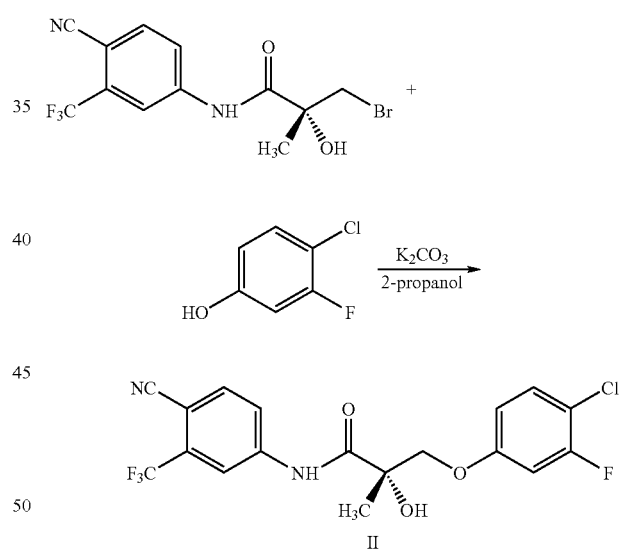

In another embodiment, the present invention provides a process for preparing an (S) enantiomer of SARM compound represented by the structure of formula II:

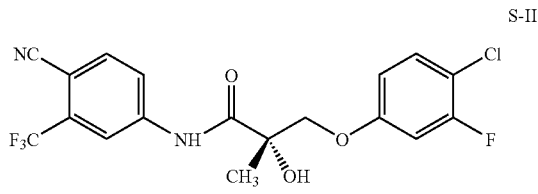

said process comprising the steps of:
a) coupling an amine of formula 17:

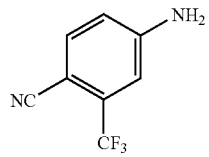

with the carboxylic acid of formula R-18

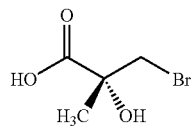

in the presence of a coupling reagent, to produce an amide of formula R-19

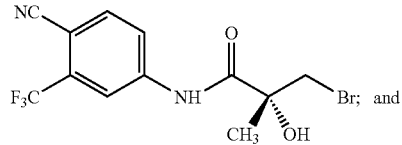

b) reacting the amide of formula R-19 with a compound of formula 20:

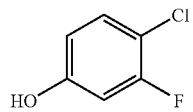

wherein Q is Cl or CN;

to produce a compound of formula S-II.

In one embodiment, whereby compound R-18 of step (a) is reacted with a coupling agent prior to addition of compound of formula 17.

FIG. 1A and Example 1 provide one embodiment of a process for the preparation of a compound of formula S-II.

In another embodiment, the conditions of step (b) of the process outlined hereinabove may comprise potassium carbonate, sodium carbonate, or cesium carbonate, or another base appropriate for this reaction, using 2-propanol, THF or methylethylketone as a solvent, optionally with a transition catalyst, BTBAC (benzyltributylammonium chloride) or other suitable agent.

In another embodiment, the present invention provides a process for preparing an (R) enantiomer of SARM compound represented by the structure of formula R-II:

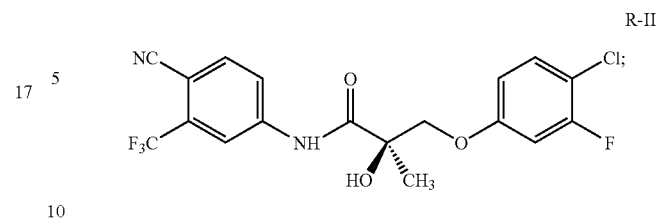

said process comprising the steps of:
a) coupling an amine of formula 17:

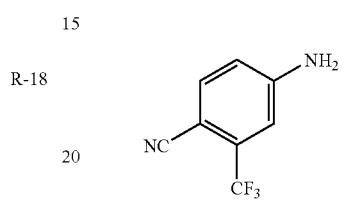

with the carboxylic acid of formula S-18

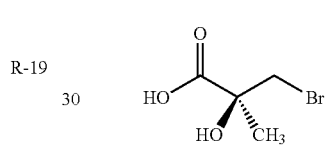

in the presence of a coupling reagent, to produce an amide of formula S-19

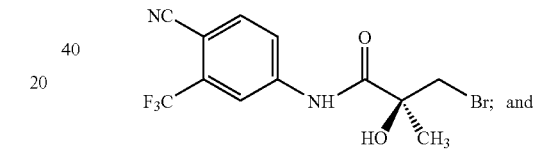

b) reacting the amide of formula S-19 with a compound of formula 20

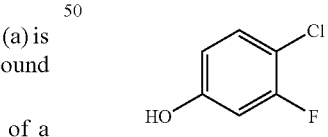

to produce a compound of R-II.

In one embodiment, whereby compound S-18 of step (a) is reacted with a coupling agent prior to addition of compound of formula 17

FIG. 1B depicts one embodiment of such a process for the preparation of compound of formula R-II.

In another embodiment, the conditions of step (b) of the process outlined hereinabove may comprise potassium carbonate, sodium carbonate, or cesium carbonate, or another base appropriate for this reaction, using 2-propanol, THF or methylethylketone as a solvent, optionally with a transition catalyst, BTBAC (benzyltributylammonium chloride) or other suitable agent.

In another embodiment, the present invention provides a process for preparing an (S) enantiomer of a SARM compound represented by the structure of formula S-II

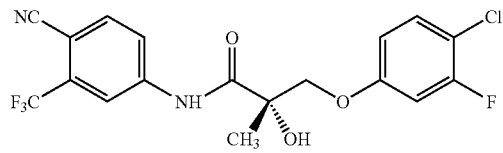
S-II said process comprising the steps of:
a) coupling an amine of formula 17:

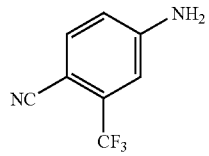
17 with the carboxylic acid of formula R-18

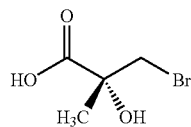
R-18 in the presence of a coupling reagent, to produce an amide of formula R-19

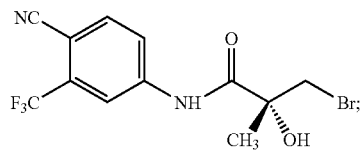
R-19 b) reacting the amide of formula R-19, with a base to form an oxirane S-21

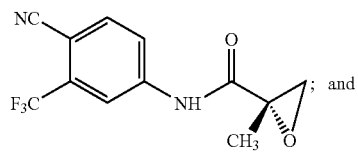
S-21 c) reacting the oxirane of formula S-21 with a compound of formula 20:

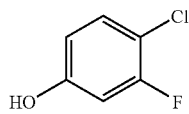
20 to produce a compound of S-II.

In one embodiment, whereby compound R-18 of step (a) is reacted with a coupling agent prior addition of compound of formula 17

FIG. 1C depicts an embodiment of such a process for the preparation of compound of formula S-II.

In another embodiment, the present invention provides a process for preparing an (R) enantiomer of SARM compound represented by the structure of formula R-II:

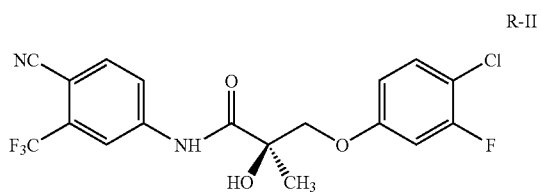
R-II said process comprising the steps of:
a) coupling an amine of formula 17:

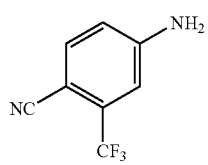
17 with the carboxylic acid of formula S-18

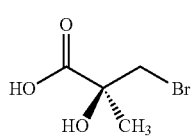
S-18 in the presence of a coupling reagent, to produce an amide of formula S-19

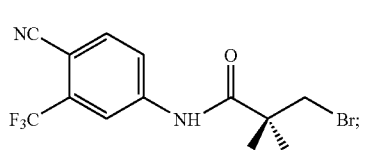
S-19 b) reacting the amide of formula S-19, with a base to form an oxirane R-21

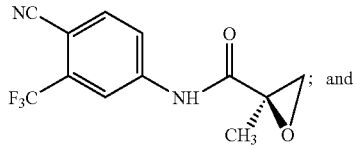

c) reacting the oxirane of formula R-21 with a compound of formula 20;

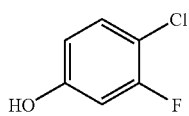

to produce a compound of R-II.

In one embodiment, whereby compound S-18 of step (a) is reacted with a coupling agent prior to addition of compound of formula 17.

FIG. 1D preparation of compound of formula R-II.

In another embodiment, the present invention provides a process for preparing an (S) enantiomer of a SARM compound represented by the structure of formula S-II.

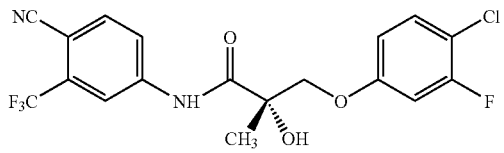

said process comprising the steps of:
a) reacting a ring of formula S-22

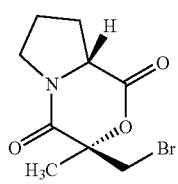

with a compound of 20

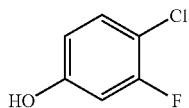

to produce a compound of formula R-23;

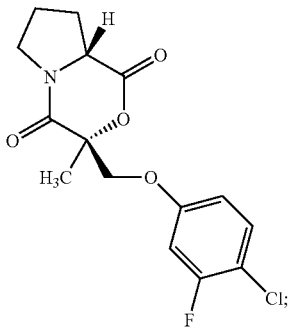

a) ring opening of compound of formula R-23 to produce a compound of formula S-24

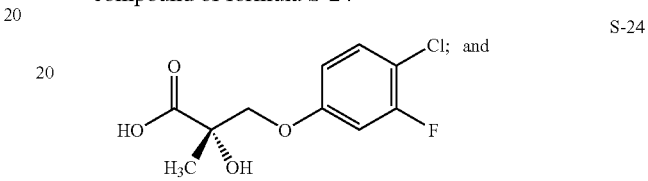

coupling the carboxylic acid of compound of formula S-24 with the amine of formula 17

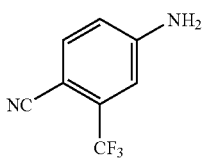

to produce the compound of formula S-II.

FIG. 1E depicts an embodiment of such a process for the preparation of compound of formula S-II.

In another embodiment, the present invention provides a process for preparing an (R) enantiomer of a SARM compound represented by the structure of formula R-II:

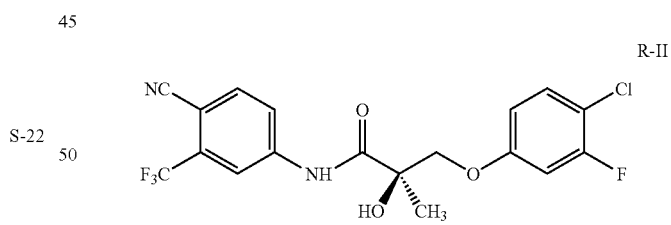

said process comprising the steps of:
a) reacting a ring of formula R-22

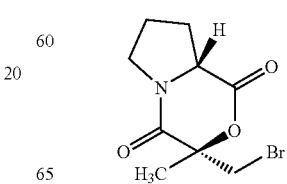

with a compound of 20

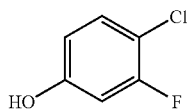

to produce a compound of formula S-23;

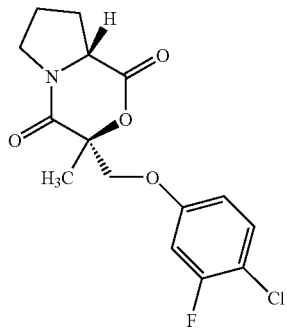

b) ring opening of compound of formula S-23 to produce a compound of formula R-24

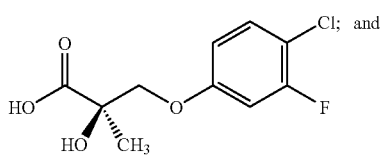

coupling the carboxylic acid of compound of formula R-24 with the amine of formula 17

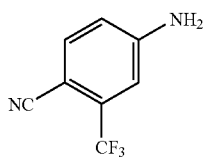

to produce the compound of formula S-III.

FIG. 1F depicts an embodiment of such a process for the preparation of compound of formula S-II.

In another embodiment, the present invention provides a process for preparing an (S) enantiomer of a SARM compound represented by the structure of formula S-II

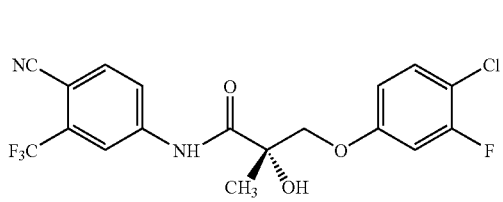

said process comprising the steps of:

a) reacting the carboxylic acid of formula R-18

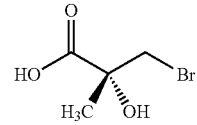

with tribromoacetaldehyde to produce a compound of formula R-25:

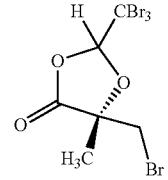

reacting the dioxalane derivative R-25 with a compound of formula 20

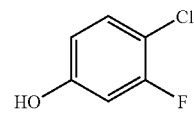

to produce a compound of formula R-26;

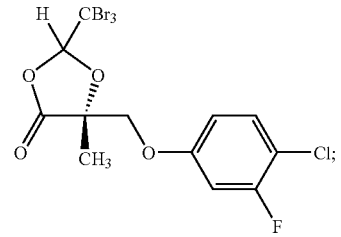

b) ring opening of compound of formula R-26 to produce a compound of formula S-24

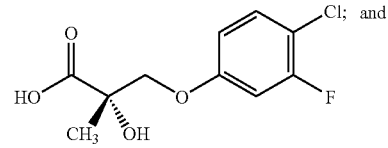

coupling the carboxylic acid of compound of formula S-24 with the amine of formula 17:

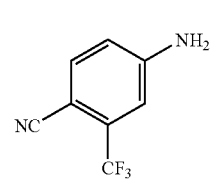

to produce the compound of formula S-II.

FIG. 1G depicts an embodiment of such a process for the preparation of compound of formula S-II.

In another embodiment, the present invention provides a process for preparing an (R) enantiomer of a SARM compound represented by the structure of formula R-II

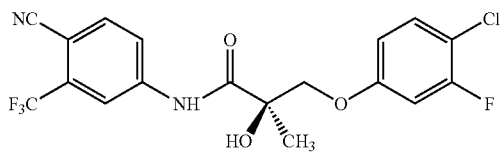
R-II said process comprising the steps of:
a) reacting the carboxylic acid of formula S-18

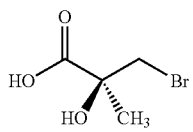
S-18 with tribromoacetaldehyde to produce a compound of formula S-25:

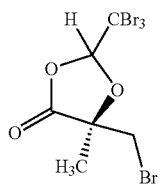
S-25 reacting the dioxalane derivative S-25 with a compound of formula 20

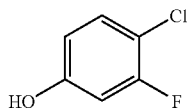
20 to produce a compound of formula S-26;

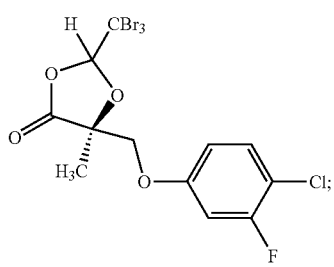
S-26 ring opening of compound of formula S-26 to produce a compound of formula R-24

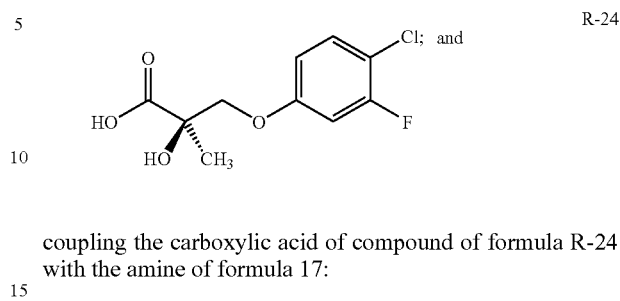
R-24 coupling the carboxylic acid of compound of formula R-24 with the amine of formula 17:

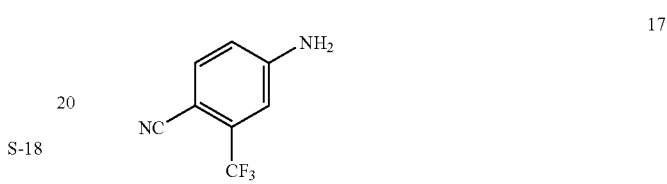
17 to produce the compound of formula R-III.

FIG. 1H depicts an embodiment of such a process for the preparation of compound of formula R-II.

In another embodiment, the present invention provides a process for preparing a racemic mixture of a SARM compound represented by the structure of formula II

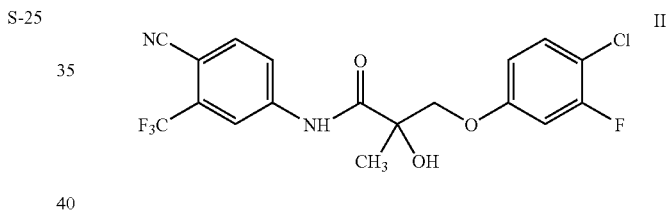
II said process comprising the steps of:
a) reacting a compound of formula 24

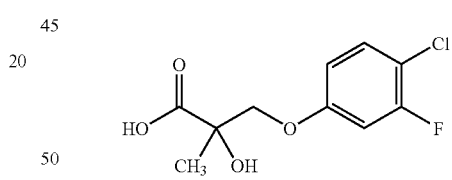
24 with a compound of formula 27

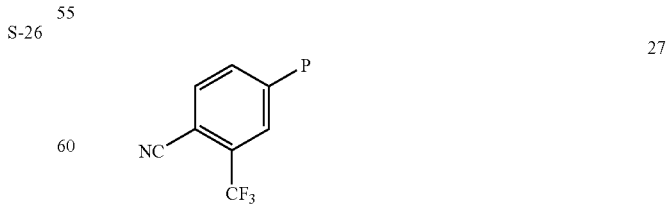
27 wherein P is selected from isocyanate (NCO) or isothiocyanate (NCS) to produce a compound of formula 28a or 28b, respectively

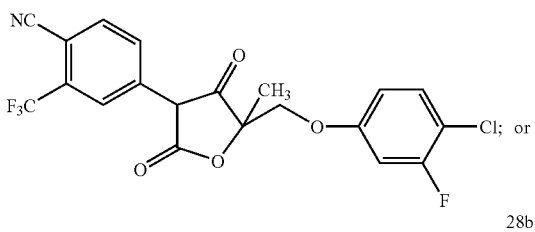

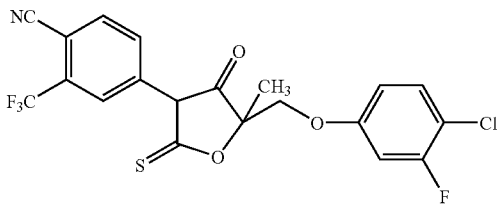

b) ring opening of the oxazolidinedione or 2-thioxooxazolid-4-one ring of formula 28a or 28b in a presence of a base to produce a compound of formula III.

FIG. 1I depicts an embodiment of such a process for the preparation of racemic compound of formula II.

In another embodiment, the present invention provides a process for preparing a racemic mixture of a SARM compound represented by the structure of formula II:

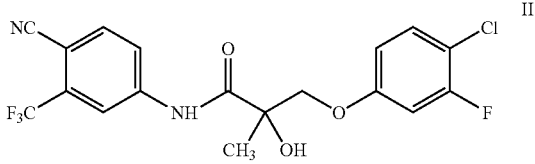

said process comprising the steps of:
a) chlorinating methacrylic acid

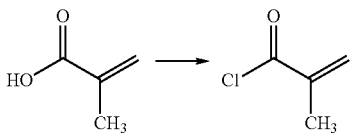

b) coupling an 3-cyano 4-trifluoromethyl aniline of formula 17 with methacryloyl chloride:

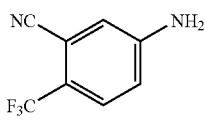

to produce the amide of formula 29.

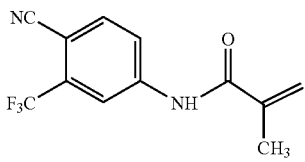

c) oxidizing an amide of formula 29, to produce the oxirane of formula 21

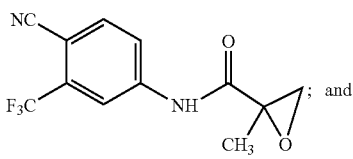

; and d) reacting the oxirane of formula 21 with a compound of formula 20

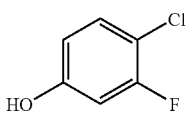

to produce the compound.

In another embodiment, the oxidizing an amide of formula 29 of step (c) comprises ozone. In another embodiment, the oxidizing agent is a peroxyacid, for example, peracetic acid, ($CH_3COOOH$). In another embodiment, the oxidizing agent meta-chloroperbenzoic acid (m-CPBA). In another embodiment, the oxidizing agent is Magnesium MonoPeroxyPthalic Acid (MMPP). In another embodiment, the oxidizing agent is hydrogen peroxide together with catalytic amounts (1.0-0.1 mol %) of manganese ($2^+$) salts.

FIG. 1J depicts an embodiment of a process for the preparation of racemic compound of formula II.

In one embodiment, this invention provides a process for preparing pure enantiomers of SARMs compounds of this invention, comprising the steps of a) preparing a racemic SARM compound of this invention; and b) separating pure SARM compound of this invention from its racemic mixture.

In one embodiment, separation of the optically-active (R) isomer or (S) enantiomer, from the racemic SARM compounds of this invention comprises crystallization techniques. In another embodiment, the crystallization techniques include differential crystallization of enantiomers. In another embodiment, the crystallization techniques include differential crystallization of diasteriomeric salts (tartaric salts or quinine salts). In another embodiment, the crystallization techniques include differential crystallization of chiral auxiliary derivatives (menthol esters, etc). In another embodiment, separation of the optically-active (R) isomer or (S) enantiomer, from the racemic SARM compounds of this invention comprises reacting the racemate mixture with another chiral group, forming of a diasteriomeric mixture followed by separation of the diasteriomers and removing the additional chiral group to obtain pure enantiomers. In another embodiment, separation of the optically-active (R) isomer or (S) enantiomer, from the racemic SARM compounds of this invention comprises chiral synthesis. In another embodiment, separation of the optically-active (R) isomer or (S) enantiomer, from the racemic SARM compounds of this invention comprises biological resolution. In another embodiment, separation of the optically-active (R) isomer or (S) enantiomer, from the racemic SARM compounds of this invention comprises enzymatic resolution. In another embodiment, separation of the optically-active (R) isomer or (S) enantiomer, from the racemic SARM compounds of this invention comprises chromatographic separation using a chiral stationary phase. In another embodiment, separation of the optically-active (R) isomer or (S) enantiomer, from the racemic SARM compounds of this invention comprises affinity chromatography. In another embodiment, separation of the optically-active (R) isomer or (S) enantiomer, from the racemic SARM compounds of this invention comprises capillary electrophoresis. In another embodiment, separation of the optically-active (R) isomer or (S) enantiomer, from the racemic SARM compounds of this invention comprises forming an ester group of the hydroxyl group of the chiral carbon with an optically-active acid, for example (−)-camphanic acid, separating the diastereomers esters, thus obtained, by fractional crystallization or preferably, by flash-chromatography, and then hydrolyzing each separate ester to the alcohol.

In another embodiment, the purity, and selectivity of an enantiomer obtained by the process of this invention, or by chiral separation of a racemic mixture of this invention can be determined by HPLC analysis.

In another embodiment, the process further comprises the step of converting the SARM compound to its analog, isomer, metabolite, derivative, pharmaceutically acceptable salt, pharmaceutical product, N-oxide, hydrate or any combination thereof.

According to this aspect of the invention, and in one embodiment, the reagent used for reacting the amide derivative, for example compound of formula 19 and the phenol derivative such as for example 20, or the compound of formula 19 with the phenol of formula 30, or the compound of formula 37 together with the compound of formula 38 are carried out in the presence of a base. Any suitable base that will deprotonate the hydrogen of the —XH moiety (for example, a phenol moiety when X is O) and allow the coupling may be used. Nonlimiting examples of bases are carbonates such as alkali carbonates, for example sodium carbonate ($Na_2CO_3$), potassium carbonate ($K_2CO_3$) and cesium carbonate ($Cs_2CO_3$); bicarbonates such as alkali metal bicarbonates, for example sodium bicarbonate ($NaHCO_3$), potassium bicarbonate ($KHCO_3$), alkali metal hydrides such as sodium hydride (NaH), potassium hydride (KH) and lithium hydride (LiH), and the like.

The leaving group L, according to this aspect, and in one embodiment, may comprise any removable group customarily considered for chemical reactions, as will be known to the person skilled in the art. Suitable leaving groups are halogens, for example F, Cl, Br and I; alkyl sulfonate esters (—$OSO_2R$) wherein R is an alkyl group, for example methanesulfonate (mesylate), trifluoromethanesulfonate, ethanesulfonate, 2,2,2-trifluoroethanesulfonate, perfluoro butanesulfonate; aryl sulfonate esters (—$OSO_2Ar$) wherein Ar is an aryl group, for example p-toluoylsulfonate (tosylate), benzenesulphonate which may be unsubstituted or substituted by methyl, chlorine, bromine, nitro and the like; $NO_3$, $NO_2$, or sulfate, sulfite, phosphate, phosphite, carboxylate, imino ester, $N_2$ or carbamate.

According to this aspect of the invention and in one embodiment, the reaction is carried out in a suitable inert solvent or diluent such as, for example, tetrahydrofuran, diethyl ether, acetone, methyl ethyl ketone, 2-propanol, aromatic amines such as pyridine; aliphatic and aromatic hydrocarbons such as benzene, toluene, and xylene; dimethylsulfoxide (DMSO), dimethylformamide (DMF), and dimethylacetamide (DMAC). In one embodiment, the reaction may be carried out in a suitable inert solvent or diluent as described hereinabove, suitably in the presence of a base such as triethylamine, and at a temperature in the range, as described above. In one embodiment, the reaction may be carried out at an appropriate temperature, as will be known to one skilled in the art, for example, in the range, of −20 to 120° C., or for example at or near ambient temperature.

The coupling reagent defined hereinabove is a reagent capable of turning the carboxylic acid/thiocarboxylic acid of formula 24 or 18 into a reactive derivative thereof, thus enabling coupling with the respective amine to form an amide/thioamide bond. A suitable reactive derivative of a carboxylic acid/thiocarboxylic acid is, for example, an acyl halide/thioacyl halide, for example an acyl/thioacyl chloride formed by the reaction of the acid/thioacid and an inorganic acid chloride, for example thionyl chloride; a mixed anhydride, for example an anhydride formed by the reaction of the acid and a chloroformate such as isobutyl chloroformate; an active ester/thioester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; an acyl/thioacyl azide, for example an azide formed by the reaction of the acid/thioacid and azide such as diphenylphosphoryl azide; an acyl cyanide/thioacyl cyanide, for example a cyanide formed by the reaction of an acid and a cyanide such as diethylphosphoryl cyanide; or the product of the reaction of the acid/thioacid and a carbodiimide such as dicyclohexylcarbodiimide.

It is to be understood that the process may comprise any embodiment described herein, as will be appropriate to produce a SARM of a corresponding formula, as will be appreciated by one skilled in the art.

In one embodiment, the process for preparing a SARM of this invention may involve ring opening in the presence of less acidic conditions, which in another embodiment, diminish the likelihood of obtaining SARM compound mixtures, and provide higher yield and purity of a SARM of interest. In one embodiment, the ring opening of a process as described herein, to produce a carboxylic acid of formula 13, is carried out in the presence of HBr, which, in one embodiment, is at a concentration of up to 30%, or in another embodiment, of up to 40%, or in another embodiment, is of up to 25%, or in another embodiment, of up to 23%, or in another embodiment, of up to between 20-25%. In one embodiment, the SARMs of this invention may be produced via large-scale synthesis, providing highly pure products in high yields.

In one embodiment, the reaction may be carried out in a suitable inert solvent or diluent as described hereinabove, suitably in the presence of a base such as triethylamine, and at a temperature in the range, as described above.

In some embodiments, the compounds as described herein are useful in preventing and treating muscle wasting disorders, bone related disorders, and diabetes related disorders.

In some embodiments, the compounds as described herein are useful, either alone or as a composition, in males and females for the treatment of a variety of hormone-related conditions, such as hypogonadism, sarcopenia, erectile dysfunction, lack of libido, osteoporosis and fertility. In some embodiments, the compounds as described herein are useful in stimulating or promoting or restoring function to various processes, which in turn result in the treatment of the conditions as herein described, including, inter aila, promoting erythropoiesis, osteogenesis, muscle growth, glucose uptake, insulin secretion, and/or preventing lipidogenesis, clotting, insulin resistance, atherosclerosis, osteoclast activity, and others.

In one embodiment, the methods of this invention make use of the described compound contacting or binding a receptor, and thereby mediating the described effects. In some embodiments, the receptor is a nuclear receptor, which in one embodiment, is an androgen receptor, or in another embodiment, is an estrogen receptor, or in another embodiment, is a progesterone receptor, or in another embodiment, is a glucocorticoid receptor. In some embodiments, the multitude of effects may occur simultaneously, as a function of binding to multiple receptors in the subject. In some embodiments, the tissue selective effects of the compounds as described herein provide for simultaneous action on different target organs.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compound of Formula I, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

The pharmaceutical compositions containing the compounds of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitonealy, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the SARM compounds are formulated in a capsule. In accordance with this embodiment, the compositions of the present invention comprise in addition to a compound of this invention and the inert carrier or diluent, a hard gelatin capsule.

In one embodiment, the micronized capsules comprise particles containing a compound of this invention, wherein the term "micronized" used herein refers to particles having a particle size is of less than 100 microns, or in another embodiment, less than 60 microns, or in another embodiment, less than 36 microns, or in another embodiment, less than 16 microns, or in another embodiment, less than 10 microns, or in another embodiment, less than 6 microns.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of a compound as herein described over a period of time. In a further embodiment, the pharmaceutical compositions are administered intravaginally.

In another embodiment, the active compound can be delivered in a vesicle, in particular a liposome (see Langer, Science 249:1627-1633 (1990); Treat et al., in Liposomes in the Therapy of Infectious Disease and Cancer, Lopez-Berestein and Fidler (eds.), Liss, New York, pp. 363-366 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In one embodiment, the compositions of this invention may include, a compound of this invention or any combination thereof, together with one or more pharmaceutically acceptable excipients.

It is to be understood that this invention encompasses any embodiment of a compound as described herein, which in some embodiments is referred to as "a compound of this invention". Such reference will include any compound, which is characterized by a structure of the formulae I-XXII, or any embodiment thereof, as described herein.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sobitan esters, stearic acids), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), coloring agents, lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the compound of this invention is released over a period of time after administration. Controlled or sustained release compositions include formulation in lipophilic depots (e.g. fatty acids, waxes, oils). In another embodiment, the composition is an immediate release composition, i.e. a composition in which all of the compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:607 (1980); Saudek et al., N. Engl. J. Med. 321: 674 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 116-138 (1984). Other controlled release systems are discussed in the review by Langer (Science 249:1627-1633 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the compounds of this invention or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the compounds of this invention or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the compound will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In one embodiment, this invention provides pharmaceutical compositions comprising a compound of this invention. In one embodiment, such compositions are useful for oral testosterone replacement therapy.

In one embodiment, this invention also provides a composition comprising two or more compounds of this invention, or polymorphs, isomers, hydrates, salts, N-oxides, etc., thereof. The present invention also relates to compositions and a pharmaceutical compositions which comprises a compound of this invention alone or in combination with a progestin or estrogen, or in another embodiment, chemotherapeutic compound, osteogenic or myogenic compound, or other agents suitable for the applications as herein described. In one embodiment, the compositions of this invention will comprise a suitable carrier, diluent or salt.

In one embodiment, the methods of this invention may comprise administration of a compound of this invention at various dosages. In another embodiment, the methods of this invention may comprise administration of a compound of formula II of this invention at various dosages In one embodiment, the compound of this invention is administered at a dosage of 0.1-200 mg per day. In one embodiment, the compound of this invention is administered at a dose of 0.1-10 mg, or in another embodiment, 0.1-26 mg, or in another embodiment, 0.1-60 mg, or in another embodiment, 0.3-16 mg, or in another embodiment, 0.3-30 mg, or in another embodiment, 0.6-26 mg, or in another embodiment, 0.6-60 mg, or in another embodiment, 0.76-16 mg, or in another embodiment, 0.76-60 mg, or in another embodiment, 1-6 mg, or in another embodiment, 1-20 mg, or in another embodiment, 3-16 mg, or in another embodiment, 30-60 mg, or in another embodiment, 30-76 mg, or in another embodiment, 100-2000 mg.

In one embodiment, the methods of this invention may comprise administration of a compound of this invention at various dosages. In another embodiment, the methods of this invention may comprise administration of a compound of formula II of this invention at various dosages In one embodiment, the compound of this invention is administered at a dosage of 1 mg. In another embodiment the compound of this invention is administered at a dosage of 6 mg, 10 mg, 16 mg, 20 mg, 26 mg, 30 mg, 36 mg, 40 mg, 46 mg, 60 mg, 66 mg, 60 mg, 66 mg, 70 mg, 76 mg, 80 mg, 86 mg, 90 mg, 96 mg or 100 mg.

In one embodiment, the present invention provides methods of use comprising the administration of a pharmaceutical composition comprising a) any embodiment of a compound as described herein; and b) a pharmaceutically acceptable carrier or diluent; which is to be understood to include an analog, isomer, metabolite, derivative, pharmaceutically acceptable salt, N-oxide, hydrate or any combination thereof of a compound as herein described, and may comprise compounds of formula II.

In some embodiments, the present invention provides methods of use of a pharmaceutical composition comprising a) any embodiment of the compounds as described herein, including an analog, isomer, metabolite, derivative, pharmaceutically acceptable salt, pharmaceutical product, N-oxide, hydrate thereof or any combination thereof; b) a pharmaceutically acceptable carrier or diluent; c) a flow-aid; and d) a lubricant.

In another embodiment, the present invention provides methods of use of a pharmaceutical composition comprising a) any embodiment of the compounds as described herein, including an analog, isomer, metabolite, derivative, pharmaceutically acceptable salt, pharmaceutical product, N-oxide, hydrate thereof or any combination thereof; b) lactose monohydrate; c) microcrystalline cellulose; d) magnesium stearate; and e) colloidal silicon dioxide.

In some embodiments, the methods of this invention make use of compositions comprising compounds of this invention, which offer the advantage that the compounds are nonsteroidal ligands for the androgen receptor, and exhibit anabolic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention, as described herein. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In some embodiments, the methods of this invention make use of compositions comprising compounds of this invention, which offer the advantage that the compounds are nonsteroidal ligands for the androgen receptor, and exhibit anabolic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In some embodiments, the compositions will further comprise a 5a-Reductase Inhibitors, a SARM or SARMs, a selective estrogen receptor modulator (SERM), an aromatase inhibitor, such as but not limited to anastrazole, exemestane, or letrozole; a GnRH agonist or antagonist, a steroidal or nonsteroidal GR ligand, a steroidal or nonsterodial PR ligand, a steroidal or nonsteroidal AR antagonist, a 17-aldoketoreductase inhibitor or 17b-hydroxysteroid dehydrogenase inhibitor. Such compositions may be used, in some embodiments, for treating a hormone dependent condition, such as, for example, infertility, neoplasia of a hormone-responsive cancer, for example, a gonadal cancer, or a urogenital cancer.

In some embodiments, the composition will comprise the compounds as described herein, as well as another therapeutic compound, including inter alia, a 5ARI such as finasteride, dutasteride, izonsteride; other SARMs, such as, RU-58642, RU-56279, WS9761 A and B, RU-59063, RU-58841, bexlosteride, LG-2293, L-245976, LG-121071, LG-121091, LG-121104, LGD-2226, LGD-2941, YM-92088, YM-175735, LGD-1331, BMS-357597, BMS-391197, S-40503, BMS-482404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, ACP-105; SERMs, such as tamoxifene, 4-hydroxytamoxifene, idoxifene, toremifene, ospemifene, droloxifene, raloxifene, arzoxifene, bazedoxifene, PPT (1,3,5-Tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERB-002, ERB-037, ERB-017, BE-1060, BE-380, BE-381, WAY-358, [18F]FEDNP, LSN-500307, AA-102, Ban zhi lian, CT-101, CT-102, VG-101; GnRH agonists or antagonists, such as, leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, acyline; FSH agonist/antagonist, LH agonist/antagonists, aromatase inhibitors, such as, letrozole, anastrazole, atamestane, fadrozole, minamestane, exemestane, plomestane, liarozole, NKS-01, vorozole, YM-511, finrozole, 4-hydroxyandrostenedione, aminogluethimide, rogletimide; Steroidal or nonsteroidal glucocorticoid receptor ligands, such as, ZK-216348, ZK-243149, ZK-243185, LGD-5552, mifepristone, RPR-106541, ORG-34517, GW-215864X, Sesquicillin, CP-472555, CP-394531, A-222977, AL-438, A-216054, A-276575, CP-394531, CP-409069, UGR-07; Steroidal or nonsterodial progesterone receptor ligands; Steroidal or nonsteroidal AR antagonists such as flutamide, hydroxyflutamide, bicalutamide, nilutamide, hydroxysteroid dehydrogenase inhibitors, PPARδ ligand such as bezafibrate, fenofibrate, gemfibrozil; PPARγ ligands such as darglitazone, pioglitazone, rosiglitazone, isaglitazone, rivoglitazone, netoglitazone; Dual acting PPAR ligands, such as naveglitazar, farglitazar, tesaglitazar, ragaglitazar, oxeglitazar, PN-2034, PPAR δ; a 17-ketoreductase inhibitors, 3β-DHΔ4, 6-isomerase inhibitors, 3β-DHΔ4,5-isomerase inhibitors, 17,20 desmolase inhibitors, p450c17 inhibitors, p450ssc inhibitors, 17,20-lyase inhibitors, or combinations thereof.

In some embodiments, the compositions will further comprise Ghrelin receptor ligand or growth hormone analogues and secretagogues, IGF-1, IGF-1 analogues and secretagogues, Myostatin Analogues, Proteasome Inhibitors, Androgenic/Anabolic Steroid, EnbrelMelanocortin 4 Receptor Agonist, Insulins, or combinations thereof. Such compositions may be used, in some embodiments, for treating sarcopenia or a musculoskeletal condition.

In some embodiments, the composition will comprise the copounds as described herein, as well as another therapeutic compound, including inter alia, Ghrelin receptor ligand or growth hormone analogues and secretagogues, such as, pralmorelin, examorelin, tabimorelin, capimorelin, capromorelin, ipamorelin, EP-01572, EP-1572, JMV-1843, an androgenic/Anabolic Steroid such as Testosterone/Oxandrolone; a melanocortin 4 receptor agonist, such as Bremelanotide, a Ghrelin or analogue thereof, such as human ghrelin, CYT-009-GhrQb, L-692429, GHRP-6, SK&F-110679, U-75799E), leptin (metreleptin, pegylated leptin; a leptin receptor agonist, such as LEP (116-130), OB3, [D-Leu4]-OB3, rAAV-leptin, AAV-hOB, rAAVhOB; an insulin (short-, intermediate-, and long acting formulations; a cortisol or corticosteroid, or a combination thereof.

The invention contemplates, in some embodiments, administration of compositions comprising the individual agents, administered separately and by similar or alternative routes, formulated as appropriately for the route of administration. The invention contemplates, in some embodiments, administration of compositions comprising the individual agents, administered in the same formulation. The invention contemplates, in some embodiments, staggered administration, concurrent administration, of administration of the various agents over a course of time, however, their effects are synergistic in the subject.

It is to be understood that any of the above means, timings, routes, or combinations thereof, of administration of two or more agents is to be considered as being encompassed by the phrase "administered in combination", as described herein.

In one embodiment, the compound of this invention is administered in combination with an anti-cancer agent. In one embodiment, the anti-cancer agent is a monoclonal antibody. In some embodiments, the monoclonal antibodies are used for diagnosis, monitoring, or treatment of cancer. In one embodiment, monoclonal antibodies react against specific antigens on cancer cells. In one embodiment, the monoclonal antibody acts as a cancer cell receptor antagonist. In one embodiment, monoclonal antibodies enhance the patient's immune response. In one embodiment, monoclonal antibodies act against cell growth factors, thus blocking cancer cell growth. In one embodiment, anti-cancer monoclonal antibodies are conjugated or linked to anti-cancer drugs, radioisotopes, other biologic response modifiers, other toxins, or a combination thereof. In one embodiment, anti-cancer monoclonal antibodies are conjugated or linked to a SARM compound as described hereinabove.

In another embodiment, the present invention includes compounds and compositions in which a compound of the invention is either combined with, or covalently bound to, an agent bound to a targeting agent, such as a monoclonal antibody (e.g., a murine or humanized monoclonal antibody). In one embodiment, the agent bound to a targeting agent is a cytotoxic agent. It will be appreciated that the latter combination may allow the introduction of cytotoxic agents into for example cancer cells with greater specificity. Thus, the active form of the cytotoxic agent (i.e., the free form) will be present only in cells targeted by the antibody. Of course, the compounds of the invention may also be combined with monoclonal antibodies that have therapeutic activity against cancer.

In one embodiment, the compound is administered in combination with a selective tyrosine kinase inhibitor. In some embodiments, the selective tyrosine kinase inhibitor inhibits catalytic sites of cancer promoting receptors thereby inhibiting tumor growth. In one embodiment, a selective tyrosine kinase inhibitor modulates growth factor signaling. In some embodiments, the selective tyrosine kinase inhibitor targets EGFR (ERB B/HER) family members. In one embodiment, the selective tyrosine kinase inhibitor is a BCR-ABL tyrosine kinase inhibitor. In one embodiment, the selective tyrosine kinase inhibitor is an epidermal growth factor receptor tyrosine kinase inhibitor. In one embodiment, the selective tyrosine kinase inhibitor is a vascular endothelial growth factor tyrosine kinase inhibitor. In one embodiment, the selective tyrosine kinase inhibitor is a Platelet Derived Growth Factor (PDGF) inhibitor.

In one embodiment, the compound is administered in combination with a cancer vaccine. In one embodiment, the cancer vaccine is a therapeutic vaccine thus, treating an existing cancer. In some embodiments, the cancer vaccine is a prophylactic vaccine thus, preventing the development of cancer. In one embodiment, both types of vaccines have the potential to reduce the burden of cancer. In one embodiment, treatment or therapeutic vaccines are administered to cancer patients and are designed to strengthen the body's natural defenses against cancers that have already developed. In one embodiment, therapeutic vaccines may prevent additional growth of existing cancers, prevent the recurrence of treated cancers, or eliminate cancer cells not killed by prior treatments. In some embodiments, prevention or prophylactic vaccines are administered to healthy individuals and are designed to target cancer in individuals who present high risk for the disease. In one embodiment, the cancer vaccine is an antigen/adjuvant vaccine. In one embodiment, the cancer vaccine is a whole cell tumor vaccine. In one embodiment, the cancer vaccine is a dendritic cell vaccine. In one embodiment, the cancer vaccine comprises viral vectors and/or DNA vaccines. In one embodiment, the cancer vaccine is an idiotype vaccine.

In one embodiment, the compound is administered in combination with an anti-cancer chemotherapeutic agent. In one embodiment, the anti-cancer chemotherapeutic agent is an alkylating agent, such as but not limited to cyclophosphamide. In one embodiment, the anti-cancer chemotherapeutic agent is a cytotoxic antibiotic such as but not limited to doxorubicin. In one embodiment, the anti-cancer chemotherapeutic agent is an antimetabolite, such as but not limited to methotrexate. In one embodiment, the anti-cancer chemotherapeutic agent is a vinca alkaloid, such as but not limited to vindesine. In some embodiments, the anti-cancer chemotherapeutic agents include platinum compounds such as but not limited to carboplatin, and taxanes such as docetaxel. In one embodiment, the anti-cancer chemotherapeutic agent is an aromatase inhibitor such as but not limited to anastrazole, exemestane, or letrozole.

In one embodiment, the compound is administered in combination with a Bax activity modulator such as alisol B acetate. In one embodiment, the compound is administered in combination with an angiotensin II receptor blocker such as losartan. In one embodiment, the compound is administered in combination with selenium, green tea cachecins, saw palmetto, lycopene, vitamin D, dietary soy, genistein or isoflavone.

In one embodiment, the compound is administered in combination with antineoplastic agents, such as alkylating agents, antibiotics, hormonal antineoplastics and antimetabolites. Examples of useful alkylating agents include alkyl sulfonates such as busulfan, improsulfan and piposulfan; aziridines, such as a benzodizepa, carboquone, meturedepa and uredepa; ethylenimines and methylmelamines such as altretamine, triethylenemelamine, triethylenephosphoramide, triethylenethiophos-phoramide and trimethylolmelamine; nitrogen mustards such as chlorambucil, chlomaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, ranimustine, dacarbazine, mannomustine, mitobronitol, mitolactol and pipobroman. More such agents will be known to those having skill in the medicinal chemistry and oncology arts.

In some embodiments, other agents suitable for combination with the compounds of this invention include protein synthesis inhibitors such as abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine, modeccin, neomycin, norvaline, pactamycin, paromomycine, puromycin, ricin, α-sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine, β-1-D-arabinoside, amethopterin, aminopterin, 2-aminopurine, aphidicolin, 8-azaguanine, azaserine, 6-azauracil, 2'-azido-2'-deoxynucliosides, 5-bromodeoxycytidine, cytosine, β-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acids, inhibitors of cell division, including colcemide, colchicine, vinblastine and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin and streptolydigin also can be combined with the compounds of the invention to provide pharmaceutical compositions.

In one embodiment, the compound is administered in combination with a vaccine for prostate cancer, Alisol B acetate, angiotensin II receptor blocker, or others known in the art. In one embodiment, the compound is administered in combination with an agent to decrease prostate (benign or malignant) hypertrophy, such as, for example, Selenium, green tea cachecins, saw palmetto, lycopene, vitamin D, dietary soy, genistein and isoflavone food product and others.

In one embodiment, the compound is administered in combination with an immunomodulating agent. In one embodiment, the immunomodulating agent is an immunosuppressive agent. In one embodiment, immunosuppressive agents comprise corticosteroids, cyclosporine, azathioprine, methotrexate, cyclophosphamide, tacrolimus —FK-506, anti-thymocyte globulin, mycophenylate moeftil, or a combination thereof. In one embodiment, the corticosteroid is a glucocorticoid.

In one embodiment, the immunomodulating agent is an immunostimulatory agent. In one embodiment, the immunostimulatory agent is a specific immunostimulator thus, provides antigenic specificity during an immune response, such as a vaccine or any antigen. In one embodiment, the immunostimulatory agent is a non-specific immunostimulator thus, acting irrespective of antigenic specificity to augment immune response of other antigen or stimulate components of the immune system without antigenic specificity. In one embodiment, the non-specific immunostimulator is Freund's complete adjuvant. In one embodiment, the non-specific immunostimulator is Freund's incomplete adjuvant. In one embodiment, the non-specific immunostimulator is a montanide ISA adjuvant. In one embodiment, the non-specific immunostimulator is a Ribi's adjuvant. In one embodiment, the non-specific immunostimulator is a Hunter's TiterMax. In one embodiment, the non-specific immunostimulator is an aluminum salt adjuvant. In one embodiment, the non-specific immunostimulator is a nitrocellulose-adsorbed protein. In one embodiment, the non-specific immunostimulator is a Gerbu Adjuvant.

In one embodiment, the compound is administered in combination with an agent, which treats bone diseases, disorders or conditions, such as osteoporosis, bone fractures, etc., and this invention comprises methods of treating the same, by administering the compounds as herein described, alone or in combination with other agents.

In one embodiment, bone turnover markers have been demonstrated as an effective, validated tool for the clinical scientist to monitor bone activity. In another embodiment, urinary hydroxyproline, serum alkaline phosphatase, tartrate-resistant acid phosphatase, and osteocalcin levels, along with the urinary calcium-creatinine ratio are used as bone turnover markers. In another embodiment osteocalcin levels is used as a bone formation marker. In another embodiment c-telopeptide is used as a bone resorption marker.

In one embodiment, this invention provides for the treatment, prevention, suppression or inhibition of, or the reduction of the risk of developing a skeletal-related event (SRE), such as bone fractures, surgery of the bone, radiation of the bone, spinal cord compression, new bone metastasis, bone loss, or a combination thereof in a subject with cancer, comprising administering to the a compound as herein described and/or its analog, derivative, isomer, metabolite, pharmaceutically acceptable salt, pharmaceutical product, hydrate, N-oxide, or any combination thereof. The invention relates, inter alia to treatment of an SRE with the compound of this invention in a subject with prostate cancer undergoing or having undergone androgen deprivation therapy (ADT).

It is to be understood that reference to "a compound of this invention", or a use thereof is to be considered to encompass use of any compound as herein described, including any embodiment thereof. It is to be considered to encompass all of compounds which may be characterized by the structure of Formulae I-XXII.

In one embodiment, the skeletal-related events treated using the methods provided herein and/or utilizing the compositions provided herein, are fractures, which in one embodiment, are pathological fractures, non-traumatic fractures, vertebral fracture, non-vertebral fractures, morphometric fractures, or a combination thereof. In some embodiments, fractures may be simple, compound, transverse, greenstick, or comminuted fractures. In one embodiment, fractures may be to any bone in the body, which in one embodiment, is a fracture in any one or more bones of the arm, wrist, hand, finger, leg, ankle, foot, toe, hip, collar bone, or a combination thereof.

In another embodiment, the methods and/or compositions provided herein, are effective in treatment, prevention, suppression, inhibition or reduction of the risk of skeletal-related events such as pathologic fractures, spinal cord compression, hypercalcemia, bone-related pain, or their combination.

In another embodiment, the skeletal-related events sought to be treated using the methods provided herein and/or utilizing the compositions provided herein, comprise the necessity for bone surgery and/or bone radiation, which in some embodiments, is for the treatment of pain resulting in one embodiment from bone damage, or nerve compression. In another embodiment, the skeletal-related events sought to be treated using the methods provided herein and/or utilizing the compositions provided herein, comprise spinal cord compression, or the necessity for changes in antineoplastic therapy, including changes in hormonal therapy, in a subject. In some embodiments, skeletal-related events sought to be treated using the methods provided herein and/or utilizing the compositions provided herein, comprise treating, suppressing, preventing, reducing the incidence of, or delaying progression or severity of bone metastases, or bone loss. In one embodiment, bone loss may comprise osteoporosis, osteopenia, or a combination thereof. In one embodiment, skeletal-related events may comprise any combination of the embodiments listed herein.

In one embodiment, the methods provided herein and/or utilizing the compositions provided herein, are effective in reducing metastases to the bone, such as in terms of number of foci, the size of foci, or a combination thereof. According to this aspect of the invention and in one embodiment, provided herein is a method of preventing or inhibiting cancer metastasis to bone in a subject, comprising the step of administering to the subject a composition comprising toremifene, raloxifene, tamoxifen or an analogue, functional derivative, metabolite or a combination thereof, or a pharmaceutically acceptable salt thereof. In one embodiment, such metabolites may comprise ospemifene, fispemifene or their combination. In one embodiment, the cancer is prostate cancer.

A person skilled in the art would readily recognize that changes in the antineoplastic therapy according to the methods provided herein, utilizing the compositions provided herein may be conducted as a function of, or adjusted or varied as a function of, inter-alia, the severity of the underlying disease, the source of the underlying disease, the extent of the patients' pain and source of the patients' pain, as well as the stage of the disease. The therapeutic changes may include in certain embodiments, changes in the route of administration (e.g. intracavitarily, intraartiarly, intratumoraly etc.), forms of the compositions administered (e.g. tablets, elixirs, suspensions etc.), changes in dosage and the like. Each of these changes are well recognized in the art and are encompassed by the embodiments provided herein.

In one embodiment, the skeletal-related events are a result of cancer therapy. In one embodiment, the skeletal-related events are a result of hormone deprivation therapy, while in another embodiment, they are a product of androgen deprivation therapy (ADT).

In one embodiment, the compounds of this invention are useful in prevention or reversal of androgen-deprivation therapy (ADT) induced side effects such as reduced muscle mass, reduced muscle strength, frailty, hypogonadism, osteoporosis, osteopenia, decreased BMD and/or decreased bone mass.

In males, while the natural decline in sex-hormones at maturity (direct decline in androgens as well as lower levels of estrogens derived from peripheral aromatization of androgens) is associated with the frailty of bones, this effect is more pronounced in males who have undergone androgen deprivation therapy.

Such agents for combined use may comprise a SERM, as herein described, a bisphosphonate, for example, alendronate, tiludroate, clodroniate, pamidronate, etidronate, alendronate, zolendronate, cimadronate, neridronate, minodronic acid, ibandronate, risedronate, homoresidronate, a calcitonin, for example, salmon, Elcatonin, SUN-8577, TJN-135; a Vitamin D or derivative (ZK-156979); a Vitamin D receptor ligand or analogues thereof, such as calcitriol, topitriol, ZK-150123, TEI-9647, BXL-628, Ro-26-9228, BAL-2299, Ro-65-2299, DP-035, an estrogen, estrogen derivative, or conjugated estrogen; an antiestrogen, progestin, synthetic estrogen/progestin; a RANK ligand mAb, for example, denosumab or AMG162 (Amgen); an αvβ3 integrin receptor antagonist; an osteoclast vacuolar ATPase inhibitor; an antagonist of VEGF binding to osteoclast receptors; a calcium receptor antagonist; PTh (parathyroid hormone) or analogues thereof, PTHrP analogues (parathyroid hormone-related peptide), Cathepsin K inhibitors (AAE581); Strontium ranelate; Tibolone; HCT-1026, PSK3471; Gallium maltolate; Nutropin AQ; Prostaglandins, p38 protein kinase inhibitor; a bone morphogenetic protein; an inhibitor of BMP antagonism, an. HMG-CoA reductase inhibitor, a Vitamin K or derivative, an antiresorptive, an Ipriflavone, a fluoride salt, dietary calcium supplement, Osteoprotegerin, or any combination thereof. In one embodiment, the combined administration of a SARM as herein described, Osteoprotegerin and parathyroid hormone is contemplated for treating any disease, disorder or condition of the bone.

In one embodiment, the immunomodulating agent is an anti-inflammatory agent. In one embodiment, the anti-inflammatory agent is a non-steroidal anti-inflammatory agent. In one embodiment, the non-steroidal anti-inflammatory agent is a cox-1 inhibitor. In one embodiment, the non-steroidal anti-inflammatory agent is a cox-2 inhibitor. In one embodiment, the non-steroidal anti-inflammatory agent is a cox-1 and cox-2 inhibitor. In some embodiments, non-steroidal anti-inflammatory agents include but are not limited to aspirin, salsalate, diflunisal, ibuprofen, fenoprofen, flubiprofen, fenamate, ketoprofen, nabumetone, piroxicam, naproxen, diclofenac, indomethacin, sulindac, tolmetin, etodolac, ketorolac, oxaprozin, or celecoxib. In one embodiment, the anti-inflammatory agent is a steroidal anti-inflammatory agent. In one embodiment, the steroidal anti-inflammatory agent is a corticosteroid.

In one embodiment, the immunomodulating agent is an anti-rheumatic agent. In one embodiment, the anti-rheumatic agent is a non-steroidal anti-inflammatory agent. In one embodiment, the anti-rheumatic agent is a corticosteroid. In one embodiment, the corticosteroid is prednisone or dexamethasone. In one embodiment, the anti-rheumatic agent is a disease modifying anti-rheumatic drug. In one embodiment, the disease modifying anti-rheumatic drug is a slow-acting anti-rheumatic drug. In one embodiment, the disease modifying anti-rheumatic drug is an antimalarial agent. In one embodiment, disease modifying anti-rheumatic drugs include but are not limited to chloroquine, hydroxychloroquine, methotrexate, sulfasalazine, cyclosporine, azathioprine, cyclophosphamide, azathioprine, sulfasalazine, penicillamine, aurothioglucose, gold sodium thiomalate, or auranofin. In one embodiment, the anti-rheumatic agent is an immunosuppressive cytotoxic drug. In one embodiment, immunosuppressive cytotoxic drugs include but are not limited to methotrexate, mechlorethamine, cyclophosphamide, chlorambucil, or azathioprine.

In one embodiment, the compound is administered in combination with an antidiabetic agent. In one embodiment, the antidiabetic agent is a sulfonylurea. In one embodiment, sulfonylureas include but are not limited to tolbutamide, acetohexamide, tolazamide, chlorpropamide, glipizide, glyburide, glimepiride, or gliclazide. In one embodiment, the antidiabetic agent is a meglitinide. In one embodiment, meglitinides include but are not limited to prandin or nateglinide. In one embodiment, the antidiabetic agent is a biguanide. In one embodiment, biguanides include but are not limited to metformin. In one embodiment, the antidiabetic agent is a thiazolidinedione. In one embodiment, thiazolidinediones include but are not limited to rosiglitazone, pioglitazone, or troglitazone. In one embodiment, the antidiabetic agent is an alpha glucosidase inhibitor. In one embodiment, alpha glucosidase inhibitors include but are not limited to miglitol or acarbose. In one embodiment, the antidiabetic agent is PPARα/γ ligand, dipeptidylpeptidase 4 (DPP-4) inhibitor, SGLT (sodium-dependent glucose transporter 1) inhibitor, or FBPase (fructose 1,6-bisphosphatase) inhibitor. In one embodiment, the antidiabetic agent is insulin. In one embodiment, the insulin is rapid-acting insulin. In one embodiment, the insulin is short-acting insulin. In one embodiment, the insulin is intermediate-acting insulin. In one embodiment, the insulin is intermediate- and short-acting insulin mixtures. In one embodiment, the insulin is long-acting insulin. In one embodiment, the antidiabetic agents are inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DPP4) inhibitors such as those disclosed in WO 0168603, which are incorporated by reference.

In one embodiment, the compound is administered in combination with an agent treating the nervous system. In one embodiment, the agent treating the nervous system is an agent treating the autonomic nervous system. In one embodiment, the agent treating the autonomic nervous system is an adrenomimetic drug. In one embodiment, the adrenomimetic drug is a beta-adrenoceptor agonist, alpha-adrenoceptor agonist, or a combination thereof. In one embodiment, the adrenomimetic drug is a catecholamine. In one embodiment, adrenomimetic drugs include but are not limited to isoproterenol, norepinephrine, epinephrine, amphetamine, ephedrine, or dopamine. In one embodiment, the adrenomimetic drug is a directly acting adrenomimetic drug. In some embodiments, directly acting adrenomimetic drugs include but are not limited to phenylephrine, metaraminol, or methoxamine.

In one embodiment, the agent treating the autonomic nervous system is an adrenoceptor antagonist. In one embodiment, the adrenoceptor antagonist is a haloalkylamine, imidazoline, or quinazoline. In one embodiment, haloalkylamines include but are not limited to phenoxybenzamine. In one embodiment, imidazolines include but are not limited to phentolamine or tolazoline. In one embodiment, quinazolines include but are not limited to prazosine, terazosin, doxazosin, or trimazosin. In one embodiment, the adrenoceptor antagonist has a combined alpha and beta blocking activity. In one embodiment, the combined alpha and beta blocking agent is labetalol, bucindolol, carvedilol, or medroxalol In one embodiment, the agent treating the autonomic nervous system is a cholinomimetic agent. In one embodiment, the cholinomimetic agent is a direct-acting parasympathomimetic drug. In one embodiment, direct-acting parasympathomimetic drugs include but are not limited to methacholine, pilocarpine, carbachol, or bethanechol.

In one embodiment, the agent treating the autonomic nervous system is a cholinesterase inhibitor. In one embodiment, the cholinesterase inhibitor is a quaternary ammonium agent. In one embodiment, quaternary ammonium agents include but are not limited to edrophonium or ambenonium. In one embodiment, the cholinesterase inhibitor is a carbamate such as physostigmine, pyridostigmine, neostigmine, or rivastigmine. In one embodiment, the cholinesterase inhibitor is an organophosphate agent. In one embodiment, the inhibitor targets acetylcholine in the central nervous system such as tacrine, donepezil, or galanthamine.

In one embodiment, the agent treating the autonomic nervous system is a muscarinic blocking agent. In one embodiment, the muscarinic blocking agent is a belladonna alkaloid such as atropine or scopolamine.

In one embodiment, the agent treating the autonomic nervous system is a gangilionic blocking agent. In one embodiment, gangilionic blocking agents include but are not limited to nicotine, trimethaphan, or mecamylamine.

In one embodiment, the agent treating the nervous system is an agent treating the central nervous system. In one embodiment, the agent treating the central nervous system is a local anesthetic agent. In one embodiment, local anesthetic agents include but are not limited to benzocaine, chloroprocaine, cocaine, procaine, bupivacaine, levobupivacaine, lidocaine, mepivacaine, prilocalne, or ropivacaine. In one embodiment, the agent treating the central nervous system is a general anaesthetic agent. In one embodiment, general anesthetic agents include but are not limited to esflurane, sevoflurane, isoflurane, halothane, enflurane, methoxyflurane, xenon, propofol, etomidate, methohexital, midazolam, diazepamor, ketamine, thiopentone/thiopental, or lidocaine/prilocalne.

In one embodiment, the agent treating the central nervous system is an analgesic agent. In some embodiments, analgesic agents include but are not limited to paracetamol or non-steroidal anti-inflammatory agent. In some embodiments, analgesic agents include opiates or morphinomimetics such as morphine, pethidine, oxycodone, hydrocodone, diamorphine, tramadol, or buprenorphine. In some embodiments, a combination of two or more analgesics is desired.

In one embodiment, the agent treating the central nervous system is a muscle relaxant or vasoconstrictor agent. In one embodiment, muscle relaxants include but are not limited to methocarbamol, baclofen, carisoprodol, chlorzoxazone, cyclobenzaprine, dantrolene, metaxalone, orphenadrine, amyl nitrite, pancuronium, tizanidine, clonidine, or gabapentin. In one embodiment, vasoconstrictor agents include but are not limited to antihistamines, adrenalin dimethylarginine, caffeine, *cannabis*, catecholamines, decongestants, pseudoephedrinse, norepinephrines, tetrahydrozoline, or thromboxane.

In one embodiment, the agent treating the central nervous system is an antiemetic drug. In one embodiment, the antiemetic drug is a 5-HT3 receptor antagonist such as dolasetron, granisetron, ondansetron, or tropisetron. In one embodiment, the antiemetic drug is a dopamine antagonist such as domperidone droperidol, haloperidol, chlorpromazine, promethazine, or metoclopramide. In one embodiment, the antiemetic drug is an antihistamine such as cyclizine, diphenhydramine, dimenhydrinate, or meclizine. In one embodiment, the antiemetic drug is a cannabinoid such as *cannabis* or marinol.

In one embodiment, the agent treating the central nervous system is a sedative agent. In one embodiment, the sedative agent is an antidepressant agent such as mirtazapine or trazodone. In one embodiment, the sedative agent is a barbiturate such as secobarbital, pentobarbital, or amobarbital. In one embodiment, the sedative agent is a benzodiazepine such as diazepam, clonazepam, alprazolam, temazepam, chlordiazepoxide, flunitrazepam, lorazepam, or clorazepate. In one embodiment, the sedative agent is an imidazopyridines such as zolpidem or alpidem. In one embodiment, the sedative agent is a Pyrazolopyrimidine such as zaleplon. In one embodiment, the sedative agent is an antihistamine such as diphenhydramine, dimenhydrinate, or doxylamine. In one embodiment, the sedative agent is an antipsychotic agent such as ziprasidone, risperidone, quetiapine, clozapine, prochlorperazine, perphenazine, loxapine, trifluoperazine, thiothixene, haloperidol, or fluphenazine. In one embodiment, the sedative agent is an herbal sedative such as valerian plant mandrake, or kava. In some embodiments, the sedative agent is eszopiclone, ramelteon, methaqualone, ethchlorvynol, chloral hydrate, meprobamate, glutethimide, methyprylon, gamma-hydroxybutyrate, ethyl alcohol, methyl trichloride, zopiclone, or diethyl ether.

In one embodiment, the agent treating the central nervous system is a neurodegenerative disorder medication. In one embodiment, the neurodegenerative disorder medication is an acetylcholinesterase inhibitor such as tacrine, donepezil, galanthamine, or rivastigmine. In one embodiment, the neurodegenerative disorder medication is an N-methyl-D-aspartate (NMDA) antagonist such as memantine. In one embodiment, the neurodegenerative disorder medication reduces damage to motor neurons such as riluzole. In one embodiment, the neurodegenerative disorder medication silences the gene that causes the progression of the disease. In one embodiment, the agent treating the central nervous system is an antiepileptic drug (AED). In some embodiments, antiepileptic agents include sodium channel blockers, GABA receptor agonists, GABA reuptake inhibitors, GABA transaminase inhibitor, AEDs with a potential GABA mechanism of action, glutamate blockers, or AEDs with other mechanisms of action. In some embodiments, antiepileptic agents include but are not limited to carbamazepine, fosphenyloin, oxcarbazepine, lamotrigine, zonisamide, clobazam, clonazepam, phenobarbital, primidone, tiagabine, vigabatrin, gabapentin, valproate, felbamate, topiramate, levetiracetam, or pregabalin.

In one embodiment, the agent treating the central nervous system is an anti-addiction drug. In one embodiment, the anti-addiction is an anti-alcoholism drug such as disulfuram.

In one embodiment, the anti-addiction drug is a serotonin uptake inhibitor, dopaminergic agonist, or opioid antagonist.

In one embodiment, the agent treating the central nervous system is an agent treating Alzheimer disease. In some embodiments, agents treating Alzheimer's disease include but are not limited to a cholinesterase inhibitor, gamma secreatse inhibitor, or a beta lowering drug.

In one embodiment, the agent treating the central nervous system is an agent treating mild cognitive impairment. In some embodiments, agents treating mild cognitive impairment include but are not limited to an AMPA regulator.

In one embodiment, the agent treating the central nervous system is an agent treating Parkinson's disease. In some embodiments, agents treating Parkinson's disease include but are not limited to a dopaminergic drugs, amantadine, benztropine, biperiden, bromocriptine, entacapone, carbidopa/levodopa, selegiline/deprenyl, iphenhydramine, pergolide, procyclidine, selegiline, or trihexyphenidyl.

In one embodiment, the compound is administered with an agent, which treats Alzheimer's disease, such as cholinesterase inhibitors, gamma secreatse inhibitors, A-beta lowering drugs; or an agent, which treats mild cognitive impairment (MCI)—such as AMPA regulators, or an agent, which treats Parkinson's Disease, such as dopaminergic drugs, or an agent, which treats Major Depression, such as SSRI's, SNRI's, for example, duloxetine, or an agent, which treats sexual dysfunction, such as PDE5 inhibitors.

In one embodiment, the compound is administered in combination with an agent treating the cardiovascular system. In one embodiment, the agent treating the cardiovascular system is treating a congestive heart failure. In one embodiment, the agent treating congestive heart failure is an angiotensin converting enzyme (ACE) inhibitor such as benazepril, captopril, cilazapril, enalapril, fosinopril, lisinopril, moexipril, perindopril, quinapril, ramipril, trandolapril, or enalaprilat. In one embodiment, the agent treating congestive heart failure is a beta-blocker such as acebutolol, atenolol, betaxolol hydrochloride, bisoprolol fumarate, carteolol hydrochloride, carvedilol, celiprolol hydrochloride, esmolol hydrochloride, labetalol hydrochloride, levobunolol, metoprolol tartrate, metipranolol, nadolol, nebivolol, oxprenolol hydrochloride, pindolol, propranolol hydrochloride, sotalol hydrochloride, or timolol maleate. In one embodiment, the agent treating congestive heart failure is digoxin. In one embodiment, the agent treating congestive heart failure is a diuretic such as thiazide diuretic, loop diuretic, potassium-sparing diuretic, or a combination thereof. In some embodiments, thiazide diuretics include but are not limited to bendrofluazide, bendroflumethiazide, benzthiazide, chlorothiazide, chlorthalidone, cyclopenthiazide, Diucardin®, Diuril®, Enduron®, Esidrix®, Exna®, HCTZ, Hydrochlorothiazide, HydroDIURIL®, HYDROFLUMETHLAZIDE, Hydromox®, Hygroton®, indapamide, Lozol®, methyclothiazide, metolazone, Mykrox®, Naqua®, Naturetin®, Oretic®, polythiazide, quinethazone, Renese®, trichlormethiazide, xipamide, or Zaroxolyn®. In some embodiments, loop diuretics include but are not limited to furosemide/frusemide, bumetanide, or torasemide. In some embodiments, potassium-sparing diuretics include but are not limited to amiloride, triamterene, aldosterone antagonists, or spironolactone.

In one embodiment, the agent treating the cardiovascular system is an anti-arrhythmic agent. In one embodiment, the anti-arrhythmic agent is a sodium channel blocker, beta-adrenergic blocker, calcium channel blocker, or an agent that prolong repolarization. In one embodiment, sodium channel blockers include but are not limited to quinidine, procainamide, disopyramidei, lidocaine, tocamide, mexiletine, encamide, or flecamide. In one embodiment, beta-adrenergic blockers include but are not limited to propranolol, acebutolol, esmolol, or sotalol. In one embodiment, agents that prolong repolarization include but are not limited to sotalol or amiodarone. In one embodiment, calcium channel blockers include but are not limited to verapamil, diltiazem, nifedipine, or mebefradil. In one embodiment, the anti-arrhythmic agent is adenosine or digoxin.

In one embodiment, the agent treating the cardiovascular system is an anti-anginal agent. In one embodiment, the anti-anginal agent is an antiplatelet agent, adrenoceptor antagonist, calcium channel blocker, or a vasodilator. In some embodiments, the adrenoceptor antagonists and calcium channel blockers comprise agents as described hereinabove. In one embodiment, the antiplatelet agent is a cyclooxygenase inhibitor, ADP inhibitor, phosphodiesterase (I) inhibitor, glycoprotein IIb/IIIa inhibitor, or an adenosine reuptake inhibitor. In one embodiment, cyclooxygenase inhibitors include but are not limited to acetylsalicylic acid or an acetylsalicylic acid in combination with dipyridimole. In one embodiment, ADP inhibitors include but are not limited to clopidogrel, CS-747, or ticlopdipine. In one embodiment, phosphodiesterase III inhibitors include but are not limited to cilostazol. In one embodiment, glycoprotein IIb/IIIa inhibitors include but are not limited to abciximab, rheopro, eptifibatide, integrilin, tirofiban, or aggrastat. In one embodiment, adenosine reuptake inhibitors include but are not limited to dipyridimole. In one embodiment, vasodilator agents include but are not limited to isosorbide dinitrate, isosorbide mononitrate, or nitroglycerine. In one embodiment, cardiac glycosides such as digitalis or ouabain may be used in combination with a SARM compound.

In one embodiment, the agent treating the cardiovascular system is a vasocative agent or an inotrope. In one embodiment, vasocative agents or inotropes include but are not limited to digoxin, dopamine, dobutamine, hydralazine, prazosin, carvedilol, nitroprusside, nitroglycerin, captopril, lisinopril, nifedipine, diltiazem, hydrochlorothiazide, furosemide, spironolactone, AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), or nitrates.

In one embodiment, the agent treating the cardiovascular system is an anticoagulant agent. In one embodiment, the anticoagulant agent is a coumarin derivative or an unfractionated heparin. In one embodiment, coumarin derivatives include but are not limited to warfarin.

In one embodiment, the agent treating the cardiovascular system is a fibrinolytic agent such as streptokinase, urokinase, alteplase, anistreplase, prourokinase, reteplase, tenecteplase, lanoteplase, staphylokinase, vampire, or alfimeprase.

In one embodiment, the agent treating the cardiovascular system is a hypercholesterolemic agent such as niacin-lovastatin, colestipol HCl, fluvastatin sodium, atorvastatin calcium, simvastatin, gemfibrozil, lovastatin, pravastatin sodium, cholestyramine, cholestyramine light, fenofibrate, colesevelam HCl, or ezetimibe.

In one embodiment, the SARM compound is administered in combination with an agent treating the gastrointestinal system. In one embodiment, the agent treating the gastrointestinal (GI) system is enhancing GI motility. In one embodiment, the agent enhancing GI motility is a prokinetic agent such as metoclopramide, cisapride, tegaserod, or erythromycin. In one embodiment, the agent treating the GI system is decreasing GI motility. In one embodiment, the agent decreasing GI motility is an opioid such as morphine, diphenoxylate, loperamide hydrochloride, or opium.

In one embodiment, the agent treating the GI system is an adsorbent or a bulking agent. In one embodiment, the adsorbent is kaolin or other hydrated aluminum silicate clays. In one embodiment, the hydrated aluminum silicate clay is further combined with pectin. In one embodiment, adsorbents or bulking agents comprise bismuth subsalicylate, methylcellulose, psyllium derivative, or calcium polycarbophil.

In one embodiment, the agent treating the GI system is a stool softener. In one embodiment, stool softeners include but are not limited to mineral oil, docusate dioctyl sodium sulfosuccinate, dioctyl calcium sulfosuccinate, or dioctyl potassium sulfosuccinate.

In one embodiment, the agent treating the GI system is a laxative. In one embodiment, the agent treating the GI system is a bulk forming laxative as described hereinabove. In one embodiment, the laxative is an osmotic laxative such as lactulose, sorbitol, or polyethylene glycol. In one embodiment, the laxative is a saline laxative such as milk of magnesia, magnesium citrate, sodium phosphate, docusate potassium, sorbitol, sodium phosphate-biphosphate, or visicoli.

In one embodiment, the agent treating the GI system is a cathartic stimulant. In one embodiment, the cathartic stimulant is an anthraquinone dervative such as cascara, aloe, senna, or rhubarb. In one embodiment, the cathartic stimulant is phenolphthalein, castor oil, or bisacodyl.

In one embodiment, the agent treating the GI system is an emetic agent. In one embodiment, the emetic agent is ipecac or apomorphine. In one embodiment, the agent treating the GI system is an anti-emetic agent such as antihistamine, anticholinergic agent, benzodiazepine, cannabinoid, dopamine antagonist, phenothiazine derivative, or 5-HT3 antagonist such as ondansetron or granisetron.

In one embodiment, the agent treating the GI system is an antacid. In one embodiment the antacid pharmaceutical preparation comprises buffering agents such as sodium bicarbonate, calcium carbonate, magnesium hydroxide, or aluminum hydroxide.

In one embodiment, the agent treating the GI system is an H2-receptor antagonist. In some embodiments, the H2-receptor antagonist is cimetidine, ranitidine, famotidine, or nizatidine.

In one embodiment, the agent treating the GI system is a proton pump inhibitor. In some embodiments, the proton pump inhibitor is omeprazole, lansoprazole, pantoprazole, rebeprazole, or esomeprazole.

In one embodiment, the agent treating the GI system is an agent treating inflammation. In one embodiment, the agent treating inflammation is 5-amino-salicylate, corticosteroid, metronidazole, ciprofloxacin, infiximab, budesonide, or anti-TNF alpha antibody.

In one embodiment, the compound is administered in combination with an agent treating a metabolic disease, disorder or condition, which in some embodiments refers to metabolic syndrome. In some embodiments, such agents comprise, inter alia, pancreatic lipase inhibitors, such as for example, orlistat, cetilistat, serotonin and norepinephrine reuptake inhibitors, such as sibutramine, insulin-sensitizers such as biguanides (metformin) or PPAR agonists, dual-acting PPAR agonists (muraglitazar, tesaglitazar, naveglitazar), PPAR-delta agonists (GW-501516), DPP-IV Inhibitors (vildagliptin, sitagliptin), alpha glucosidase inhibitors (acarbose), anti-diabetic combinations (ActoPlusMet, AvandaMet, metformin/pioglitazone, metformin/rosiglitazone, Glucovance, etc.), glucagon-like peptide-1 analogues (exenatide, liraglutide), amylin analogues (pramlintide), statins (atorvastatin, simvastatin, rosuvastatin, pravastatin, fluvastatin, lovastatin, pitavastatin), cholesterol absorption inhibitors (ezetimibe), nicotinic acid derivatives (immediate release and controlled release niacins, niaslo, etc.), antidyslipidemic fixed combinations (simvastatin/ezetimibe, lovastatin/nicotinic acid, atorvastatin/amlodipine, atorvastatin/torcetrapib, simvastatin/nicotinic acid (ER)), ACE inhibitors (ramipril, captopril, lisinopril), AT-II receptor antagonists (valsartan, telmisartan), cannabinoid receptor antagonists (rimonabant), cholesteryl ester transfer protein or CETP Inhibitors (JTT-705, CETi-1), beta3 adrenergic agonists, PPARa ligands, or combinations thereof.

In one embodiment, the compound is administered in combination with an agent treating a dermatological disorder. In one embodiment, the agent treating a dermatological disorder is a corticosteroid or glucocorticosteroid such as betamethasone dipropionate, clobetasol, diflorasone, amcinonide, desoximetasone, fluocinonide, aclometasone, desonide triamcinolone, fluticasone, halobetasol, mometasone, or hydrocortisone. In one embodiment, the agent treating a dermatological disorder is a retinoid such as isotretinoin, acitretin, tretinoin, adapalene, tazarotene, bexarotene, alitretinoin, or beta-carotene.

In one embodiment, the agent treating a dermatological disorder is photochemotherapy agent. In one embodiment, the photochemotherapy agent is PUVA or psoralen such as oxsoralen. In one embodiment, the agent treating a dermatological disorder is a photodynamic agent such as porphyrin.

In one embodiment, the agent treating a dermatological disorder is daspone, thalidomide, anti-malarial agent, antimicrobial agent, or antifungal agent. In one embodiment, the anti-malarial agent is chloroquine or hydroxychloroquine.

In one embodiment, the agent treating a dermatological disorder is an antibiotic. In one embodiment, the antibiotic is a systemic antibiotic such as griseofulvin, ketoconazole, fluconazole, itraconazole, terbinafine, or potassium iodide. In one embodiment, the antibiotic is a topical antifungal agent. In some embodiment, topical antifungal agents include but are not limited to ciclopirox, clotrimazole, econazole, ketoconazole, miconazole, naftifine, oxiconazole, terbinafine, or tolnaftate.

In one embodiment, the agent treating a dermatological disorder is an antiviral agent such as interferon alpha. In one embodiment, the agent treating a dermatological disorder is an antiscabies agent such as pyrethrin or pyrethroid. In one embodiment, the agent treating a dermatological disorder is an immunosuppressive agent such as mycophenolate motefil or 6-thioguanine. In one embodiment, the agent treating a dermatological disorder is a topical immunosuppressive agent such as tacrolimus, pimecrolimus, imiquimod, 5-fluorouracil, or mechlorethamine. In one embodiment, the agent treating a dermatological disorder is an antihistamine such as doxepin. In one embodiment, the agent treating a dermatological disorder is treating pigmentation such as hydroquinone or monobenzone. In one embodiment, the agent treating a dermatological disorder is a protein or a recombinant protein such as becaplermin, etanercept, denileukin diftitox, or botulinum toxin. In one embodiment, the agent treating a dermatological disorder is capsaicin, anthralin, benzoyl peroxide, or calcipotriene.

In one embodiment, the agent treating a dermatological disorder is a keratolytic agent. In one embodiment, the agent treating a dermatological disorder is selenium sulfide. In one embodiment, the agent treating or preventing a dermatological disorder is a sunscreen. In one embodiment, the sunscreen absorbs UVB, UVA, or a combination thereof.

In one embodiment, the agent treating a dermatological disorder may be a growth factor such as epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (β-FGF), transforming growth factor-β (TGF-β) and insulin like growth factors (IGF-1 and IGF-2), or any combination thereof.

In one embodiment, the compound is administered in combination with an anti-infective agent. In one embodiment, the anti-infective agent is an antibiotic agent. In one embodiment the antibiotic is a beta-lactam antibiotic. In one embodiment beta-lactam antibiotics include but are not limited to penicillin, benzathine penicillin, benzylpenicillin, amoxicillin, procaine penicillin, dicloxacillin, amoxicillin, flucloxacillin, ampicillin, methicillin, aziocillin, carbenicillin, ticarcillin, mezlocillin, piperacillin, phenoxymethylpenicillin, co-amoxiclav, cephalosporin, cefalexin, cephalothin, cefazolin, cefaclor, cefuroxime, cefamandole, cefotetan, cefoxitin, ceftriaxone, cefotaxime, ceftazidime, cefepime, cefpirome, imipenem, meropenem, ertapenem, faropenem, monobactam, aztreonam, or carbapenem.

In one embodiment the antibiotic is a tetracycline antibiotic. In one embodiment tetracycline antibiotics include but are not limited to tetracycline, chlortetracycline, demeclocycline, doxycycline, lymecycline, minocycline, or oxytetracycline.

In one embodiment the antibiotic is a macrolide antibiotic. In one embodiment macrolide antibiotics include but are not limited to erythromycin, azithromycin, oxithromycin, dirithromycin, clarithromycin, josamycin, oleandomycin, kitasamycin, spiramycin, tylosin/tylocine, troleandomycin, carbomycin, cethromycin, or telithromycin.

In one embodiment the antibiotic is an aminoglycoside antibiotic. In one embodiment, aminoglycoside antibiotics include but are not limited to gentamicin, tobramycin, faropenem, imipenem, kanamycin, neomycin, ertapenem, apramycin, paromomycin sulfate, streptomycin, or amikacin.

In one embodiment the antibiotic is a quinolone antibiotic. In one embodiment quinolone antibiotics include but are not limited to ciprofloxacin, norfloxacin, lomefloxacin, enoxacin, ofloxacin, ciprofloxacin, levofloxacin, sparfloxacin, gatifloxacin, moxifloxacin, trovafloxacin, or alatrofloxacin.

In one embodiment the antibiotic is a cyclic peptide antibiotic. In one embodiment cyclic peptide antibiotics include but are not limited to vancomycin, streptogramins, Microcin J25, Bacteriocin AS-48, RTD-1, or polymyxins.

In one embodiment the antibiotic is a lincosamide antibiotic. In one embodiment lincosamide antibiotics include but are not limited to clindamycin.

In one embodiment, the antibiotic is an oxazolidinone antibiotic. In one embodiment oxazolidinone antibiotics include but are not limited to linezolid, U-100592, DA-7867, AZD2563, or U-100766.

In one embodiment, the antibiotic is a sulfa antibiotic. In one embodiment, sulfa antibiotics include but are not limited to sulfisoxazole.

In one embodiment, the antibiotic is an antiseptic agent. In one embodiment, antiseptic agents include but are not limited to alcohols, chlorhexidine, chlorine, hexachlorophene, iodophors, chloroxylenol (PCMX), quaternary ammonium compounds, or triclosan.

In one embodiment, the antibiotic is an anti-tuberculosis agent. In one embodiment an anti-tuberculosis agents include but are not limited to ethambutol, rifabutin, isoniazid, rifampicin, pyrazinamide, or rifampin In one embodiment, the antibiotic is an antifungal agent. In one embodiment, antifungal agents include but are not limited to terbinafine, flucytosine, fluconazole, itraconazole, ketoconazole, ravuconazole, posaconazole, voriconazole, caspofungin, micafungin, v-echinocandin, amphotericin B, amphotericin B lipid complex (ABLC), amphotericin B colloidal dispersion (ABCD), liposomal amphotericin b (l-Amb), liposomal nystatin, or griseofulvin.

In one embodiment, the antibiotic is an antiprotozoal agent. In one embodiment the antiprotozoal agent is an antimalarial agent. In one embodiment, antimalarial agents include but are not limited to chloroquine, mefloquine, proguanil, pyrimethamine with dapsone, pyrimethamine with sulfadoxine, quinine, or primaquine. In one embodiment, the antiprotozoal agent is an amoebicide. In one embodiment, amoebicides include but are not limited to metronidazole, timidazole, or diloxanide furoate. In one embodiment, the antiprotozoal agent is an antigiadial agent. In one embodiment, antigiadial agents include but are not limited to metronidazole, timidazole, or mepacrine. In one embodiment, the antiprotozoal agent is a leishmanicide. In one embodiment, leishmanicides include but are not limited to sodium stibogluconate. In one embodiment, the antibiotic is an antithelmintic agent.

In one embodiment, the antibiotic is an antiviral agent. In one embodiment, antiviral agents include but are not limited to abacavir, acyclovir, amantadine, didanosine, emtricitabine, enfuvirtide, entecavir, lamivudine, nevirapine, oseltamivir, ribavirin, rimantadine, stavudine, valaciclovir, vidarabine, zalcitabine, or zidovudine. In one embodiment, the antiviral agent is a nucleotide analog reverse transcriptase inhibitor. In one embodiment, nucleotide analog reverse transcriptase inhibitors include but are not limited totenofovir or adefovir. In one embodiment, the antiviral agent is a protease inhibitor. In one embodiment, protease inhibitors include but are not limited to saquinavir, ritonavir, indinavir, nelfinavir, amprenavir, lopinavir, fosamprenavir, or tipranavir. In one embodiment, the antiviral agent is a fusion inhibitor such as enfuvirtide. In one embodiment, a combination of antiviral or antiretroviral agents is desired. In one embodiment, antiviral or antiretroviral agents or a combination thereof, further comprise hydroxyurea, resveratrol, grapefruit, ritonavir, leflunomide, or a combination thereof.

In one embodiment, the compound is administered in combination with an agent treating the liver. In one embodiment, the compound is administered in combination with a statin. In some embodiment, statins include but are not limited to atorvastatin, fluvastatin, lovastatin, pravastatin, simvastatin, or rosuvastatin.

In one embodiment, the compound is administered in combination with a bile acid sequestrant. In some embodiment, bile acid sequestrants include but are not limited to cholestyramine, colestipol, or colesevelam.

In one embodiment, the compound is administered in combination with a cholesterol absorption inhibitor. In some embodiment, cholesterol absorption inhibitors include but are not limited to ezetimibe.

In one embodiment, the compound is administered in combination with a nicotinic acid agent. In some embodiments, nicotinic acid agents include but are not limited to niacin, niacor, or sloniacin.

In one embodiment, the compound is administered in combination with a fibrate. In some embodiments, fibrates include but are not limited to gemfibrozil, or fenofibrate.

In one embodiment, the agent treating the liver is cortisone, cortisol or corticosterone. In some embodiments, the agent treating the liver is colchicine, methotrexate, ursodeoxycholic acid, or penicillamine.

In one embodiment, the compound is administered in with an agent treating the kidney. In one embodiment, the agent treating the kidney is a diuretic. In some embodiments, diuretics include but are not limited to organomercurial, ethacrynic acid, frusemide, humetanide, piretanide, muzolimine, chlorothiazide and thiazide, phthalimidine, chlorthalidone, clorexolone, quinazolinone, quinethazone, metolazone ilenzenesulphonamide, mefruside, chlorobenzamide, clopamidesalicylamide, xipamide, xanthine, aminophylline, carbonic anhydrase inhibitor, acetazolamide mannitol, potassium-sparing compound, aldosterone antagonist, spironolactone and canrenoate, pteridines, pyrazine, carboxamide-triamterene, or amiloride. In one embodiment, the agent treating the kidney is a steroid.

In one embodiment, the agent treating the kidney is erythropoietin. In one embodiment, erythropoietin is obtained by natural sources (e.g., urinary erythropoietin; See U.S. Pat. No. 3,865,801), or is a recombinantly produced protein and analogs thereof, for example, as described in U.S. Pat. Nos. 5,441,868, 5,547,933, 5,618,698 and 5,621,080 as well as human erythropoietin analogs with increased glycosylation and/or changes in the amino acid sequence as those described in European Patent Publication No. EP 668351 and the hyperglycosylated analogs having 1-14 sialic acid groups and changes in the amino acid sequence described in PCT Publication No. WO 91/05867. In one embodiment, erythropoietin-like polypeptides are administered in combination with the compounds of this invention. In some embodiments, erythropoietin-like polypeptides comprise darbepoietin (from Amgen; also known as Aranesp and novel erthyropoiesis stimulating protein (NESP)).

In one embodiment, the SARM compound is administered in with an agent treating a metabolic disease. In some embodiments, agents treating a metabolic disease include but are not limited to a vitamin, Coenzyme Q10, glucosidase alfa, sodium bicarbonate, bisphosphonate, biotin, allopurinol, levodopa, diazepam, phenobarbital, haloperidol, folic acid, antioxidants, activators of cation channels haptoglobin, or carnitine.

In one embodiment, the agent treating a metabolic disease is a pancreatic lipase inhibitor such as orlistat or cetilistat, Serotonin or norepinephrine reuptake inhibitor such as sibutramine, insulin-sensitizers such as biguanide, PPAR agonist, Dual-acting PPAR agonist such as muraglitazar, tesaglitazar, or naveglitazar, PPAR-delta agonist such as GW-501516, DPP-IV Inhibitor such as vildagliptin or sitagliptin, alpha glucosidase inhibitor such as acarbose, antidiabetic combination such as ActoPlusMet, AvandaMet, metformin/pioglitazone, metformin/rosiglitazone, or Glucovance, Glucagon-like peptide-1 analogue such as exenatide or liraglutide, Amylin analogue such as pramlintide, statin such as atorvastatin, simvastatin, rosuvastatin, pravastatin, fluvastatin, lovastatin, or pitavastatin, Cholesterol absorption inhibitor such as ezetimibe, Nicotinic acid derivative such as niacin or niaslo, antidyslipidemic fixed combination such as simvastatin/ezetimibe, lovastatin/nicotinic acid, atorvastatin/amlodipine, or atorvastatin/torcetrapib, simvastatin/nicotinic acid, ACE inhibitor such as ramipril, captopril, or lisinopril, AT-II receptor antagonist such as valsartan or telmisartan, cannabinoid receptor antagonist such as rimonabant, cholesteryl ester transfer protein or CETP Inhibitor such as JTT-705, CETi-1, or beta-3 adrenergic agonist.

In one embodiment, the compound is administered with an agent treating a wasting disease. In some embodiments, agents treating a wasting disease include but are not limited to corticosteroids, anabolic steroids, cannabinoids, metoclopramid, cisapride, medroxyprogesterone acetate, megestrol acetate, cyproheptadine, hydrazine sulfate, pentoxifylline, thalidomide, anticytokine antibodies, cytokine inhibitors, eicosapentaenoic acid, indomethacin, ibuprofen, melatonin, insulin, growth hormone, clenbuterol, porcine pancreas extract, IGF-1, IGF-1 analogue and secretagogue, myostatin analogue, proteasome inhibitor, testosterone, oxandrolone, enbrel, melanocortin 4 receptor agonist, or a combination thereof.

In one embodiment, the agent treating a wasting disease is a ghrelin receptor ligand, growth hormone analogue, or a secretagogue. In some embodiments, ghrelin receptor ligands, growth hormone analogues, or secretagogues include but are not limited to pralmorelin, examorelin, tabimorelin, capimorelin, capromorelin, ipamorelin, EP-01572, EP-1572, or JMV-1843.

In one embodiment, growth promoting agents such as but not limited to TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890 are utilized as agents treating a wasting disease.

In other embodiments, agents treating a wasting disease may comprise growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or, in other embodiments, with growth hormone releasing factor and its analogs or growth hormone and its analogs, or with alpha-adrenergic agonists, such as clonidine or serotinin 5-HTD agonists, such as sumatriptan, or agents which inhibit somatostatin or its release, such as physostigmine and pyridostigmine. In some embodiments, agents treating a wasting disease may comprise parathyroid hormone, PTH (1-34) or bisphosphonates, such as MK-217 (alendronate). In other embodiments, agents treating wasting disease may further comprise estrogen, a selective estrogen receptor modulator, such as tamoxifene or raloxifene, or other androgen receptor modulators, such as those disclosed in Edwards, J. P. et. al., Bio. Med. Chem. Let., 9, 1003-1008 (1999) and Hamann, L. G. et. al., J. Med. Chem., 42, 210-212 (1999). In some embodiments, agents treating a wasting disease may further comprise a progesterone receptor agonists ("PRA"), such as levonorgestrel, medroxyprogesterone acetate (MPA). In some embodiments, agents treating a wasting disease may include nutritional supplements, such as those described in U.S. Pat. No. 5,179,080, which, in other embodiments are in combination with whey protein or casein, amino acids (such as leucine, branched amino acids and hydroxymethylbutyrate), triglycerides, vitamins (e.g., A, B6, B 12, folate, C, D and E), minerals (e.g., selenium, magnesium, zinc, chromium, calcium and potassium), carnitine, lipoic acid, creatinine, B-hyroxy-B-methylbutyriate (Juven) and coenzyme Q. In one embodiment, agents treating a wasting disease may further comprise antiresorptive agents, vitamin D analogues, elemental calcium and calcium supplements, cathepsin K inhibitors, MMP inhibitors, vitronectin receptor antagonists, Src SH2 antagonists, vacular-H+-ATPase inhibitors, ipriflavone, fluoride, fibolone, prostanoids, 17-beta hydroxysteroid dehydrogenase inhibitors and Src kinase inhibitors.

In one embodiment, the compound is administered in with an agent treating the endocrine system. In some embodiments, agents treating the endocrine system include but are not limited to radioactive iodine, antithyroid agent, thyroid hormone supplement, growth hormone, cabergoline, bromocriptine, thyroxine, gonadotropin, glucocorticoid, glucocorticoid analogue, corticotrophin, metyrapone, aminoglutethimide, mitotane, ketoconazole, mifepristone, dexamethasone somatostatin analogue, gonadotropin-releasing hormone analogue, leuprolide, goserelin, antidiuretic hormone, antidiuretic hormone analogue, oxytocin, calcium supplement, vitamin D, or a combination thereof.

In one embodiment, the agent treating the endocrine system is a 5-alpha-reductase inhibitor. In some embodiments, 5-alpha-reductase inhibitors include but are not limited to finasteride, dutasteride, or izonsteride.

In one embodiment, the agent treating the endocrine system is a SARM compound. In some embodiments, SARMs include but are not limited to RU-58642, RU-56279, WS9761 A and B, RU-59063, RU-58841, bexlosteride, LG-2293, L-245976, LG-121071, LG-121091, LG-121104, LGD-2226, LGD-2941, YM-92088, YM-175735, LGD-1331, BMS-357597, BMS-391197, S-40503, BMS-482-404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, or ACP-105.

In one embodiment, the additional agent treating the endocrine system is a SERM compound. In some embodiments, SERMs include but are not limited to tamoxifene, 4-hydroxytamoxifene, idoxifene, toremifene, ospemifene, droloxifene, raloxifene, arzoxifene, bazedoxifene, PPT (1,3,5-Tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, Ban zhi lian, CT-10, CT-102, or VG-101.

In one embodiment, the agent treating the endocrine system is a gonadotropin-releasing hormone agonist or antagonist. In some embodiments, gonadotropin-releasing hormone agonists or antagonists include but are not limited to leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, or acyline.

In one embodiment, the agent treating the endocrine system is a luteinizing hormone agonist or antagonist. In some embodiments, luteinizing hormone agonists or antagonists include but are not limited to letrozole, anastrazole, atamestane, fadrozole, minamestane, exemestane, plomestane, liarozole, NKS-01, vorozole, YM-511, finrozole, 4-hydroxyandrostenedione, aminogluethimide, or rogletimide. In one embodiment, the agent treating the endocrine system is a follicle stimulating hormone agonist or antagonist. In one embodiment, the agent treating the endocrine system is a luteinizing hormone releasing hormone (LHRH) or a LHRH analog.

In one embodiment, the agent treating the endocrine system is a steroidal or nonsteroidal glucocorticoid receptor ligand. In some embodiments, nonsteroidal glucocorticoid receptor ligands include but are not limited to ZK-216348, ZK-243149, ZK-243185, LGD-5552, mifepristone, RPR-106541, ORG-34517, GW-215864×, Sesquicillin, CP-472555, CP-394531, A-222977, AL-438, A-216054, A-276575, CP-394531, CP-409069, or UGR-07.

In one embodiment, the agent treating the endocrine system is a steroidal or non-steroidal progesterone receptor ligand. In one embodiment, the agent treating the endocrine system is a steroidal or nonsteroidal androgen receptor antagonist. In some embodiments, steroidal or nonsteroidal androgen receptor antagonists include but are not limited to flutamide, hydroxyflutamide, bicalutamide, nilutamide, or hydroxysteroid dehydrogenase inhibitor.

In one embodiment, the agent treating the endocrine system is a peroxisome proliferator-activated receptor ligand. In some embodiments, peroxisome proliferator-activated receptor ligands include but are not limited to bezafibrate, fenofibrate, gemfibrozil, darglitazone, pioglitazone, rosiglitazone, isaglitazone, rivoglitazone, netoglitazone, naveglitazar, farglitazar, tesaglitazar, ragaglitazar, oxeglitazar, or PN-2034.

In one embodiment, an agent treating the endocrine system is a human growth hormone. In some embodiments, human growth hormones include but are not limited to somatotropin or analogues.

In one embodiment, the agent treating the endocrine system is a ghrelin. In some embodiments, ghrelins include but are not limited to human ghrelin, CYT-009-GhrQb, L-692429, GHRP-6, SK&F-110679, or U-75799E.

In one embodiment, the agent treating the endocrine system is a leptin. In some embodiments, leptins include but are not limited to metreleptin or pegylated leptin. In one embodiment, an agent treating the endocrine system is a leptin receptor agonist. In some embodiments, leptin receptor agonists include but are not limited to LEP (116-130), OB3, [D-Leu4]-OB3, rAAV-leptin, AAV-hOB, or rAAVhOB.

In one embodiment, the SARM compound is administered with an inhibitor of an enzyme involved in the androgen biosynthetic pathway. In some embodiments, inhibitors of enzymes involved in the androgen biosynthetic pathway include but are not limited to 17-ketoreductase inhibitor, 3-DH4,6-isomerase inhibitor, 3-DH4,5-isomerase inhibitor, 17,20 desmolase inhibitor, p450c17 inhibitor, p450ssc inhibitor, or 17,20-lyase inhibitor.

In one embodiment, the SARM compound is administered with an agent treating osteoporosis. In some embodiments, osteoporosis is induced by alcohol and/or smoking. In some embodiments, agents treating osteoporosis include but are not limited to SERMs, calcitonin, vitamin D, vitamin D derivatives, vitamin D receptor ligand, vitamin D receptor ligand analogue, estrogen, estrogen derivative, conjugated estrogen, antiestrogen, progestin, synthetic estrogen, synthetic progestin, RANK ligand monoclonal antibody, integrin receptor antagonist, osteoclast vacuolar ATPase inhibitor, antagonist of VEGF binding to osteoclast receptors, calcium receptor antagonist, parathyroid hormone, parathyroid hormone analogue, parathyroid hormone-related peptide, cathepsin K inhibitor, strontium ranelate, tibolone, HCT-1026, PSK3471, gallium maltolate, nutropin AQ, prostaglandin, p38 protein kinase inhibitor, bone morphogenetic protein (BMP), inhibitor of BMP antagonism, HMG-CoA reductase inhibitor, vitamin K, vitamin K derivative, ipriflavone, fluoride salts, dietary calcium supplement, or osteoprotegerin.

In one embodiment, the agent treating osteoporosis is a calcitonin. In some embodiments, calcitonins include but are not limited to salmon, elcatonin, SUN-8577, or TJN-135.

In one embodiment, the agent treating osteoporosis is a vitamin D receptor ligand or analogue. In some embodiments, vitamin D receptor ligands or analogues include but are not limited to calcitriol, topitriol, ZK-150123, TEI-9647, BXL-628, Ro-26-9228, BAL-2299, Ro-65-2299, or DP-035.

In one embodiment, the SARM compound is administered with an agent treating pharmacotherapy induced hypogonadal and/or osteopenic and/or sarcopenic state. In some embodiments, agents treating pharmacotherapy induced hypogonadal and/or osteopenic and/or sarcopenic states include but are not limited to opioids, narcotics, opiates, opioids, methadone, kadian, D2 dopamine receptor antagonist, zotepine, haloperidol, amisulpride, risperidone, anti-epileptic agent, valproic acid, carbamazepine, oxcarbamazepine, chemotherapeutic agent, methotrexate, cyclophosphamide, ifosfamide, adriamycin, doxorubicin, glucocorticoids, cyclosporine, L-thyroxine, SERMs, AI, fulvestrant, gonadotropin-releasing hormone agent, androgen depravation agent, prolactinemia-inducing agent, serotonergic antidepressant, selective serotonin reuptake inhibitor, monoamine oxidase inhibitor, tricyclic antidepressant, antihypertensive agents, methyldopa, reserpine, clonidine, verapamil, antidopaminergic agent, anti-emetic agent, metoclopramide, H2 receptor antagonist, cimetidine, ranitidine, estrogen, or amphetamine.

In one embodiment, the compound of this invention is administered with a vitamin. In some embodiments, vitamins include but are not limited to vitamin D, vitamin E, vitamin K, vitamin B, vitamin C, or a combination thereof.

In one embodiment, the compound of this invention is administered with a behavior-modulating agent. In some embodiments, behavior-modulating agents include but are not limited to an anti-anxiety agent, anti-psychotic agent, anti-depressant, beta-blocker, beta-2 agonist, anticholinergic bronchodilator, theophylline, aminophylline, nedocromil sodium, sodium cromoglycate, leukotriene receptor antagonist, corticosteroid, expectorant, mucolytic agent, antihistamine, pseudoephedrine, methylphenidate, amphetamine, buspirone, benzodiazepine, dextroamphetamine, tricyclic antidepressant, serotonin reuptake inhibitor, phenothiazines, benztropine, bupropion, propranolol, lithium, venlafaxine, haloperidol, buspirone, or a neuraminidase inhibitor.

In one embodiment, the behavior-modulating agent is a benzodiazepine. In one embodiment, benzodiazepines comprise alprazolam, chlordiazepoxide, diazepam, flurazepam, lorazepam, oxazepam, temazepam, or triazolam.

In one embodiment, the behavior-modulating agent is a phenothiazine. In one embodiment, phenothiazines comprise fluphenazine, perphenazine, thioridazine, or trifluoperazine.

In one embodiment, the behavior-modulating agent is a tricyclic antidepressant or a serotonin reuptake inhibitor. In one embodiment, tricyclic antidepressants or serotonin reuptake inhibitors comprise phenothiazine, protriptyline, fluoxetine, paroxetine, or sertraline.

In one embodiment, the compound of this invention is administered with an agent treating a connective tissue. In some embodiments, agents treating a connective tissue include but are not limited to an anti-malaria agent, a cytotoxic agent, a steroid, corticosteroid, lupus medication, imuran, cytoxan, anti-rheumatic agent, corticosteroid, nifedipine, aspirin, coichicine, captopril, penicillamine, azathioprine, methotrexate, cyclophosphamide, prednisone, nicardipine, or a non-steroidal anti-inflammatory agent.

In one embodiment, the compound of this invention is administered with an agent treating an ophthalmic disease. In some embodiments, agents treating an ophthalmic disease include but are not limited to betagan, betimol, timoptic, betoptic, betoptic, ocupress, optipranolol, xalatan, alphagan, azopt, trusopt, cospot, pilocar, pilagan, propine, opticrom, acular, livostin, alomide, emadine, patanol, alrex, poly-pred, pred-g, dexacidin, erythromycin, maxitrol, tobradex, blephamide, FML, ocufen, voltaren, profenal, pred forte, econpred plus, eflone, flarex, inflamase forte, betadine, gramicidin, prednisolone, betaxolol, humorsol, proparacaine, betoptic, hylartin, inflamase mild, lotemax, flurbiprofen, chloramphenicol, methazolamide, timolol, ciloxan, terramycin, ciprofloxacin, miostat, triamcinolone, miconazole, tobramycin, physostimine, gentamicin, pilocarpine, bacitracin, goniosol, polymyxin, oxytetracycline, viroptic, vexol, suprofen, celluvisc, polytrim, illotycin, ciloxan, ocuflox, brinzolamide, cefazolin, tobrex, latanoprost, indocyanine, trifluridine, phenylephrine, demecarium, neomycin, tropicamide, dexamethasone, neptazane, dipivefrin, ocuflox, vidarabine, dorzolamide, ofloxacin, epinephrine, acyclovir, carbonic anhydrase inhibitor, antihistamine vitamin A, vitamin C, vitamin E, zinc, copper, atropine, or garamycin.

In one embodiment, the compound of this invention is administered in with a gene therapy agent. In some embodiments, gene therapy agents include but are not limited to an antisense agent, or a replacement gene.

In some embodiments, any of the compositions of this invention will comprise a compound of formula I, in any form or embodiment as described herein. In some embodiments, any of the compositions of this invention will consist of a compound of formula I, in any form or embodiment as described herein. In some embodiments, of the compositions of this invention will consist essentially of a compound of I, in any form or embodiment as described herein. In some embodiments, the term "comprise" refers to the inclusion of the indicated active agent, such as the compound of formula I, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, alone or as part of the combined therapy or using the compositions of this invention represent additional embodiments of this invention.

Biological Activity of Selective Androgen Modulator Compounds

The compounds of this invention may be useful, in some embodiments, for oral testosterone replacement therapy. In other embodiments, appropriately substituted compounds are useful for a) male contraception; b) treatment of a variety of hormone-related conditions, for example conditions associated with ADAM, such as fatigue, depression, decreased libido, sexual dysfunction, erectile dysfunction, hypogonadism, osteoporosis, hair loss, obesity, sarcopenia, osteopenia, benign prostate hyperplasia, and alterations in mood and cognition; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; e) treatment of prostate cancer, imaging of prostate cancer; decreasing the incidence of, halting or causing a regression of prostate cancer; f) treatment of diabetes type I; g) treatment of diabetes type II; h) suppressing or inhibiting or reducing the incidence of diabetes i) treatment of glucose intolerance; j) treatment of hyperinsulinemia; k) treatment of insulin resistance l) treatment of diabetic nephropathy; m) treatment of diabetic neuropathy; n) treatment of diabetic retinopathy; o) treatment of fatty liver condition; p) treatment of cachexia; q) oral androgen replacement and/or other clinical therapeutic and/or diagnostic areas, including any embodiment of what is encompassed by the term "treating" as described herein.

In some embodiments, the compounds of this invention possess in vivo tissue selective androgenic and anabolic activity, which is accordingly utilized for particular applications, as will be appreciated by one skilled in the art.

In one embodiment, this invention provides: a) a method of treating a subject having a muscle wasting disorder; b) a method of treating a subject suffering from malnutrition; c) a method of treating a bone-related disorder in a subject; d) a method of increasing a bone mass in a subject; e) a method of improving the lipid profile in a subject; f) a method of treating atherosclerosis and its associated diseases; g) a method of improving dexterity and movement in a subject; h) a method of treating a subject having dwarfism; i) a method of treating a subject having dysmenorrhea; j) a method of treating a subject having dysparunia; k) a method of treating a subject having dysspermtogenic sterility; comprising the step of administering to said subject a compound of this invention and/or an analog, derivative, isomer, metabolite, pharmaceutically acceptable salt, pharmaceutical product, hydrate, N-oxide, prodrug, polymorph, impurity or crystal of said compound, or any combination thereof. In one embodiment, the compound may be characterized by the structure of formula I-XXII, or any embodiment thereof, as herein described.

In some embodiments, the compounds as described herein and/or compositions comprising the same may be used for applications and treating diseases in which the improvement of cognition, reduction or treatment of depression, or other neuroportective effects are desired.

In one embodiment, "Cognition" refers to the process of knowing, specifically the process of being aware, knowing, thinking, learning and judging. Cognition is related to the fields of psychology, linguistics, computer science, neuroscience, mathematics, ethology and philosophy. In one embodiment, "mood" refers to a temper or state of the mind. As contemplated herein, alterations mean any change for the positive or negative, in cognition and/or mood.

In one embodiment, "depression" refers to an illness that involves the body, mood and thoughts that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

In one embodiment, the methods of this invention are useful a subject, which is a human. In another embodiment, the subject is a mammal. In another embodiment the subject is an animal. In another embodiment the subject is an invertebrate. In another embodiment the subject is a vertebrate.

In one embodiment, the subject is male. In another embodiment, the subject is female. In some embodiments, while the methods as described herein may be useful for treating either males or females, females may respond more advantageously to administration of certain compounds, for certain methods, as described and exemplified herein.

In some embodiments, while the methods as described herein may be useful for treating either males or females, males may respond more advantageously to administration of certain compounds, for certain methods, as described herein.

In some embodiments, the compounds as described herein and/or compositions comprising the same may be used for applications in or treating hair loss, alopecia, androgenic alopecia, alopecia areata, alopecia secondary to chemotherapy, alopecia secondary to radiation therapy, alopecia induced by scarring or alopecia induced by stress. In one embodiment, "hair loss", or "alopecia", refers to baldness as in the very common type of male-pattern baldness. Baldness typically begins with patch hair loss on the scalp and sometimes progresses to complete baldness and even loss of body hair. Hair loss affects both males and females.

In some embodiments, the compounds as described herein and/or compositions comprising the same may be used for applications in, or treating diseases or conditions associated with a subject having anemia. In one embodiment, "anemia" refers to the condition of having less than the normal number of red blood cells or less than the normal quantity of hemoglobin in the blood, reduced hematocrit or reduced mean corpuscular volume, or reduced corpuscular size. The oxygen-carrying capacity of the blood is decreased in anemia. In some embodiments, treating anemia may also refer herein to treating underlying factors resulting in anemia, such as for example: a) hemorrhage (bleeding); b) hemolysis (excessive destruction of red blood cells); c) underproduction of red blood cells; and d) not enough normal hemoglobin. In some embodiments, treating anemia in this invention refers to treating any form thereof, including aplastic anemia, benzene poisoning, Fanconi anemia, hemolytic disease of the newborn, hereditary spherocytosis, iron deficiency anemia, osteoporosis, pernicious anemia, aplastic anemia, hemolytic anemia, sickle cell anemia, renal anemia, thalassemia, myelodysplastic syndrome, and a variety of bone marrow diseases.

In some embodiments, the compounds as described herein and/or compositions comprising the same may be used for applications in and/or treating diseases and/or conditions associated with problems with a subject's libido, or erectile dysfunction in a subject. In one embodiment, "libido", may refer to sexual desire.

In one embodiment, the term "erectile" refers to the ability to be erect or upright. An erectile tissue is a tissue, which is capable of being greatly dilated and made rigid by the distension of the numerous blood vessels, which it contains.

In another embodiment of the present invention, a method is provided for hormonal therapy in a patient (i.e., one suffering from an androgen-dependent condition) which includes contacting an androgen receptor of a patient with a compound and/or a non steroidal agonist of the present invention and/or its analog, derivative, isomer, metabolite, pharmaceutically acceptable salt, pharmaceutical product, polymorph, crystal, impurity, hydrate, N-oxide or any combination thereof, in an amount effective to bind the compound to the androgen receptor and effect a change in an androgen-dependent condition.

In one embodiment of this invention, a method is provided for hormone replacement therapy in a patient (i.e., one suffering from an androgen-dependent condition) which includes administering a compound as herein described and/or its analog, derivative, isomer, metabolite, pharmaceutically acceptable salt, pharmaceutical product, polymorph, crystal, impurity, hydrate, N-oxide or any combination thereof, to a subject, in an amount sufficient to effect a change in a hormone-dependent condition in the subject.

Androgen-dependent conditions which may be treated with the compounds and/or compositions as herein described, comprising the methods of the present invention include those conditions which are associated with aging, hypogonadism, sarcopenia, diminished erythropoiesis, osteoporosis, and any other conditions dependent upon low androgen (e.g., testosterone) or estrogen levels.

Androgen-dependent conditions which may be treated with the compounds and/or compositions as herein described, and comprising a method of the invention, may comprise conditions characterized by elevated androgen or estrogen levels, including hirsutism, infertility, polycystic ovarian syndrome, endometrial carcinoma, breast cancer, male pattern baldness, prostate cancer, testicular cancer, and others, as will be known to one skilled in the art. For such conditions, the subject may be administered a compound as herein described, alone or in combination with another therapeutic agent, as will be appreciated by one skilled in the art.

In one embodiment, this invention provides methods for the treatment of a cancer in a subject, reduction of incidence or severity or pathogenesis of a cancer in a subject, delaying progression, prolonging remission or delaying onset of cancer in a subject, comprising the step of administering to the subject a compound as herein described and/or its analog, derivative, isomer, metabolite, pharmaceutically acceptable salt, pharmaceutical product, polymorph, crystal, impurity, hydrate, N-oxide or any combination thereof. In some embodiments, such cancers are hormone-dependent or androgen receptor dependent tumors (malignant or benign) associated with reproductive tissue in males or females, such as cancer of the prostate, ovary, breast, uterus, testicle, or others.

In some embodiments, this invention provides methods for the treatment of a precancerous precursor or lesion in a subject, reduction of incidence of precancerous precursors or lesions in a subject, comprising the step of administering to the subject a compound as herein described and/or its analog, derivative, isomer, metabolite, pharmaceutically acceptable salt, pharmaceutical product, polymorph, crystal, impurity, hydrate, N-oxide or any combination thereof. In some embodiments, such precancerous precursors are androgen receptor dependent tumors found in hormone-responsive tissue or are associated with reproductive tissue in males or females, such as in the prostate, ovary, breast, uterus, testicle, or others. In some embodiments, such precancerous precursors comprise any local intraepithelial neoplasia, for example, of the prostate, the cervix, etc. In some embodiments, such methods are useful in treating neoplasia or pre-neoplasia, dysplasia or hyperplasia in a tissue, such as in reproductive tissue in males or females.

In one embodiment, this invention provides compounds, compositions and/or methods of use thereof in treating benign prostate hyperplasia (BPH). "BPH (benign prostate hyperplasia)" is a nonmalignant enlargement of the prostate gland, and is the most common non-malignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure.

In another embodiment of the present invention, the method for treating benign prostate hyperplasia (BPH) in a subject, comprises the step of administering to the subject a compound as herein described and/or its analog, derivative, isomer, metabolite, pharmaceutically acceptable salt, pharmaceutical product, polymorph, crystal, impurity, hydrate, N-oxide or any combination thereof, in an amount effective to treat BPH in the subject.

In some embodiments, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, or reducing pathogenesis of cachexia and/or cachexia associated with cancer in a subject. In another embodiment, the cancer comprise adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

In another embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, delaying the onset of lung cancer.

In another embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, delaying the onset of non small cell lung cancer.

In some embodiments, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, or reducing pathogenesis of cancer. In another embodiment, the cancer comprises androgen AR dependent tumors (malignant or benign) such as prostate cancer, breast cancer (male or female, operable or inoperable). In another embodiment the SARM compounds adjunct to ADT for treating prostate cancer; bladder cancers; brain cancers; bone tumors, colon cancer, endometrial cancer, liver cancer, lung cancer, lymphatic cancer, kidney cancer, osteosarcoma cancer, ovarian cancer, pancreas cancer, penis cancer, skin cancer, thyroid cancer; and/or hormone-dependent cancers.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for a) treating a bone related disorder; b) preventing a bone related disorder; c) suppressing a bone related disorder; d) inhibiting a bone related disorder; e) increasing a strength of a bone of a subject; f) increasing a bone mass in a subject; g) use for osteoclastogenesis inhibition.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for a) Accelerate bone repair; b) treating bone disorders; c) treating bone density loss; d) treating low bone mineral density (BMD); e) treating reduced bone mass; f) treating metabolic bone disease; g) promoting bone growth or regrowth; h) promoting bone restoration; i) promoting bone fracture repair; j) promoting bone remodeling; k) treating bone damage following reconstructive surgery including of the face, hip, or joints; l) enhancing of bone strength and function; m) increasing cortical bone mass; n) increasing trabecular connectivity.

In one embodiment, the bone related disorder is a genetic disorder, or in another embodiment, is induced as a result of a treatment regimen for a given disease. For example, and in one embodiment, the compounds as herein described are useful in treating a bone-related disorder that arises as a result of cancer metastasis to bone, or in another embodiment, as a result of androgen-deprivation therapy, for example, given in response to prostate carcinogenesis in the subject.

In one embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty.

In another embodiment, the bone-related disorder is a loss of bone mineral density (BMD). In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

In another embodiment, the primary osteoporosis is Type I primary osteoporosis. In another embodiment, the primary osteoporosis is Type II primary osteoporosis. Each type of osteoporosis represents a separate embodiment of the present invention.

According to this aspect of the invention and in one embodiment, the bone-related disorder is treated with a compound as herein described, or a combination thereof. In another embodiment, other bone-stimulating compounds can be provided to the subject, prior to, concurrent with or following administration of a compound or compounds as herein described. In one embodiment, such a bone stimulating compound may comprise natural or synthetic materials.

In one embodiment, the bone stimulating compound may comprise a bone morphogenetic protein (BMP), a growth factor, such as epidermal growth factor (EGF), a fibroblast growth factor (FGF), a transforming growth factor (TGF, an insulin growth factor (IGF), a platelet-derived growth factor (PDGF) hedgehog proteins such as sonic, indian and desert hedgehog, a hormone such as follicle stimulating hormone, parathyroid hormone, parathyroid hormone related peptide, activins, inhibins, follistatin, frizzled, frzb or frazzled proteins, BMP binding proteins such as chordin and fetuin, a cytokine such as IL-3, IL-7, GM-CSF, a chemokine, such as eotaxin, a collagen, osteocalcin, osteonectin and others, as will be appreciated by one skilled in the art.

In another embodiment, the compositions for use in treating a bone disorder of this invention may comprise a compound or compounds as herein described, an additional bone stimulating compound, or compounds, and osteogenic cells. In one embodiment, an osteogenic cell may be a stem cell or progenitor cell, which may be induced to differentiate into an osteoblast. In another embodiment, the cell may be an osteoblast. In another embodiment, nucleic acids which encode bone-stimulating compounds may be administered to the subject, which is to be considered as part of this invention.

In one embodiment, the methods of the present invention comprise administering the compound for treating osteoporosis. In another embodiment, the methods of this invention comprise administering a compound in combination with SERMs for treating osteoporosis. In another embodiment, the SERMs are tamoxifene, 4-hydroxytamoxifene, idoxifene, toremifene, ospemifene, droloxifene, raloxifene, arzoxifene, bazedoxifene, PPT (1,3,5-Tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE, (N,N-diethyl-2-[4-(phenylmethyl)-phenoxy]ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, Ban zhi lian, CT-101, CT-102, or VG-101.

In another embodiment, the methods of the present invention comprise administering the SARM compound, in combination with bisphosphonates such as alendronate, tiludroate, clodroniate, pamidronate, etidronate, alendronate, zolendronate, cimadronate, neridronate, minodronic acid, ibandronate, risedronate, or homoresidronate for treating osteoporosis.

In another embodiment, the methods of the present invention comprise administering the compound, in combination with Calcitonin such as salmon, Elcatonin, SUN-8577 or TJN-135 for treating osteoporosis.

In another embodiment, the methods of treating osteoporosis of the present invention comprise administering the SARM compound, in combination with a) vitamin D or derivative such as ZK-156979; b) vitamin D receptor ligand and analogues such as calcitriol, topitriol, ZK-150123, TEI-9647, BXL-628, Ro-26-9228, BAL-2299, Ro-65-2299 or DP-035; c) estrogen, estrogen derivative, or conjugated estrogens; d) antiestrogen, progestins, or synthetic estrogen/progestins; e) RANK ligand mAb such as denosumab formerly AMG162 (Amgen); f) $\alpha v \beta 3$ Integrin receptor antagonist; g) osteoclast vacuolar ATPase inhibitor; h) antagonist of VEGF binding to osteoclast receptors; i) calcium receptor antagonist; j) PTh (parathyroid hormone) and analogues, PTHrP analogues (parathyroid hormone-related peptide); k) Cathepsin K inhibitors (ME581, etc.); 1) strontium ranelate; m) tibolone; n) HCT-1026, PSK3471; o) gallium maltolate; p) nutropin AQ; q) prostaglandins (for osteo); r) p38 protein kinase inhibitor; s) bone morphogenetic protein; t) inhibitor of BMP antagonism; u) HMG-CoA reductase inhibitor; v) vitamin K or derivative; w) ipriflavone; x) fluoride salts; y) dietary calcium supplement, and z) osteoprotegerin.

In one embodiment, the methods of this invention are useful in treating diseases or disorders caused by, or associated with a hormonal disorder, disruption or imbalance. In one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is a cortico-steroid. In another embodiment, the hormone is Luteinizing Hormone (LH). In another embodiment, the hormone is Follicle Stimulating Hormone (FSH). In another embodiment, the hormone is any other hormone known in the art. In another embodiment, the hormonal disorder, disruption or imbalance is associated with menopause. In another embodiment, the hormonal disorder, disruption or imbalance is associated with andropause, andropausal vasomotor symptoms, andropausal gynecomastia, muscle strength and/or function, bone strength and/or function and anger. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject. Each possibility represents a separate embodiment of the present invention.

In another embodiment the invention is directed to treating sarcopenia or cachexia, and associated conditions related thereto, for example diseases or disorders of the bone.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder; and/or treating, preventing, inhibiting, reducing or suppressing end stage renal disease; and/or 6) treating, preventing, inhibiting, reducing or suppressing frailty.

In another embodiment, the use of a compound for treating a subject having a muscle wasting disorder, or any of the disorders described herein, includes administering a pharmaceutical composition including a compound as herein described. In another embodiment, the administering step includes intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

A muscle is a tissue of the body that primarily functions as a source of power. There are three types of muscles in the body: a) skeletal muscle—the muscle responsible for moving extremities and external areas of the bodies; b) cardiac muscle—the heart muscle; and c) smooth muscle—the muscle that is in the walls of arteries and bowel.

A wasting condition or disorder is defined herein as a condition or disorder that is characterized, at least in part, by an abnormal, progressive loss of body, organ or tissue mass. A wasting condition can occur as a result of a pathology such as, for example, cancer, or an infection, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, "muscle wasting" or "muscular wasting", used herein interchangeably, refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of a pathology, disease, condition or disorder. In one embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious. As described herein, the pathologies, diseases, conditions or disorders for which the compounds and compositions of the present invention are administered are those that directly or indirectly produce a wasting (i.e. loss) of muscle mass, that is a muscle wasting disorder.

In one embodiment, muscle wasting in a subject is a result of the subject having a muscular dystrophie; muscle atrophy; X-linked spinal-bulbar muscular atrophy (SBMA).

The muscular dystrophies are genetic diseases characterized by progressive weakness and degeneration of the skeletal or voluntary muscles that control movement. The muscles of the heart and some other involuntary muscles are also affected in some forms of muscular dystrophy. The major forms of muscular dystrophy (MD) are: duchenne muscular dystrophy, myotonic dystrophy, duchenne muscular dystrophy, becker muscular dystrophy, limb-girdle muscular dystrophy, facioscapulhumeral muscular dystrophy, congenital muscular dystrophy, oculopharyngeal muscular dystrophy, distal muscular dystrophy and emery-dreifuss muscular dystrophy.

Muscular dystrophy can affect people of all ages. Although some forms first become apparent in infancy or childhood, others may not appear until middle age or later. Duchenne MD is the most common form, typically affecting children. Myotonic dystrophy is the most common of these diseases in adults.

Muscle atrophy (MA) is characterized by wasting away or diminution of muscle and a decrease in muscle mass. For example, Post-Polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gene on the X chromosome, affects only males, and its onset is in adulthood. Because the primary disease cause is an androgen receptor mutation, androgen replacement is not a current therapeutic strategy. There are some investigational studies where exogenous testosterone propionate is being given to boost the levels of androgen with hopes of overcoming androgen insensitivity and perhaps provide an anabolic effect. Still, use of supraphysiological levels of testosterone for supplementation will have limitations and other potentially serious complications.

Sarcopenia is a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting and other tissue wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting, or wasting of other tissue. Studies have shown that in patients suffering injuries, chronic illnesses, burns, trauma or cancer, who are hospitalized for long periods of time, there is a long-lasting unilateral muscle wasting, and a decrease in body mass.

Injuries or damage to the central nervous system (CNS) are also associated with muscle wasting and other wasting disorders. Injuries or damage to the CNS can be, for example, caused by diseases, trauma or chemicals. Examples are central nerve injury or damage, peripheral nerve injury or damage and spinal cord injury or damage. In one embodiment CNS damage or injury comprise Alzheimer's diseases (AD); anger (mood); anorexia, anorexia nervosa, anorexia associated with aging and/or assertiveness (mood).

In another embodiment, muscle wasting or other tissue wasting may be a result of alcoholism, and may be treated with the compounds and compositions of the invention, representing embodiments thereof.

In one embodiment, the invention provides a use of SARM compound as described herein or its prodrug, analog, isomer, metabolite, derivative, pharmaceutically acceptable salt, pharmaceutical product, polymorph, crystal, impurity, N-oxide, hydrate or any combination thereof for the treatment of a wasting disease, disorder or condition in a subject.

In one embodiment, the wasting disease, disorder or condition being treated is associated with chronic illness This invention is directed to treating, in some embodiments, any wasting disorder, which may be reflected in muscle wasting, weight loss, malnutrition, starvation, or any wasting or loss of functioning due to a loss of tissue mass.

In some embodiments, wasting diseases or disorders, such as cachexia; malnutrition, tuberculosis, leprosy, diabetes, renal disease, chronic obstructive pulmonary disease (COPD), cancer, end stage renal failure, sarcopenia, emphysema, osteomalacia, or cardiomyopathy, may be treated by the methods of this invention, via the administration of a SARM compound as herein described, compositions comprising the same, with or without additional drugs, compounds, or agents, which provide a therapeutic effect for the condition being treated.

In some embodiments, wasting is due to infection with enterovirus, Epstein-Barr virus, herpes zoster, HIV, trypanosomes, influenze, coxsackie, *rickettsia, trichinella, schistosoma* or mycobacteria, and this invention, in some embodiments, provides methods of treatment thereof.

Cachexia is weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass.

Cachexia is also seen in acquired immunodeficiency syndrome (AIDS), human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

In some embodiments, the present invention provides a method for treating, reducing the incidence, delaying the onset or progression, or reducing and/or abrogating the symptoms associated with an infection in a subject. In one embodiment, the method comprises administering to a subject a composition comprising a compound and an immunomodulating agent, an anti-infective agent, a gene therapy agent, or a combination thereof. In some embodiments, infections comprise actinomycosis, anaplasmosis, anthrax, aspergillosis, bacteremia, bacterial mycoses, *bartonella* infections, botulism, brucellosis, *burkholderia infections, campylobacter* infections, candidiasis, cat-scratch disease, chlamydia infections, cholera, *clostridium* infections, coccidioidomycosis, cross infection, cryptococcosis, dermatomycoses, diphtheria, ehrlichiosis, *Escherichia coli* infections, fasciitis, necrotizing, *Fusobacterium* infections, gas gangrene, gram-negative bacterial infections, gram-positive bacterial infections, histoplasmosis, impetigo, *Klebsiella* infections, legionellosis, leprosy, leptospirosis, *Listeria* infections, lyme disease, maduromycosis, melioidosis, mycobacterium infections, mycoplasma infections, mycoses, *nocardia* infections, onychomycosis, plague, pneumococcal infections, pseudomonas infections, psittacosis, q fever, rat-bite fever, relapsing fever, rheumatic fever, *Rickettsia* infections, rocky mountain spotted fever, *salmonella* infections, scarlet fever, scrub typhus, sepsis, sexually transmitted diseases, Staphylococcal infections, Streptococcal infections, tetanus, tick-borne diseases, tuberculosis, tularemia, typhoid fever, typhus, louse-borne, *vibrio* infections, yaws, *yersinia* infections, zoonoses, zygomycosis, acquired immunodeficiency syndrome, adenoviridae infections, alphavirus infections, arbovirus infections, borna disease, bunyaviridae infections, caliciviridae infections, chickenpox, coronaviridae infections, coxsackievirus infections, cytomegalovirus infections, dengue, DNA virus infections, eethyma, contagious, encephalitis, arbovirus, Epstein-barr virus infections, erythema infectiosum, hantavirus infections, hemorrhagic fevers, viral hepatitis, viral human herpes simplex, herpes zoster, herpes zoster oticus, herpesviridae infections, infectious mononucleosis, human-lassa fever, measles, molluscum, contagiosum, mumps, paramyxoviridae infections, phlebotomus fever, polyomavirus infections, rabies, respiratory syncytial virus infections, rift valley fever, RNA virus infections, rubella, slow virus diseases, smallpox, subacute sclerosing panencephalitis, tumor virus infections, warts, west nile fever, virus diseases, yellow fever, amebiasis, anisakiasis, *ascariasis*, babesiosis, blastocystis hominis infections, bug bite, cestode infections, chagas disease, cryptosporidiosis, cyclosporiasis, cysticercosis, dientamoebiasis, diphyllobothriasis, dracunculiasis, echinococcosis, ectoparasitic infestations, filariasis, giardiasis, helminthiasis, hookworm infections, larva migrans, leishmaniasis, lice infestations, loiasis, malaria, mite infestations, myiasis, onchocerciasis, protozoan infections, scabies, schistosomiasis, skin diseases, parasitic, strongyloidiasis, taeniasis, toxocariasis, toxoplasmosis, trichinosis, trichomonas infections, trypanosomiasis, trypanosomiasis, african, or whipworm infections.

In some embodiments, the present invention provides a method for treating, reducing the incidence, delaying the onset or progression, or reducing and/or abrogating the symptoms associated with a musculoskeletal disease in a subject. In one embodiment, the method comprises administering to a subject a composition comprising a compound and an anticancer agent, an immunomodulating agent, an antidiabetic agent, an agent treating the central nervous system, an agent treating a metabolic disease, an agent treating a wasting disease, a gene therapy agent, an agent treating the endocrine system, vitamins, or a combination thereof. In some embodiments, musculoskeletal diseases comprise achondroplasia, acquired hyperostosis syndrome, acrocephalosyndactylia, arthritis, arthrogryposis, arthropathy, neurogenic bursitis, cartilage diseases, cleidocranial dysplasia, clubfoot, compartment syndromes, craniofacial dysostosis, craniosynostoses, dermatomyositis, Dupuytren's contracture, dwarfism, Ellis Van Creveld syndrome, enchondromatosis, eosinophilia-myalgia syndrome, exostoses, fasciitis, fatigue syndrome, fibromyalgia, fibrous dysplasia of bone, fibrous dysplasia, polyostotic, flatfoot, foot deformities, Freiberg's disease, funnel chest, Goldenhar syndrome, gout, hallux valgus, hip dislocation, hyperostosis, intervertebral disk displacement, kabuki make-up syndrome, Klippel-Feil syndrome, Langer-Giedion syndrome, Legg-Perthes disease, lordosis, mandibulofacial dysostosis, melorheostosis, mitochondrial myopathies, muscle cramp, muscle spasticity, muscular dystrophies, musculoskeletal abnormalities, musculoskeletal diseases, myositis, myositis ossificans, myotubular myopathy, osteitis deformans, osteoarthritis, osteochondritis, osteogenesis imperfecta, osteomyelitis, osteonecrosis, osteopetrosis, osteoporosis, poland syndrome, polychondritis, relapsing, polymyalgia rheumatica, polymyositis, rhabdomyolysis, rheumatic diseases, Russell silver syndrome, Scheuermann's disease, scoliosis, Sever's disease/calceneal apophysitis, spinal diseases, spinal osteophytosis, spinal stenosis, spondylitis, ankylosing, spondylolisthesis, sprengel's deformity, synovitis, tendinopathy, tennis elbow, tenosynovitis, thanatophoric dysplasia, or Tietze's syndrome.

In some embodiments, the present invention provides a method for treating, reducing the incidence, delaying the onset or progression, or reducing and/or abrogating the symptoms associated with a digestive system disease in a subject. In one embodiment, the method comprises administering to a subject a composition comprising a compound and an anticancer agent, an immunomodulating agent, an antidiabetic agent, an agent treating the central nervous system, an agent treating the gastrointestinal system, an anti-infective agent, an agent treating a metabolic disease, a gene therapy agent, an agent treating the endocrine system, vitamins, or a combination thereof. In some embodiments, gastrointestinal diseases comprise adenomatous polyposis coli, Alagille syndrome, anus diseases, appendicitis, barrett esophagus, biliary atresia, biliary tract diseases, Caroli disease, celiac disease, cholangitis, cholecystitis, cholelithiasis, colitis, ulcerative, Crohn's disease, deglutition disorders, duodenal ulcer, dysentery, enterocolitis, pseudomembranous, esophageal achalasia, esophageal atresia, esophagitis, exocrine pancreatic insufficiency, fatty liver, fecal incontinence, gastritis, gastritis, hypertrophic, gastroenteritis, gastroesophageal reflux, gastroparesis, hemorrhoids, hepatic vein thrombosis, hepatitis, hepatitis, chronic, hernia, diaphragmatic, hernia, hiatal, Hirschsprung disease, hypertension (HTN), portal, inflammatory bowel diseases, intestinal diseases, intestinal neoplasms, intestinal neuronal dysplasia, intestinal obstruction, irritable bowel syndrome, lactose intolerance, liver cirrhosis, liver diseases, meckel diverticulum, pancreatic diseases, pancreatic neoplasms, pancreatitis, peptic ulcer, Peutz-Jeghers syndrome, proctitis, rectal diseases, rectal prolapse, short bowel syndrome, tracheoesophageal fistula, whipple disease, or Zollinger-Ellison syndrome.

In some embodiments, the present invention provides a method for treating, reducing the incidence, delaying the onset or progression, or reducing and/or abrogating the symptoms associated with a stomatognathic disease in a subject. In one embodiment, the method comprises administering to a subject a composition comprising a compound and an anticancer agent, an immunomodulating agent, an anti-infective agent, an agent treating a wasting disease, a gene therapy agent, an agent treating the endocrine system, vitamins, or a combination thereof. In some embodiments, stomatognathic diseases comprise ankyloglossia, bruxism, burning mouth syndrome, cheilitis, cherubism, cleft lip, dentigerous cyst, gingivitis, glossitis, benign migratory, herpes labialis, Ludwig's angina, macroglossia, Melkersson-Rosenthal syndrome, periodontal diseases, Pierre Robin syndrome, prognathism, salivary gland diseases, sialorrhea, stomatitis, aphthous, temporomandibular joint disorders, temporomandibular joint dysfunction syndrome, or xerostomia.

In some embodiments, the present invention provides a method for treating, reducing the incidence, delaying the onset or progression, or reducing and/or abrogating the symptoms associated with a respiratory tract disease in a subject. In one embodiment, the method comprises administering to a subject a composition comprising a compound and an anticancer agent, an immunomodulating agent, an agent treating the central nervous system, an agent treating the cardiovascular system, an anti-infective agent, an agent treating a wasting disease, a gene therapy agent, an agent treating the endocrine system, vitamins, or a combination thereof. In some embodiments, respiratory tract diseases comprise airway obstruction, apnea, asbestosis, asthma, asthma-induced muscle weakness or bone weakness, atelectasis, berylliosis, bronchial diseases, bronchiectasis, bronchiolitis, bronchiolitis obliterans organizing pneumonia, bronchitis, bronchopulmonary dysplasia, chronic obstructive pulmonary disease (COPD), common cold, cough, empyema, pleural, epiglottitis, glucocorticoid (GC)-induced myopathy or osteopenia hemoptysis, hypertension, pulmonary, hyperventilation, kartagener syndrome, lung abscess, lung diseases, meconium aspiration syndrome, pleural effusion, pleurisy, pneumonia, pneumothorax, pulmonary alveolar proteinosis, pulmonary disease, chronic obstructive, pulmonary edema, pulmonary embolism, pulmonary emphysema, pulmonary fibrosis, respiratory distress syndrome, newborn-respiratory hypersensitivity, respiratory tract infections, rhinoscleroma, scimitar syndrome, severe acute respiratory syndrome, silicosis, sleep apnea, central stridor, tracheal stenosis, decreased muscle mass or bone mass due to asthma, wasting in chronic obstructive pulmonary disease (COPD), Wegener's granulomatosis, or whooping cough.

In some embodiments, the present invention provides a method for treating, reducing the incidence, delaying the onset or progression, or reducing and/or abrogating the symptoms associated with an otorhinolaryngologic disease in a subject. In one embodiment, the method comprises administering to a subject a composition comprising a compound and an anti-cancer agent, an immunomodulating agent, an anti-infective agent, an agent treating a wasting disease, a gene therapy agent, an agent treating the endocrine system, vitamins, or a combination thereof. In some embodiments, otorhinolaryngologic diseases comprise cholesteatoma, middle ear, croup, deafness, epistaxis, hearing loss, hyperacusis, labyrinthitis, laryngitis, laryngomalacia, laryngostenosis, mastoiditis, Meniere's disease, nasal obstruction, nasal polyps, otitis, otorhinolaryngologic diseases, otoscierosis, pharyngitis, presbycusis, retropharyngeal abscess, rhinitis, sinusitis, tinnitus, tonsillitis, tympanic membrane perforation, vestibular neuronitis, vocal cord paralysis, or voice disorders.

In some embodiments, the present invention provides a method for treating, reducing the incidence, delaying the onset or progression, or reducing and/or abrogating the symptoms associated with a nervous system disease in a subject. In one embodiment, the method comprises administering to a subject a composition comprising a compound and an anticancer agent, an immunomodulating agent, an agent treating the central nervous system, an anti-infective agent, an agent treating a metabolic disease, an agent treating a wasting disease, a gene therapy agent, an agent treating the endocrine system, vitamins, or a combination thereof. In some embodiments, nervous system diseases comprise autonomic nervous system diseases, central nervous system diseases, cranial nerve diseases, demyelinating diseases, nervous system malformations, neurologic manifestations, or neuromuscular diseases.

In some embodiments, autonomic nervous system diseases comprise causalgia, or reflex sympathetic dystrophy.

In some embodiments, central nervous system diseases comprise Alzheimer's disease, arachnoiditis, brain abscess, brain ischemia, central nervous system infections, cerebral palsy, cerebrovascular disorders, corticobasal ganglionic degeneration (CBGD), Creutzfeldt-Jakob syndrome, Dandy-Walker syndrome, dementia, encephalitis, encephalomyelitis, epilepsy, epilepsy induced hypogonadal and/or hypermetabolic state, essential tremor, Friedreich ataxia, Gerstmann-Straussler-Scheinker disease, Hallervorden-Spatz syndrome, Huntington disease, hydrocephalus, hypoxia, insomnia, ischemic attack, kuru, Landau-Kleffner syndrome, Lewy Body disease, Machado-Joseph disease, meige syndrome, meningitis, bacterial meningitis, viral, migraine disorders, movement disorders, multiple system atrophy, myelitis, olivopontocerebellar atrophies, Parkinson's disease, parkinsonian disorders, poliomyelitis, postpoliomyelitis syndrome, prion diseases, pseudotumor cerebri, Shy-Drager syndrome, spasms, infantile, spinal cord diseases, supranuclear palsy, syringomyelia, thalamic diseases, tic disorders, tourette syndrome, or uveomeningoencephalitic syndrome. In some embodiments, the central nervous system disease is cystic fibrosis induced hypogonadal state.

In some embodiments, cranial nerve diseases comprise bell palsy, cranial nerve diseases, facial hemiatrophy, facial neuralgia, glossopharyngeal nerve diseases, Moebius syndrome, or trigeminal neuralgia.

In some embodiments, central nervous system diseases comprise injuries or damage to the central nervous system (CNS). In some embodiments, injuries or damage to the CNS may be associated with muscle wasting disorders. Injuries or damage to the CNS can be, for example, caused by diseases, trauma or chemicals. Examples are central nerve injury or damage, peripheral nerve injury or damage and spinal cord injury or damage.

Studies involving patients with spinal cord injuries (SCI) have shown that central neurotransmitters may be altered after SCI causing hypothalamus-pituitary-adrenal axis dysfunction, whose disruption led to a significant decrease in testosterone and other hormone levels. SCI or other acute illness or trauma characteristically includes heightened catabolism in conjunction with the lowered anabolic activity resulting in a condition that is prone to loss of lean body tissue, which is often accompanied by disturbed nutrient utilization. The effects of the loss of lean body mass include the development of wounds and impaired healing mechanisms, further compounding the problem. Because of poor nutrition and protein combined with immobilization, patients with spinal cord injury are at high risk for bed sores.

In one embodiment, a wide variety of injuries of the CNS may be treated by the methods of the present invention. CNS injury may refer, in one embodiment, to a breakdown of the membrane of a nerve cell, or, in another embodiment, to the inability of the nerve to produce and propagate nerve impulses, or in another embodiment, to the death of the cell. An injury includes damage that directly or indirectly affects the normal functioning of the CNS. The injury may be a structural, physical, or mechanical impairment and may be caused by physical impact, as in the case of a crushing, compression, or stretching of nerve fibers. Alternatively, the cell membrane may be destroyed by or degraded by an illness, a chemical imbalance, or a physiological malfunction such as anoxia (e.g., stroke), aneurysm, or reperfusion. A CNS injury includes, for example and without limitation, damage to retinal ganglion cells, a traumatic brain injury, a stroke-related injury, a cerebral aneurism-related injury, a spinal cord injury, including monoplegia, diplegia, paraplegia, hemiplegia and quadriplegia, a neuroproliferative disorder, or neuropathic pain syndrome.

With injury to the spinal cord of a mammal, connections between nerves in the spinal cord are broken. Such injuries block the flow of nerve impulses for the nerve tracts affected by the injury, with a resulting impairment to both sensory and motor function. Injuries to the spinal cord may arise from compression or other contusion of the spinal cord, or a crushing or severing of the spinal cord. A severing of the spinal cord, also referred to herein as a "transection," may be a complete severing or, may be an incomplete severing of the spinal cord.

In some embodiments, the methods of treating a subject suffering form a CNS injury or, in other embodiments, spinal cord injury, may be accompanied by treatment of the subject with electrical stimulation of the injured site and the administration of a purine nucleoside, or analog thereof, for example as described in United States Patent Application Publication Number 20040214790A1.

In some embodiments, demyelinating diseases comprise adrenoleukodystrophy, alexander disease, canavan disease, demyelinating disease, diffuse cerebral sclerosis of schilder, leukodystrophy-globoid cell, leukodystrophy-metachromatic, multiple sclerosis, or neuromyelitis optica.

In some embodiments, nervous system malformations comprise Arnold-Chiari malformation, Charcot-Marie-Tooth disease, encephalocele, hereditary motor and sensory neuropathies, septo-optic dysplasia, spina bifida occulta, or spinal dysraphism.

In some embodiments, neurologic manifestations comprise agnosia, amnesia, anomia, aphasia, apraxias, back pain, Brown-Sequard syndrome, cerebellar ataxia, chorea, communication disorders, confusion, dizziness, dyslexia, dystonia, facial paralysis, fasciculation, gait disorders, neurologic-headache, hemiplegia, memory disorders, mental retardation, mutism, myoclonus, neck pain, nonverbal learning disorder, olfaction disorders, pain, paralysis, phantom limb, prosopagnosia, quadriplegia, seizures, spasm, speech disorders, synesthesia tardive dyskinesia, taste disorders, torticollis, tremor, trismus, unconsciousness, or vertigo.

In some embodiments, neuromuscular diseases comprise. amyotrophic lateral sclerosis, brachial plexus neuritis, brachial plexus neuropathies, bulbar palsy, carpal tunnel syndrome, cubital tunnel syndrome, diabetic neuropathies, dysautonomia, guillain, barre syndrome, hereditary sensory and autonomic neuropathies, miller fisher syndrome, motor neuron disease, muscular atrophy, spinal, myasthenia gravis, myopathies, structural, congenital, nerve compression syndromes, neuralgia, neuromuscular diseases, paralyses, familial periodic, peripheral nervous system diseases, poems syndrome, polyneuropathies, polyradiculopathy, refsum disease, sciatica, spinal muscular atrophies of childhood, stiff-person syndrome, thoracic outlet syndrome, or ulnar nerve compression syndromes.

In one embodiment, methods of treating a subject with a nervous system disease encompass treating any secondary conditions in the subject, which arise due to the subject having a nervous system disease, some of which are described herein.

In some embodiments, the present invention provides a method for treating, reducing the incidence, delaying the onset or progression, or reducing and/or abrogating the symptoms associated with an ophthalmic disease in a subject. In one embodiment, the method comprises administering to a subject a composition comprising a compound and an anti-cancer agent, an immunomodulating agent, an agent treating the cardiovascular system, an anti-infective agent, an agent treating a wasting disease, a gene therapy agent, an agent treating the endocrine system, vitamins, or a combination thereof. In some embodiments ophthalmic disease comprise acute zonal occult outer retinopathy, Adie syndrome, albinism, ocular-amaurosis, fugax, amblyopia, aniridia, anisocoria, anopthalmos, aphakia, astigmatism, blepharitis, blepharoptosis, blepharospasm, blindness, cataract, chalazion, chorioretinitis, choroideremia, coloboma, color vision defects, conjunctivitis, corneal diseases, corneal dystrophies, corneal edema, corneal ulcer, diabetic retinopathy, diplopia, distichiasis, dry eye syndromes, Duane retraction syndrome, ectropion, entropion, esotropia, exfoliation syndrome, exotropia, eye hemorrhage, eye neoplasms, eyelid diseases, floaters, general fibrosis syndrome, glaucoma, gyrate atrophy, hemianopsia, Henmanski-Pudlak syndrome, hordeolum, Horner syndrome, hyperopia, hyphema, iritis, Kearns-Sayer syndrome, keratitis, keratoconus, lacrimal apparatus diseases, lacrimal duct obstruction, lens diseases, macular degeneration, micropthalmos, myopia, nystagmus, pathologic, ocular motility disorders, oculomotor nerve diseases, opthalmoplegia, optic atrophies, optic nerve diseases, optic neuritis, optic neuropathy, orbital cellulitis, papilledema, peter's anomaly, presbyopia, pterygium, pupil disorders, refractive errors, retinal detachment, retinal diseases, retinal vein occlusion, retinitis pigmentosa, retinopathy of prematurity, retinoschisis, scleritis, scotoma, strabismus, Thygeson's superficial punctate keratitis, trachoma, uveitis, white dot syndrome, vision disorders, or vitreous disorders In some embodiments, the present invention provides a method for treating, reducing the incidence, delaying the onset or progression, or reducing and/or abrogating the symptoms associated with an urologic and/or male genital disease in a subject. In one embodiment, the method comprises administering to a subject a composition comprising a compound and an anti-cancer agent, an immunomodulating agent, an antidiabetic agent, an agent treating the gastrointestinal system, an anti-infective agent, an agent treating the kidney, an agent treating a metabolic disease, an agent treating a wasting disease, a gene therapy agent, an agent treating the endocrine system, vitamins, or a combination thereof. In some embodiments, an urologic and/or male genital diseases comprise anti-glomerular basement membrane disease, balanitis, bladder exstrophy, bladder neoplasms, cryptorchidism, cystitis, interstitial, diabetes insipidus, nephrogenic, epididymitis, fournier gangrene, glomerulonephritis, Goodpasture syndrome, hematospermia, hematuria, hemolytic-uremic syndrome, hydronephrosis, hypospadias, impotence, infertility, kidney calculi, kidney failure, acute, kidney failure, chronic, kidney tubular necrosis, acute, medullary sponge kidney, multicystic dysplastic kidney, nephritis, hereditary, nephrosis, nephrotic syndrome, nocturia, oliguria, penile diseases, penile induration, penile neoplasms, phimosis, priapism, prostatic diseases, benign prostate hyperplasia, prostatic neoplasms, proteinuria, pyelonephritis, Reiter disease, renal artery obstruction, spermatic cord torsion, testicular diseases, urethral stricture, urethritis, urinary retention, urinary tract infections, urination disorders, urologic and male genital diseases, urologic diseases, varicocele, vesico, or urethral reflux.

In some embodiments, the present invention provides a method for treating, reducing the incidence, delaying the onset or progression, or reducing and/or abrogating the symptoms associated with a dermatological disorder in a subject. In one embodiment, the method comprises administering to a subject a composition comprising a compound and anti-cancer agent, an immunomodulating agent, an agent treating a dermatological disorder, an anti-infective agent, a gene therapy agent, an agent treating the endocrine system, vitamins, or a combination thereof. In some embodiments, dermatological disorders comprise acne, actinic keratosis, alopecia, androgenic alopecia, alopecia greata, alopecia secondary to chemotherapy, alopecia secondary to radiation therapy, alopecia induced by scarring, alopecia induced by stress, angioma, athlete's foot, aquagenic pruritus, atopic dermatitis, baldness, premature baldness, male pattern baldness, androgenic baldness, basal cell carcinoma, burns, bed sore, Behcet's disease, blepharitis, boil, Bowen's disease, bullous pemphigoid, canker sore, carbuncles, cellulitis, chloracne, chronic dermatitis of the hands and feet, dyshidrosis, cold sores, contact dermatitis, creeping eruption, dandruff, dermatitis, dermatitis herpetiformis, dermatofibroma, diaper rash, eczema, epidermolysis bullosa, erysipelas, erythroderma, friction blister, genital wart, hidradenitis, suppurativa, hives, hyperhidrosis, ichthyosis, impetigo, jock itch, Kaposi's sarcoma, keloid, keratoacanthoma, keratosis pilaris, lice infection, lichen planus, lichen simplex chronicus, lipoma, lymphadenitis, malignant melanoma, melasma, miliaria, molluscum contagiosum, nummular dermatitis, paget's disease of the nipple, pediculosis, pemphigus, perioral dermatitis, photoallergy, photosensitivity, pityriasis rosea, pityriasis rubra pilaris, psoriasis, raynaud's disease, ring worm, rosacea, scabies, scleroderma, sebaceous cyst, seborrheic keratosis, seborrhoeic dermatitis, shingles, skin cancer, skin tags, spider veins, squamous cell carcinoma, stasis dermatitis, tick bite, tinea barbae, tinea capitis, tinea corporis, tinea cruris, tinea pedis, tinea unguium, tinea versicolor, tinea, tungiasis, vitiligo, or warts.

In one embodiment, the dermatological disorder is a wound or a burn. In some embodiments, wounds and/or ulcers are found protruding from the skin or on a mucosal surface or as a result of an infarction in an organ. A wound may be a result of a soft tissue defect or a lesion or of an underlying condition. In one embodiment, the term "wound" denotes a bodily injury with disruption of the normal integrity of tissue structures. The term is also intended to encompass the terms "sore", "lesion", "necrosis" and "ulcer". In one embodiment, the term "sore" refers to any lesion of the skin or mucous membranes and the term "ulcer" refers to a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions. All of these are encompassed by the term "wound", which denotes any wound at any particular stage in the healing process including the stage before any healing has initiated or even before a specific wound like a surgical incision is made (prophylactic treatment).

Examples of wounds which can be prevented and/or treated in accordance with the present invention are, e.g., aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores etc. Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g. caused by gonorrhoea (including urethritis, endocervicitis and proctitis). Conditions related to wounds or sores which may be successfully treated according to the invention are burns, anthrax, tetanus, gas gangrene, scalatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore as mentioned above, in the present context the term "wounds" encompasses the term "ulcer", "lesion", "sore" and "infarction", and the terms are indiscriminately used unless otherwise indicated.

The kinds of wounds to be treated according to the invention include also i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues) and infarctions.

In other aspects of the invention, the wound to be prevented and/or treated is selected from the group consisting of aseptic wounds, infarctions, contused wounds, incised wounds, lacerated wounds, non-penetrating wounds, open wounds, penetrating wounds, perforating wounds, puncture wounds, septic wounds and subcutaneous wounds.

Other wounds which are of importance in connection with the present invention are wounds like ischemic ulcers, pressure sores, fistulae, severe bites, thermal burns and donor site wounds.

In one embodiment, the compound as described herein is useful in wound healing as an adjunct to physical therapy/rehabilitation, as an anabolic agent. In another embodiment, the compound as described herein is useful in promoting healing of anterior cruciate ligament (ACL) or medial cruciate ligament (MCL) injuries, or accelerating recovery after ACL or MCL surgery. In another embodiment, the compound as described herein is useful in enhancing athletic performance. In another embodiment, the compound as described herein is useful in treating burns. In another embodiment, the compound as described herein is useful in stimulating cartilage regrowth. In another embodiment, the compound as described herein is useful in preventing, treating, or reversing of catabolism associated with prolonged critical illness, pulmonary dysfunction, ventilator dependency, aging, AIDS, trauma, surgery, congestive heart failure, cardiac myopathy, burns, cancer, COPD. In another embodiment, the compound as described herein is useful in preventing or reversing protein catabolism due to trauma. In another embodiment, the compound as described herein is useful as a) adjunct to cauterization therapy (laser or radio) as is used in surgery to promote wound healing, b) adjunct to cryotherapy to promote wound healing, c) adjunct to chemotherapy to prevent side effects such as alopecia, hypogonadism, muscle wasting, osteopenia, osteoporosis, sarcopenia, increased LDL, TG or total cholesterol, decreased HDL. In another embodiment, the compound as described herein is useful in chronic catabolic state (coma, wasting conditions, starvation, eating disorders); concomitant bone fracture and muscle damage; critical illness in which muscle or bone wasting are apparent; and/or connective tissue diseases and disorders.

Ischemic ulcers and pressure sores are wounds, which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

In some embodiments, burns are associated with reduced testosterone levels, and hypgonadism is associated with delayed wound healing. In one embodiment, the methods of this invention, provide for treating a subject suffering from a wound or a burn.

In some embodiments, the present invention provides a method for prooting healing of anterior cruciate ligament (ACL) or medial cruciate ligament (MCL) injuries, or accelerating recovery after ACL or MCL surgery.

In some embodiments, the present invention provides a method for treating, reducing the incidence, delaying the onset or progression, or reducing and/or abrogating the symptoms associated with an endocrine disorder in a subject. In one embodiment, the method comprises administering to a subject a composition comprising a compound and anti-cancer agent, an immunomodulating agent, an antidiabetic agent, an agent treating the cardiovascular system, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, endocrine disorders comprise acromegaly, Addison disease, adrenal gland diseases, adrenal hyperplasia, congenital, androgen-insensitivity syndrome, congenital hypothyroidism, Cushing syndrome, diabetes insipidus, diabetes mellitus, diabetes mellitus-type 1, diabetes mellitus-type 2, diabetic, ketoacidosis, empty Sella syndrome, endocrine gland neoplasms, endocrine system diseases, gigantism, gonadal disorders, graves disease, hermaphroditism, hyperaldosteronism, hyperglycemic hyperosmolar nonketotic coma, hyperpituitarism, hyperprolactinemia, hyperthyroidism, hypogonadism, hypopituitarism, hypothyroidism, Kallmann syndrome, Nelson syndrome, parathyroid diseases, pituitary diseases, polyendocrinopathies, autoimmune, puberty, delayed, puberty, precocious, renal osteodystrophy, thyroid diseases, thyroid hormone resistance syndrome, thyroid neoplasms, thyroid nodule, thyroiditis, thyroiditis, autoimmune, thyroiditis, subacute, or Wolfram syndrome.

In one embodiment, "Hypogonadism" is a condition resulting from or characterised by abnormally decreased functional activity of the gonads, with retardation of growth and sexual development.

In some embodiments, the present invention provides a method for treating, reducing the incidence, delaying the onset or progression, or reducing and/or abrogating the symptoms associated with urogenital disease and/or fertility in a subject. In one embodiment, the method comprises administering to a subject a composition comprising a compound of this invention and anti-cancer agent, an immunomodulating agent, an anti-infective agent, an agent treating the kidney, gene therapy agent, an agent treating the endocrine system, vitamins, or a combination thereof. In some embodiments, urogenital diseases and/or fertility diseases comprise abortion, spontaneous-adhesions-pelvic, candidiasis, vulvovaginal, depression-postpartum, diabetes, gestational, dyspareunia, dystocia, eclampsia, endometriosis, fetal death, fetal growth retardation, fetal membranes, premature rupture, genital diseases, female, genital neoplasms, female, hydatidiform mole, hyperemesis gravidarum, infertility, ovarian cysts, ovarian torsion, pelvic inflammatory disease, placenta diseases, placental insufficiency, polycystic ovary syndrome, polyhydramnios, postpartum hemorrhage, pregnancy complications, pregnancy, ectopic, pruritus vulvae, puerperal disorders, puerperal infection, salpingitis, trophoblastic neoplasms, uterine cervix incompetence, uterine inversion, uterine prolapse, vaginal diseases, vulvar diseases, vulvar lichen sclerosis.

In some embodiments, the present invention provides a method for treating, reducing the incidence, delaying the onset or progression, or reducing and/or abrogating the symptoms associated with hemic and/or lymphatic disease in a subject. In one embodiment, the method comprises administering to a subject a composition comprising a compound of this invention and an anti-cancer agent, an immunomodulating agent, an antidiabetic agent, an agent treating the cardiovascular system, an anti-infective agent, an agent treating the liver, an agent treating the kidney, an agent treating a metabolic disease, a gene therapy agent, an agent treating the endocrine system, vitamins, or a combination thereof. In some embodiments, hemic and/or lymphatic diseases comprise afibrinogenemia, anemia, aplastic anemia, hemolytic anemia, congenital nonspherocytic anemia, megaloblastic anemia, pernicious anemia, sickle cell anemia, renal anemia, angiolymphoid hyperplasia with eosinophilia, antithrombin III deficiency, Bernard-Soulier syndrome, blood coagulation disorders, blood platelet disorders, blue rubber bleb nevus syndrome, Chediak-Higashi syndrome, cryoglobulinemia, disseminated intravascular coagulation, eosinophilia, Erdheim-Chester disease, erythroblastosis, fetal, evans syndrome, factor V deficiency, factor VII deficiency, factor X deficiency, factor XI deficiency, factor XII deficiency, fanconi anemia, giant lymph node hyperplasia, hematologic diseases, hemoglobinopathies, hemoglobinuria, paroxysmal, hemophilia a, hemophilia b, hemorrhagic disease of newborn, histiocytosis, histiocytosis, langerhans-cell, histiocytosis, non-langerhans-cell, job's syndrome, leukopenia, lymphadenitis, lymphangioleiomyomatosis, lymphedema, methemoglobinemia, myelodysplastic syndromes, myelofibrosis, myeloid metaplasia, myeloproliferative disorders, neutropenia, paraproteinemias, platelet storage pool deficiency, polycythemia vera, protein c deficiency, protein s deficiency, purpura, thrombocytopenic, purpura, thrombotic thrombocytopenic, RH-isoimmunization, sarcoidosis, sarcoidosis, spherocytosis, splenic rupture, thalassemia, thrombasthenia, thrombocytopenia, Waldenstrom macroglobulinemia, or Von Willebrand disease.

In some embodiments, the present invention provides a method for treating, reducing the incidence, delaying the onset or progression, or reducing and/or abrogating the symptoms associated with a congenital, hereditary, or neonatal disease in a subject. In one embodiment, the method comprises administering to a subject a composition comprising a compound of this invention and anti-cancer agent, an immunomodulating agent, an antidiabetic agent, an agent treating the cardiovascular system, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, congenital, hereditary, and neonatal diseases comprise Aicardi syndrome, amniotic band syndrome, anencephaly, Angelman syndrome, ataxia telangiectasiai, Bannayan-Zonana syndrome, Barth syndrome, basal cell nevus syndrome, Beckwith-Wiedemann syndrome, bloom syndrome, branchio-oto-renal syndrome, cat eye syndrome, cerebral gigantism-charge syndrome, chromosome 16 abnormalities, chromosome 18 abnormalities, chromosome 20 abnormalities, chromosome 22 abnormalities, Costello syndrome, cri-du-chat syndrome, Currarino syndrome, cystic fibrosis, de-Lange syndrome, distal trisomy 10q, down syndrome, ectodermal dysplasia, fetal alcohol syndrome, fetal diseases, fetofetal transfusion, fragile x syndrome, Freeman-Sheldon syndrome, gastroschisis, genetic diseases, inborn, hernia, umbilical, holoprosencephaly, incontinentia pigmenti, Ivemark syndrome, Jacobsen syndrome, jaundice, Klinefelter syndrome, Larsen syndrome, Laurence-moon syndrome, lissencephaly, microcephaly, monosomy 9p, nail-patella syndrome, neurofibromatoses, neuronal ceroid-lipofuscinosis, Noonan syndrome, ochoa syndrome (urofacial syndrome, hydronephrosis with peculiar facial expression), oculocerebrorenal syndrome, Pallister-Killian syndrome, Prader-Willi syndrome, proteus syndrome, prune belly syndrome, Rett syndrome, Robinow syndrome, Rubinstein-Taybi syndrome, schizencephaly, situs inversus, Smith-Lemli-Opitz syndrome, Smith-Magenis syndrome, Sturge-Weber syndrome, syphilis, congenital, trichothiodystrophy, triple-x females, trisomy 13 (Patau syndrome), trisomy 9, turner syndrome, twins, conjoined, Usher syndrome, Waardenburg's syndrome, Werner syndrome, or Wolf-Hirschhorn syndrome.

In some embodiments, the present invention provides a method for treating, reducing the incidence, delaying the onset or progression, or reducing and/or abrogating the symptoms associated with a connective tissue disease in a subject. In one embodiment, the method comprises administering to a subject a composition comprising a compound of this invention and anti-cancer agent, an immunomodulating agent, an agent treating a dermatological disorder, an anti-infective agent, an agent treating a metabolic disease, an agent treating a wasting disease, a gene therapy agent, an agent treating the endocrine system, vitamins, or a combination thereof. In some embodiments, connective tissue diseases comprise ankylosing spondylitis, Ehlers-Danlos syndrome, Henoch-Schonlein purpura, Kawasaki disease, Marfan syndrome, polyarteritis nodosa, polymyositis, psoriatic arthritis, reactive arthritis, rheumatoid arthritis, scleroderma, Sjogren's syndrome, xerophthalmia, Still's disease, systemic lupus erythematosus, Takayasu disease, or Wegener's granulomatosis.

In some embodiments, the present invention provides a method for treating, reducing the incidence, delaying the onset or progression, or reducing and/or abrogating the symptoms associated with a metabolic disease in a subject. In one embodiment, the method comprises administering to a subject a composition comprising a compound of this invention and antidiabetic agent, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, metabolic diseases comprise acid-base imbalance, acidosis, alkalosis, alkaptonuria, alpha-mannosidosis, amino acid metabolism inborn errors, amyloidosis, iron-deficiency anemia, ascorbic acid deficiency, avitaminosis, beriberi, biotinidase deficiency, carbohydrate-deficient glycoprotein syndrome, carnitine disorders, cystinosis, cystinuria, dehydration, fabry disease, fatty acid oxidation disorders, fucosidosis, galactosemias, Gaucher disease, Gilbert disease, glucosephosphate dehydrogenase deficiency, glutaric acidemia, glycogen storage disease, Hartnup disease, hemochromatosis, hemosiderosis, hepatolenticular degeneration, histidinemia, homocystinuria, hyperbilirubinemia, hypercalcemia, hyperinsulinism, hyperkalemia, hyperlipidemia, hyperoxaluria, hypervitaminosis A, hypocalcemia, hypoglycemia, hypokalemia, hyponatremia, hypophosphatasia, insulin resistance, iodine deficiency, iron overload, jaundice, chronic idiopathic, leigh disease, lesch-nyhan syndrome, leucine metabolism disorders, lysosomal storage diseases, magnesium deficiency, maple syrup urine disease, Melas syndrome, Menkes kinky hair syndrome, metabolic diseases, metabolic syndrome x, metabolism, inborn errors, mitochondrial diseases, mucolipidoses, mucopolysaccharidoses, Niemann-Pick diseases, obesity, ornithine carbamoyltransferase deficiency disease, osteomalacia, pellagra, peroxisomal disorders, phenylketonurias, porphyria, erythropoietic, porphyrias, progeria, pseudo, gaucher disease, refsum disease, Reye syndrome, rickets, Sandhoff disease, starvation, tangier disease, Tay-Sachs disease, tetrahydrobiopterin deficiency, trimethylaminuria, tyrosinemias, urea cycle disorders, water-electrolyte imbalance, Wernicke encephalopathy, vitamin A deficiency, vitamin B12 deficiency, vitamin B deficiency, Wolman disease, or Zellweger syndrome.

In some embodiments, the present invention provides a method for treating, reducing the incidence, delaying the onset or progression, or reducing and/or abrogating the symptoms associated with a disorder of environmental origin in a subject. In one embodiment, the method comprises administering to a subject a composition comprising a compound of this invention and anti-cancer agent, an immunomodulating agent, an antidiabetic agent, an agent treating the cardiovascular system, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, disorders of environmental origin comprise barotrauma, bites and stings, brain concussion, burns, central cord syndrome, craniocerebral trauma, electric injuries, fractures, bone, frostbite, heat stress disorders, motion sickness, occupational diseases, poisoning, shaken baby syndrome, shoulder injuries, space motion sickness, spinal cord injuries, tick paralysis, or wounds (penetrating and non-penetrating).

In some embodiments, the present invention provides a method for treating, reducing the incidence, delaying the onset or progression, or reducing and/or abrogating the symptoms associated with a behavior mechanism in a subject. In one embodiment, the method comprises administering to a subject a composition comprising a compound of this invention and an agent treating the cardiovascular system, an agent treating the central nervous system, a gene therapy agent, an agent treating the endocrine system, vitamins, or a combination thereof. In some embodiments, behavior mechanisms comprise aggression, attitude to death, codependency, self-injurious behavior, sexual behavior, or social behavior.

In some embodiments, the present invention provides a method for treating, reducing the incidence, delaying the onset or progression, or reducing and/or abrogating the symptoms associated with a mental disorder in a subject. In one embodiment, the method comprises administering to a subject a composition comprising a compound of this invention and an agent treating the central nervous system, a gene therapy agent, an agent treating the endocrine system, vitamins, or a combination thereof. In some embodiments, mental disorders comprise Asperger syndrome, attention deficit disorder with hyperactivity, autistic disorder, bipolar disorder, borderline personality disorder, capgras syndrome, child behavior disorders, combat disorders, cyclothymic disorder, dependent personality disorder, depressive disorder, dissociative disorders, dysthymic disorder, eating disorders, fire-setting behavior, hypochondriasis, impulse control disorders, Kleine-Levin syndrome, mental disorders, mental disorders diagnosed in childhood, multiple personality disorder, Munchausen syndrome, Munchhausen syndrome, narcissistic personality disorder, narcolepsy, obsessive-compulsive disorder, paraphilias, phobic disorders, psychotic disorders, restless legs syndrome, schizophrenia, seasonal affective disorder, sexual and gender disorders, sexual dysfunctions, psychological, sleep disorders, somatoform disorders, stress disorders, post-traumatic, substance-related disorders, suicidal behavior, or trichotillomania.

In one embodiment, "depression" refers to an illness that involves the body, mood and thoughts that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

In one embodiment, "cognition" refers to the process of knowing, specifically the process of being aware, knowing, thinking, learning and judging. Cognition is related to the fields of psychology, linguistics, computer science, neuroscience, mathematics, ethology and philosophy. In one embodiment, "mood" refers to a temper or state of the mind. As contemplated herein, alterations mean any change for the positive or negative, in cognition and/or mood.

In some embodiments, the present invention provides a method for treating, reducing the incidence, delaying the onset or progression, or reducing and/or abrogating the symptoms associated with a liver disease in a subject. In one embodiment, the method comprises administering to a subject a composition comprising a compound of this invention and anti-cancer agent, an immunomodulating agent, an agent treating the gastrointestinal system, an anti-infective agent, an agent treating the liver, an agent treating a metabolic disease, an agent treating a wasting disease, a gene therapy agent, an agent treating the endocrine system, vitamins, or a combination thereof. In some embodiments, liver diseases comprise liver cancer, primary biliary cirrhosis, autoimmune hepatitis, chronic liver disease, cirrhosis of the liver, hepatitis, viral hepatitis (hepatitis a, hepatitis b, chronic hepatitis b, hepatitis c, chronic hepatitis c, hepatitis d, hepatitis e, hepatitis x), liver failure, jaundice, neonatal jaundice, hepatoma, liver cancer, liver abscess, alcoholic liver disease, hemochromatosis, Wilson's disease, portal hypertension, primary sclerosing cholangitis, sarcoidosis, tapeworms, alveolar hydatid disease, fascioliasis, schistosomiasis, gaucher disease, Zellweger syndrome, alcoholism, food poisoning, pneumococcal pneumonia' or *vibrio* vulnificus.

In some embodiments, the present invention provides a method for treating, reducing the incidence, delaying the onset or progression, or reducing and/or abrogating the symptoms associated with a kidney disease in a subject. In one embodiment, the method comprises administering to a subject a composition comprising a compound of this invention and anti-cancer agent, an immunomodulating agent, an antidiabetic agent, an agent treating the gastrointestinal system, an anti-infective agent, an agent treating the kidney, an agent treating a metabolic disease, a gene therapy agent, an agent treating the endocrine system, vitamins, or a combination thereof. In some embodiments, kidney diseases comprise acromegaly, acute renal failure (ARF) amyloidosis, autosomal dominant polycystic kidney disease, kidney stones, kidney cysts, autosomal recessive polycystic kidney disease, chronic renal failure (CRF), chronic renal disease, coffin-Lowry syndrome, cor pulmonale, cryoglobulinemia, diabetic nephropathy, dyslipidemia, Gaucher disease, glomerulonephritis, goodpasture syndrome, hemolytic uremic syndrome, hepatitis, kidney cancer, kidney stones, leukemia, lipoproteinemia, lupus, multiple myeloma, nephritis, polyartekidney cysts, post streptococcal glomerulonephritis, glomerulonephritis, kidney pain, preeclampsia, renal tuberculosis, pyelonephritis, renal tubular acidosis kidney disease, streptococcal toxic shock syndrome, thromboembolism, toxoplasmosis, urinary tract infections, vesicoureteral reflux, or williams syndrome.

In one embodiment, the kidney disease or disorder is acute, or in another embodiment, chronic. In one embodiment, clinical indications of a kidney disease or disorder, wherein the methods of treatment may be useful include urinary casts, measured GFR, or other markers of renal function.

In one embodiment, the methods of this invention are useful in subjects predisposed to kidney diseases or disorders. In one embodiment, the phrase "predisposed to a kidney disease or disorder" with respect to a subject is synonymous with the phrase "subject at risk", and includes a subject at risk of acute or chronic renal failure, or at risk of the need for renal replacement therapy, if the subject is reasonably expected to suffer a progressive loss of renal function associated with progressive loss of functioning nephron units. Whether a particular subject is at risk is a determination which may routinely be made by one of ordinary skill in the relevant medical or veterinary art.

In one embodiment, subjects with kidney disease, in particular male subjects with end-stage renal disease (ESRD) suffer from hypogonadism, with some having concomitant moderate to severe protein-energy malnutrition (PEM), which leads to higher required doses of EPO, lower QOL scores, and higher mortality. Many have other symptoms associated with hypogonadism, including fatigue, lack of apetite, muscle weakness, etc. In some embodiments, the treatment methods of this invention are useful in treating symptoms associated with hypogonadism, brought about in the subject by androgen deficiency in a female (ADIF); androgen deficiency in aging male (ADAM) to include fatigue, depression, decreased libido, erectile dysfunction, decreased cognition, decreased mood; androgen insufficiency (male or female), androgen deficiency (male or female).

In one embodiment, diabetic nephropathy is a complication of diabetes that evolves early, typically before clinical diagnosis of diabetes is made. The earliest clinical evidence of nephropathy is the appearance of low but abnormal levels (>30 mg/day or 20 μg/min) of albumin in the urine (microalbuminuria), followed by albuminuria (>300 mg/24 h or 200 μg/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over a course of times, which may be several years, resulting in End Stage Renal Disease (ESRD) in diabetic individuals.

Hypertension is another comorbid factor for renal disease. In some embodiments, treatment of renal disease according to the present invention may comprise concomitant treatment with a compound of this invention and an agent which treats hypertension.

In some embodiments, the present invention provides a method for treating, reducing the incidence, delaying the onset or progression, or reducing and/or abrogating the symptoms associated with a wasting disease in a subject. In one embodiment, the method comprises administering to a subject a composition comprising a compound of this invention and anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, vitamins, or a combination thereof. In some embodiments, wasting diseases comprise muscle injury, bed rest, immobility, nerve injury, neuropathy, diabetic neuropathy, alcoholic neuropathy, subacute combined degeneration of the spinal cord, diabetes, rheumatoid arthritis, motor neurone diseases, Duchenne muscular dystrophy, carpal tunnel syndrome, chronic infection, tuberculosis, Addison's disease, adult sma, limb muscle atrophy, alcoholic neuropathy, anorexia, anorexia nervosa, anorexia associated with cachexia, anorexia associated with aging, back tumour, dermatomyositis, hip cancer, inclusion body myositis, incontinentia pigmenti, intercostal neuralgia, juvenile rheumatoid arthritis, Legg-Calve-Perthes disease, muscle atrophy, multifocal motor neuropathy, nephrotic syndrome, osteogenesis imperfecta, post-polio syndrome, rib tumor, spinal muscular atrophy, reflex sympathetic dystrophy syndrome, or Tay-Sachs.

A wasting condition or disorder is defined herein as a condition or disorder that is characterized, at least in part, by an abnormal, progressive loss of body, organ or tissue mass. A wasting condition can occur as a result of a pathology such as, for example, cancer, or it can be due to a physiologic or metabolic state, such as disuse deconditioning that can occur, for example, due to prolonged bed rest or when a limb is immobilized, such as in a cast, or with the occurrence of multiple wounds, including, for example, amputation, as occurs in diabetics, and other conditions, as will be appreciated by one skilled in the art. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, the terms "muscle wasting" or "muscular wasting", refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of pathology, disease, condition or disorders, including disorders for treatment via the methods of this invention, such as, for example, end stage renal failure.

In some embodiments, the present invention provides a method for prevention of statin induced rhabdomyolysis. In some embodiments, the present invention provides a method for prevention of statin induced rhabdomyolysis, organ failure or insufficiency. In some embodiments, the present invention provides a method for prevention of statin induced kidney or liver failure or insufficiency. In one embodiment, the method comprises administering to a subject a composition comprising a compound of this invention and a statin.

In one embodiment, the wasting disease is cachexia or involuntary weight loss in a subject. In another embodiment, the present invention provides a method of treating, preventing, inhibiting, reducing or suppressing muscle wasting in a subject suffering from a kidney disease. In one embodiment, the present invention provides a method of treating, preventing, inhibiting, reducing or suppressing protein catabolism in a subject suffering from a kidney disease or disorder, Cachexia is weakness and a loss of weight caused by a disease or as a side effect of illness. Long term hospitalization due to illness or injury, or disuse deconditioning that occurs, for example, when a limb is immobilized, can also lead to muscle wasting. Studies have shown that in patients suffering injuries, chronic illnesses, burns, trauma or cancer, who are hospitalized for long periods of time, there is a long-lasting unilateral muscle wasting, with a consequent decrease in body mass. Nervous system injury, for example, spinal cord injury, as described further herein, may be a contributory factor, as well.

In some embodiments, the present invention provides a method for treating, reducing the incidence, delaying the onset or progression, or reducing and/or abrogating the symptoms associated with a wasting diseases or disorders in a subject. In another embodiment, the wasting diseases and disorders include inter-alia: a) acquired immunodeficiency syndrome (AIDS) wasting; b) wasting associated with bed rest; c) bulimia, and/or wasting associated with bulimia; c) cachexia; d) cancer cachexia; e) HIV wasting; f) reduce cachexia and protein loss due to prolonged critical illness, pulmonary dysfunction, ventilator dependency, aging, AIDS, trauma, surgery, congestive heart failure, cardiac myopathy, burns, cancer, chronic obstructive pulmonary disease (COPD), eating disorders such bulimia, anorexia nervosa, loss of appetite, starvation, and/or depression.

In some embodiments, the present invention provides a method for treating, reducing the incidence, delaying the onset or progression, or reducing and/or abrogating the symptoms associated with invalid states in a subject. In one embodiment, the invalid state is post-polio syndrome. In one embodiment, the method comprises administering to a subject a composition comprising a compound of this invention and an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, vitamins, or a combination thereof.

In some embodiments, the present invention provides a method for treating, reducing the incidence, delaying the onset or progression, or reducing and/or abrogating the symptoms associated with a hypogonadal state in a subject. In one embodiment, the present invention provides a method for treating, reducing the incidence, delaying the onset or progression, or reducing and/or abrogating the symptoms associated with a pharmacotherapy induced hypogonadal state in a subject. In some embodiments, hypogonadism is caused by treatments which alter the secretion of hormones from the sex glands in both women and men. In some embodiments, hypogonadism may be "primary" or "central". In primary hypogonadism, the ovaries or testes themselves do not function properly. In some embodiments, hypogonadism may be induced by surgery, radiation, genetic and developmental disorders, liver and kidney disease, infection, or certain autoimmune disorders. In some embodiments, menopause is a form of hypogonadism. Menopause may cause, in some embodiments, amenorrhea, hot flashes, vaginal dryness, or irritability due to woman's estrogen levels fall. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

In some embodiments, the present invention provides a method for treating, reducing the incidence, delaying the onset or progression, or reducing and/or abrogating the symptoms associated with osteopenic state in a subject. In one embodiment, the present invention provides a method for treating, reducing the incidence, delaying the onset or progression, or reducing and/or abrogating the symptoms associated with a pharmacotherapy induced osteopenic state in a subject. In some embodiments, osteopenia is a mild thinning of the bone mass. In some embodiments, osteopenia is a precursor to osteoporosis. In some embodiments osteopenia is defined as a bone density between one standard deviation (SD) and 2.5 SD below the bone density of a normal young adult. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

In some embodiments, the present invention provides a method for treating, reducing the incidence, delaying the onset or progression, or reducing and/or abrogating the symptoms associated with a sarcopenic state in a subject. In one embodiment, the present invention provides a method for treating, reducing the incidence, delaying the onset or progression, or reducing and/or abrogating the symptoms associated with a pharmacotherapy induced sarcopenic state in a subject. In some embodiments, sarcopenia is a significant loss of muscle mass. In one embodiment, sarcopenia definition is having a lean body mass less than two standard deviation below the mean for normal young adults. In some embodiments, sarcopenia is caused by genetic factors, altered circulation, decrease in the capillary:muscle fiber ratio, altered motor neurons, denervation, deterioration of motor end plates, selective reinnervation of Type I fibers, inflammatory responses causing muscle damage, reduced exercise, malnutrition, low dietary protein intake, vitamin D deficiency, age-related decline in vitamin D, oxidative stress, muscle mitochondrial mutations, changes in specific types of muscle fibers, decline in muscle protein, disabling disease, strokes, Alzheimer's disease, Parkinson's disease, osteoporsis, atherosclerosis, diabetes mellitus, hyperinsulimemia, renal failure, or hypogonadism. In one embodiment, the method comprises administering to a subject a composition comprising a SARM compound and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

In some embodiments, the present invention provides a method for treating, reducing the incidence, delaying the onset or progression, or reducing and/or abrogating the symptoms associated with a combination of diseases and/or disorders in a subject as described hereinabove. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

It is to be understood that any method of this invention, as herein described, encompasses the administration of a compound as herein described, or a composition comprising the same, to the subject, in order to treat the indicated disease, disorder or condition. The methods as herein described each and/or all may further comprise administration of an additional therapeutic agent as herein described, and as will be appreciated by one skilled in the art.

In some embodiments, the present invention provides a method for enhanced production such as milk, sperm, or egg. In some embodiments, the present invention provides a method for enhanced production of lean meats or eggs. In some embodiments, the present invention provides a method for increased productivity of feeds or stud livestock, for example, increased sperm count, improved morphology of sperm, etc. In some embodiments, the present invention provides a method for expanding the productive life of farm animals, for example, egg-laying hens, milk-producing cows, etc, and/or enhanced herd health, for example, improved immune clearance, stronger animals.

In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, nutritional additives, hormones, each and/or all as herein described, or any other therapeutic agent as herein described, or a combination thereof.

In another embodiment, this invention provides methods of treatment of cystic fibrosis and induced hypogonadal states as a result of the same, epilepsy and induced hypogonadal and/or hypermetabolic states as a result of the same, hereditary angioedema, lupus erythematosus and decreased BMD as a result of the same, alcohol and smoking induced osteoporosis, in a subject the methods comprising administering a SARM as herein described to the subject.

In another embodiment, this invention provides methods of treatment of polio and post-polio syndrome and other invalid states, statin induced rhabdomyolysis, statin-induced muscle weakness, statin-induced organ failure or insufficiency, in a subject, the methods comprising the administration of a compound as herein described, optionally with a statin, as appropriate, as will be appreciated by one skilled in the art, and/or with any therapeutic agent.

In another embodiment, this invention provides a method of treating Opioid Induced Androgen Deficiency (OPIAD), the method comprising administering to the subject a compound as herein described, and optionally opiates, opioids, narcotics, etc. methadone, long-acting opiates/opioids such as Kadian, extended release morphines, all opiates/opioids/narcotics agents approved by FDA, opiates/opioids used in treatment of heroin addiction, opiates/opioids used in the treatment of chronic pain of malignancy, opiates/opioids used in the treatment non-malignant of chronic pain syndromes.

In another embodiment, this invention provides a method of treating a nervous system disease, disorder or condition, the method comprising administering to the subject a compound as herein described, and optionally anti-psychotics, such as, for example, zotepine, haloperidol, amisulpride, risperidone, other D2 dopamine receptor antagonists; anti-epileptics, such as valproic acid, carbamazepine, oxcarbamazepine, etc. or combinations thereof.

In another embodiment, this invention provides a method of treating a hormone dependent disease, disorder or condition, the method comprising administering to the subject a compound as herein described, and optionally chemotherapeutics agents and therapies (methotrexate, cyclophosphamide, ifosfamide, adriamycin, doxorubicin, glucocorticoids, cyclosporine, L-thyroxine, SERMs, AI, fulvestrant, GnRH agents, ADT, discontinuation of hormone replacement therapy, cranial irradiation, peripheral irradiation, etc.; prolactinemia-inducing pharmacotherapeutics (serotonergic antidepressants acting through 5HT2 receptors, selective serotonin reuptake inhibitors, monoamine oxidase inhibitors, tricyclic antidepressants, antihypertensives such as methyldopa, reserpine, clonidine, and verapamil; antidopaminergic anti-emetics such as metoclopramide, H2 receptor antagonists such as cimetidine and ranitidine, estrogens, amphetamines, AR partial antagonists (ketoconazole, spironolactone, eplerenone)

In another embodiment, the compounds of this invention and compositions as described herein are useful in promoting or speeding recovery following a surgical procedure.

In one embodiment, the present invention provides a use of a compound as described herein for reducing a fat mass in a subject. In another embodiment the invention provides such methods for use of the compound as described herein or its prodrug, analog, isomer, metabolite, derivative, pharmaceutically acceptable salt, pharmaceutical product, polymorph, crystal, impurity, N-oxide, hydrate or any combination thereof, or a composition comprising the same.

In another embodiment, this invention provides for the use of a compound as described herein or its prodrug, analog, isomer, metabolite, derivative, pharmaceutically acceptable salt, pharmaceutical product, polymorph, crystal, impurity, N-oxide, hydrate or any combination thereof, or a composition comprising the same, in treating abdominal fat accumulation; improving body composition; lowering body fat content; lowering fat mass; improving blood lipid profile, increasing muscle mass/strength/function; increasing bone mass/BMD/strength/function; lowering body fat; congenital hyperinsulinemia; cushing's disease (hypercortisolemia); obesity or diabetes associated with a metabolic syndrome in a subject.

In another embodiment, the subject has a hormonal imbalance, disorder, or disease. In another embodiment the subject has menopause.

In one embodiment, the present invention provides a use of a compound as described herein for increasing a lean mass in a subject. In another embodiment such use comprises administration of a compound as described herein or its prodrug, analog, isomer, metabolite, derivative, pharmaceutically acceptable salt, pharmaceutical product, polymorph, crystal, impurity, N-oxide, hydrate or any combination thereof.

In one embodiment the subject has a hormonal imbalance, disorder, or disease. In another embodiment the subject has menopause.

Example 4 demonstrates that a compound of formula (II) is anabolic yet minimally androgenic, thus such compounds may be useful in treating patient groups in which androgens were contraindicated in the past. Compound of formula (II) was shown to stimulate muscle growth, whether in the presence or absence of testosterone while exerting anti-proliferative effects on the prostate, thus, in one embodiment, the methods of this invention provide for restoring lost muscle mass in patients with sarcopenia or cachexia.

In one embodiment, the compounds as herein described alter the levels of leptin in a subject. In another embodiment, the compounds as herein described decrease the levels of leptin. In another embodiment, the compounds as herein described increase the levels of leptin in a subject. Leptin is known to have an effect on appetite on weight loss in obese mice, and thus has been implicated in obesity.

The compounds as herein described, in one embodiment, affect circulating, or in another embodiment, tissue levels of leptin. In one embodiment, the term 'level/s of leptin' refers to the serum level of leptin. As contemplated herein, the compounds of the present invention have an effect on leptin in-vitro and in-vivo. Leptin levels can be measured by methods known to one skilled in the art, for example by commercially available ELISA kits. In addition, Leptin levels may be determined in in-vitro assays, or in in-vivo assays, by any method known to a person skilled in the art.

Since leptin is implicated in controlling appetite, weight loss, food intake, and energy expenditure, modulating and/or controlling the levels of leptin is a useful therapeutic approach in treating preventing, inhibiting or reducing the incidence of obesity in subjects suffering from obesity. Modulating the level of leptin can result in a loss of appetite, a reduction of food intake, and an increase in energy expenditure in the subject, and thus may contribute to the control and treatment of obesity.

The term "obesity" is defined, in one embodiment, as an increase in body weight beyond the limitation of skeletal and physical requirement, as the result of excessive accumulation of fat in the body.

The term "obesity-associated metabolic disorder" refers, in one embodiment, to a disorder which results from, is a consequence of, is exacerbated by or is secondary to obesity. Non-limiting examples of such a disorder are osteoarthritis, Type II diabetes mellitus, increased blood pressure, stroke, and heart disease.

Cholesterol, triacylglycerol and other lipids are transported in body fluids by lipoproteins which may be classified according to their density, for example, the very low density lipoproteins (VLDL), intermediate density lipoproteins (HDL), low density lipoproteins (LDL) and high density lipoproteins (HDL).

It has been shown that high levels of LDL-Cholesterol in the blood correlate with atherosclerosis which is a progressive disease characterized in part by sedimentation of lipids in inner walls of arteries, particularly of coronary arteries. It has also been shown that a high blood level of LDL-Cholesterol correlates with coronary heart disease. Also, a negative correlation exists between blood levels of HDL cholesterol and coronary heart disease.

The level of total cholesterol in blood, which is the sum of HDL-Cholesterol, LDL-Cholesterol, VLDL-Cholesterol and chylomicron-Cholesterol, is not necessarily predictive of the risk of coronary heart disease and atherosclerosis.

The correlation between atherosclerosis and LDL cholesterol levels, however, is much higher than a similar correlation between atherosclerosis and total serum cholesterol levels.

In one embodiment, this invention provides methods of use of the compounds as herein described for improving the lipid profile and/or reducing the circulating lipid levels in a subject. In some embodiments, according to this aspect of the invention, the subject suffers from one or more conditions selected from the group consisting of: atherosclerosis and its associated diseases, premature aging, Alzheimer's disease, stroke, toxic hepatitis, viral hepatitis, peripheral vascular insufficiency, renal disease, and hyperglycemia, and the invention provides for the administration of a compound or composition comprising the same, as herein described, which in some embodiments positively affects a lipid profile in the subject, which is one means by which the method is useful in treating the indicated diseases, disorders and conditions.

In one embodiment the invention provides for the treatment of atherosclerosis and its associated diseases, such as for example, cardiovascular disorders, cerebrovascular disorders, peripheral vascular disorders, intestinal vascular disorders, or combinations thereof.

In one embodiment cardiovascular disorders comprise of hypertention (HTN), coronary artery disease (CAD) or myocardial perfusion. In another embodiment this invention provides methods of use of the SARM compounds as herein described for promoting aortic smooth muscle cell proliferation. In another embodiment this invention provides methods of use of the compounds as herein described for treating arteriosclerosis. In another embodiment this invention provides methods of use of the compounds as herein described for lowering blood pressure. In another embodiment this invention provides methods of use of the compounds as herein described for treating cardiac diseases and disorders comprising cardiomyopathy, cardiac dysfunctions such as, myocardial infarction, cardiac hypertrophy and cognitive heart failure. In another embodiment this invention provides methods of use of the compounds as herein described for cardioprotection comprising cardioprotection in insulin resistance; treating diabetes type I and II, metabolic syndrome, syndrome X and/or high blood pressure.

In one embodiment, the invention provides a method of treating, preventing, reducing the risk of mortality from cardiovascular and/or cerebrovascular disease in a subject, comprising administering a compound of this invention or its prodrug, ester, analog, isomer, metabolite, derivative, pharmaceutically acceptable salt, pharmaceutical product, polymorph, crystal, impurity, N-oxide, hydrate or any combination thereof, or a pharmaceutical composition comprising the same. In one embodiment, the compound is characterized by the structure of formula (II).

In one embodiment, compounds of this invention reduce LDL and total cholesterol levels. In another embodiment the compound of formula (II) reduces LDL and total cholesterol levels in a subject. In one embodiment, the compound is characterized by the structure of the formula I-XXII, or any embodiment thereof, as herein described.

In another embodiment, compounds of formulae I are co-administered with HDL-elevating agents. In another embodiment, a compound of this invention is co-administered with an HDL-elevating agents. In another embodiment, HDL-elevating agents include niacin. In another embodiment the HDL-elevating agents include fibrates including gemfibrozil (Lopid), thiourea based gemfibrozil analogues, and fenofibrate (TriCor). In another embodiment, HDL-elevating agents include statins. In another embodiment, HDL-elevating agents include 1-hydroxyalkyl-3-phenylthiourea, and analogs thereof.

In one embodiment, this invention provides a method of reducing circulating lipid levels in a subject, said method comprising administering a compound of this invention or its pharmaceutically acceptable salt, hydrate, N-oxide, or any combination thereof, or a composition comprising the same. In one embodiment, the subject suffers from atherosclerosis and its associated diseases, premature aging, Alzheimer's disease, stroke, toxic hepatitis, viral hepatitis, peripheral vascular insufficiency, renal disease, hyperglycemia, or any combination thereof. In one embodiment, the compound is characterized by the structure of the formula I-XXII, or any embodiment thereof, as herein described.

In one embodiment, this invention provides a method of treating atherosclerosis and its associated diseases, such as, for example, cardiovascular disorders, cerebrovascular disorders, peripheral vascular disorders, or intestinal vascular disorders in a subject, the method comprising the step of administering to the subject compound of this invention or its pharmaceutically acceptable salt, hydrate, N-oxide, or any combination thereof, or a composition comprising the same. In one embodiment, the compound is characterized by the structure of the formula I-XXII, or any embodiment thereof, as herein described.

The method may further comprise co-administration, subsequent or prior administration with an agent or agents, which are known to be useful in treating cardiovascular disorders, cerebrovascular disorders, peripheral vascular disorders, or intestinal vascular disorders.

In one embodiment, this invention provides a method of improving the dexterity and movement in a subject, for example, by treating arthritis in the subject.

The term "arthritis" refers, in another embodiment, to a non-inflammatory degenerative joint disease occurring chiefly in older people, characterized by degeneration of the articular cartilage, hypertrophy of bones and the margins, changes in the synovial membrane, etc. It is accompanied, in other embodiments, by pain and stiffness, particularly after prolonged activity.

The term "diabetes", in one embodiment, refers to a relative or absolute lack of insulin leading to uncontrolled carbohydrate metabolism. Most patients can be clinically classified as having either insulin-dependent diabetes mellitus (IDDM or Type-I diabetes) or non-insulin-dependent diabetes mellitus (NIDDM or Type-II diabetes).

The term "increased blood pressure" or "hypertension" refers, in other embodiments, to a repeatedly high blood pressure above 140 over 90 mmHg. Chronically-elevated blood pressure can cause blood vessel changes in the back of the eye, thickening of the heart muscle, kidney failure, and brain damage.

The term "stroke" refers, in other embodiments, to damage to nerve cells in the brain due to insufficient blood supply often caused by a bursting blood vessel or a blood clot. The term "heart disease", in other embodiments, refers to a malfunction in the heart normal function and activity, including heart failure.

In addition, androgens have recently been shown to be involved in commitment of mesenchymal pluripotent cells into myogenic lineage and to block differentiation into adipogenic lineage (Singh et al., Endocrinology, 2003, Jul. 24). Accordingly, the compounds can be useful in methods of blocking adipogenesis, and/or altering stem cell differentiation, as described herein.

In another embodiment, this invention relates to a method of promoting, increasing or facilitating weight loss in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to promote, increase or facilitate weight loss in the subject.

In another embodiment, this invention relates to a method of decreasing, suppressing, inhibiting or reducing appetite of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce the appetite of the subject.

In another embodiment, this invention relates to a method of altering the body composition of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the body composition of the subject. In one embodiment, altering the body composition comprises altering the lean body mass, the fat free body mass of the subject, or a combination thereof.

In another embodiment, this invention relates to a method of altering lean body mass or fat free body mass of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the lean body mass or fat free body mass of the subject.

In another embodiment, this invention relates to a method of converting fat to lean muscle in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to convert fat to lean muscle in the subject.

In another embodiment, this invention relates to a method of treating an obesity-associated metabolic disorder in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to treat the obesity-associated metabolic disorder in the subject.

In another embodiment, this invention relates to a method of preventing, suppressing, inhibiting or reducing an obesity-associated metabolic disorder in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the obesity-associated metabolic disorder in the subject.

In one embodiment, the obesity-associated metabolic disorder is hypertension. In another embodiment, the disorder is osteoarthritis. In another embodiment, the disorder is Type II diabetes mellitus. In another embodiment, the disorder is increased blood pressure. In another embodiment, the disorder is stroke. In another embodiment, the disorder is heart disease.

In another embodiment, this invention relates to a method of decreasing, suppressing, inhibiting or reducing adipogenesis in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof.

In another embodiment, this invention relates to a method of altering stem cell differentiation in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter stem cell differentiation in the subject.

In one embodiment, the compounds as herein described are useful in a) treating, preventing, suppressing, inhibiting, or reducing obesity; b) promoting, increasing or facilitating weight loss; c) decreasing, suppressing, inhibiting or reducing appetite; d) altering the body composition; e) altering lean body mass or fat free body mass; f) converting fat to lean muscle; g) treating, preventing, suppressing, inhibiting, or reducing an obesity-associated metabolic disorder, for example hypertension, osteoarthritis, diabetes mellitus, MODY, increased blood pressure, stroke, or heart disease; h) decreasing, suppressing, inhibiting or reducing adipogenesis; i) altering stem cell differentiation; and/or j) altering the level of leptin.

In one embodiment, the compounds as herein described find utility in treating or halting the progression of, or treating symptoms of diabetes. In another embodiment, the compounds as herein described are useful in treating co-morbidities related to diabetes. These conditions include: hypertension (HTN), cerebrovascular disease, atherosclerotic coronary artery disease, macular degeneration, diabetic retinopathy (eye disease) and blindness, cataracts—systemic inflammation (characterized by elevation of inflammatory markers such as erythrocyte sedimentation rate or C-reactive protein), birth defects, pregnancy related diabetes, pre-eclampsia and hypertension in pregnancy, kidney disease (renal insufficiency, renal failure etc.), nerve disease (diabetic neuropathy), superficial and systemic fungal infections, congestive heart failure, gout/hyperuricemia, obesity, hypertriglyceridemia, hypercholesterolemia, fatty liver disease (nonalcoholic steatohepatitis, or NASH), and diabetes-related skin diseases' such as Necrobiosis Lipoidica Diabeticorum (NLD), Blisters of diabetes (Bullosis Diabeticorum), Eruptive Xanthomatosis, Digital Sclerosis, Disseminated Granuloma Annulare, and Acanthosis Nigricans.

In one embodiment this invention provides a method of treating, suppressing, inhibiting or reducing the incidence of (a) diabetes type I; (b) diabetes type II; (c) glucose intolerance; (d) hyperinsulinemia; (e) insulin resistance (f) nephropathy; (g) diabetic neuropathy; (h) diabetic retinopathy (i) fatty liver conditions (j) MODY and (k) cardiovascular disease in a human subject, comprising the step of administering to said subject a compound of this invention. In one embodiment, the compound is characterized by the structure of the formula I-XXII, or any embodiment thereof, as herein described.

In some embodiments, the compounds as herein described and/or compositions comprising the same may be used for applications in, or treating diseases or conditions associated with a subject having diabetes. In one embodiment, the subject for whom treatment is sought via the methods of this invention is one with diabetic I. Type I diabetes is characterized by autoimmune destruction of pancreatic beta-cells. Markers of immune destruction of the beta-cell are present at the time of diagnosis in 90% of individuals and include antibodies to the islet cell (ICAs), to glutamic acid decarboxylase (GAD), and to insulin (IAAs). While this form of diabetes usually occurs in children and adolescents, it can occur at any age. Younger individuals typically have a rapid rate of beta-cell destruction and present with ketoacidosis, while adults often maintain sufficient insulin secretion to prevent ketoacidosis for many years. Eventually, all type I diabetic patients require insulin therapy to maintain normglycemia.

In one embodiment, this invention provides a method of treating diabetes type II. Type II diabetes is characterized by insulin resistance and at some stage in pathogenesis of the disease, a relative deficiency of insulin secretion. In absolute terms, the plasma insulin concentration (both fasting and meal-stimulated) usually is increased, although "relative" to the severity of insulin resistance, the plasma insulin concentration is insufficient to maintain normal glucose homeostasis. With time, however, there is progressive beta cell failure and absolute insulin deficiency ensues. Most individuals with type II diabetes exhibit intra abdominal (visceral) obesity, fatty liver, which is closely related to the presence of insulin resistance. The patient's liver becomes insulin resistant and glycogen breakdown is uncontrolled and the result is increased and unphysiological glucose delivery to the bloodstream. The liver generated cholesterol and VLDL particles is also uncontrolled. In addition, hypertension, dyslipidemia (high triglyceride and low HDL-cholesterol levels; postprandial hyperlipemia), and elevated PAI-1 levels often are present in these individuals. This clustering of abnormalities is referred to as the "insulin resistance syndrome", or the "metabolic syndrome" or obesity related disorders. Because of these abnormalities, patients with type II diabetes are at increased risk of developing macrovascular complications such as myocardial infarction and stroke.

In one embodiment, this invention provides a method of treating diabetic nephropathy. Diabetic nephropathy is a complication of diabetes that evolves early, typically before clinical diagnosis of diabetes is made. The earliest clinical evidence of nephropathy is the appearance of low but abnormal levels (>30 mg/day or 20 µg/min) of albumin in the urine (microalbuminuria), followed by albuminuria (>300 mg/24 h or 200 µg/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over a course of times, which may be several years, resulting in End Stage Renal Disease (ESRD) in diabetic individuals.

In one embodiment, this invention provides a method of treating diabetic neuropathy. Diabetic neuropathy is a family of nerve disorders caused by diabetes. Diabetic neuropathies cause numbness and sometimes pain and weakness in the hands, arms, feet, and legs. Neurologic problems in diabetes may occur in every organ system, including the digestive tract, heart, and genitalia. Diabetic neuropathies are classified as peripheral, autonomic, proximal, and focal. Peripheral neuropathy causes pain or loss of feeling in the toes, feet, legs, hands, and arms. Autonomic neuropathy causes changes in digestion, bowel and bladder function, sexual response, and perspiration and can also affect the nerves that serve the heart and control blood pressure. Proximal neuropathy causes pain in the thighs, hips, or buttocks and leads to weakness in the legs. Focal neuropathy results in the sudden weakness of one nerve, or a group of nerves, causing muscle weakness or pain. Any nerve in the body may be affected.

In one embodiment, this invention provides a method of treating diabetic retinopathy. The effect of diabetes on the eye is called diabetic retinopathy. Patients with diabetes are more likely to develop eye problems such as cataracts and glaucoma. The affect of diabetic retinopathy on vision varies widely, depending on the stage of the disease. Some common symptoms of diabetic retinopathy are blurred vision (this is often linked to blood sugar levels), floaters and flashes and sudden loss of vision.

In one embodiment, the subject for whom treatment is sought via the methods of this invention is one with glucose intolerance. Glucose intolerance is a pre-diabetic state in which the blood glucose is higher than normal but not high enough to warrant the diagnosis of diabetes.

In one embodiment, the subject for whom treatment is sought via the methods of this invention is one with hyperinsulinemia. Hyperinsulinemia is a sign of an underlying problem that is causing the pancreas to secrete excessive amounts of insulin. The most common cause of hyperinsulinemia is insulin resistance, a condition in which your body is resistant to the effects of insulin and the pancreas tries to compensate by making more insulin. hyperinsulinemia is associated with type II diabetes In one embodiment, the subject for whom treatment is sought via the methods of this invention is one with insulin resistance. Insulin resistance is a condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to the metabolic syndrome and type It diabetes.

Diabetes and the liver obesity is typically associated with elevated levels of free fatty acid (FFAs) that promote lipid accumulation and insulin resistance in target tissues, i.e. reduced action of insulin primarily in skeletal muscle and liver. A prominent role of insulin is to reduce glucose output from the liver. FFAs stimulate hepatic gluconeogenesis which per se does not lead to increased hepatic glucose output as long as it is paralleled by a decrease in hepatic glycogenolysis, a compensatory process referred to as "hepatic autoregulation". FFAs stimulate insulin secretion and insulin blocks glycogenolysis in part by inhibiting secretion of glucagon, an inducer of glycogenolysis. However, long-term elevated levels of FFAs leads to hepatic insulin resistance and thus breakdown of hepatic autoregulation, resulting in increased hepatic glucose production and development of type II diabetes. Fatty liver and hepatic insulin resistance is a major driving force behind hyperglycemia and type II diabetes.

In one embodiment, this invention provides methods that inhibit (improve) the fatty liver, resulting in that the insulin resistance in the liver is inhibited (improved) and thereby solving the basic problem in type II diabetes.

In another embodiment, the diabetes is a type I diabetes. In another embodiment, the diabetes is a type II diabetes.

In one embodiment, this invention provides a method of treating suppressing, inhibiting or reducing the incidence of diabetes is a human subject, comprising the step of administering to said subject a compound of this invention or its isomer, pharmaceutically acceptable salt, pharmaceutical product, hydrate, N-oxide, or any combination thereof. In one embodiment, the compound is characterized by the structure of the formula I-XXII, or any embodiment thereof, as herein described.

In another embodiment, the diabetes is a Type I diabetes. In another embodiment, the diabetes is a type II diabetes.

In one embodiment, this invention provides a method of treating a human subject having glucose intolerance, comprising the step of administering to said subject compound of this invention or its isomer, pharmaceutically acceptable salt, pharmaceutical product, hydrate, N-oxide, or any combination thereof. In one embodiment, the compound is characterized by the structure of the formula I-XXII, or any embodiment thereof, as herein described.

In one embodiment, this invention provides a method of treating hyperinsulinemia in a human subject, comprising the step of administering to said subject a compound of this invention or its isomer, pharmaceutically acceptable salt, pharmaceutical product, hydrate, N-oxide, or any combination thereof.

In one embodiment, the compound is characterized by the structure of the formula I-XXII, or any embodiment thereof, as herein described.

In one embodiment, this invention provides a method of treating insulin resistance in a human subject, comprising the step of administering to said subject the compound of this invention or its isomer, pharmaceutically acceptable salt, pharmaceutical product, hydrate, N-oxide, or any combination thereof. In one embodiment, the compound is characterized by the structure of the formula I-XXII, or any embodiment thereof, as herein described.

In one embodiment, this invention provides a method of treating diabetic nephropathy in a human subject, comprising the step of administering to said subject a selective androgen receptor modulator compound of this invention or its isomer, pharmaceutically acceptable salt, pharmaceutical product, hydrate, N-oxide, or any combination thereof. In one embodiment, the compound is characterized by the structure of the formula I-XXII, or any embodiment thereof, as herein described.

In one embodiment, this invention provides a method of treating diabetic neuropathy in a human subject, comprising the step of administering to said subject compound of this invention or its isomer, pharmaceutically acceptable salt, pharmaceutical product, hydrate, N-oxide, or any combination thereof. In one embodiment, the compound is characterized by the structure of the formula I-XXII, or any embodiment thereof, as herein described.

In one embodiment, this invention provides a method of treating diabetic retinopathy in a human subject, comprising the step of administering to said subject a compound of this invention or its isomer, pharmaceutically acceptable salt, pharmaceutical product, hydrate, N-oxide, or any combination thereof. In one embodiment, the compound is characterized by the structure of the formula I-XXII, or any embodiment thereof, as herein described.

In one embodiment, this invention provides a method of treating fatty liver conditions in a human subject, comprising the step of administering to said subject a selective androgen receptor modulator compound of this invention or its isomer, pharmaceutically acceptable salt, pharmaceutical product, hydrate, N-oxide, or any combination thereof. In one embodiment, the compound is characterized by the structure of the formula I-XXII, or any embodiment thereof, as herein described.

In one embodiment, this invention provides a method of treating ovascular disease in a human subject, comprising the step of administering to said subject a compound of this invention or its isomer, pharmaceutically acceptable salt, pharmaceutical product, hydrate, N-oxide, or any combination thereof.

In one embodiment, the compound is characterized by the structure of the formula I-XXII, or any embodiment thereof, as herein described.

In one embodiment this invention provides a method for a) treating, preventing, suppressing inhibiting atherosclerosis b) treating, preventing, suppressing inhibiting liver damage due to fat deposits comprising the step of administering to the subject a compound as described herein and/or its analog, derivative, isomer, metabolite, pharmaceutically acceptable salt, pharmaceutical product, hydrate, N-oxide, prodrug, polymorph, crystal, or any combination thereof, or a composition comprising the same, in an amount effective to treat, prevent or inhibit atherosclerosis and liver damage due to fat deposit.

In one embodiment, the compound as described herein is useful in a) treating, preventing, suppressing, inhibiting, or reducing atherosclerosis; b) treating, preventing, suppressing inhibiting liver damage due to fat deposits.

In one embodiment atherosclerosis refers to a slow, complex disease that may begin with damage to the innermost layer of the artery. In another embodiment the causes of damage to the arterial wall may include a) elevated levels of cholesterol and in the blood; b) high blood pressure; c) tobacco smoke d) diabetes. In another embodiment, the condition is treatable in a smoker, despite the fact that tobacco smoke may greatly worsen atherosclerosis and speed its growth in the coronary arteries, the aorta and arteries in the legs. Similarly, in another embodiment, the methods of this invention may be useful in treating subjects with a family history of premature cardiovascular disease who have an increased risk of atherosclerosis.

In one embodiment, liver damage due to fat deposits refer to the build-up of fat in the liver cells forming a Fatty Liver which may be associated with or may lead to inflammation of the liver. This can cause scarring and hardening of the liver. When scarring becomes extensive, it is called cirrhosis.

In another embodiment the fat accumulates in the liver as obesity. In another embodiment fatty liver is also associated with diabetes mellitus, high blood triglycerides, and the heavy use of alcohol. In another embodiment fatty Liver may occur with certain illnesses such as tuberculosis and malnutrition, intestinal bypass surgery for obesity, excess vitamin A in the body, or the use of certain drugs such as valproic acid (trade names: Depakene/Depakote) and corticosteroids (cortisone, prednisone). Sometimes fatty liver occurs as a complication of pregnancy.

In one embodiment, subjects with kidney disease, in particular male subjects with end-stage renal disease (ESRD) suffer from hypogonadism, with some having concomitant moderate to severe protein-energy malnutrition (PEM), which leads to higher required doses of EPO, lower QOL scores, and higher mortality. Many have other symptoms associated with hypogonadism, including fatigue, lack of apetite, muscle weakness, etc. In some embodiments, the treatment methods of this invention are useful in treating symptoms associated with hypogonadism, brought about in the subject by the kidney disease or disorder.

In one embodiment, diabetic nephropathy is a complication of diabetes that evolves early, typically before clinical diagnosis of diabetes is made. The earliest clinical evidence of nephropathy is the appearance of low but abnormal levels (>30 mg/day or 20 µg/min) of albumin in the urine (microalbuminuria), followed by albuminuria (>300 mg/24 h or 200 µg/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over a course of times, which may be several years, resulting in End Stage Renal Disease (ESRD) in diabetic individuals.

Hypertension is another comorbid factor for renal disease. In some embodiments, treatment of renal disease according to the present invention may comprise concomitant treatment with a compound of this invention and an agent which treats hypertension.

Androgen-dependent conditions which may be treated with the compounds and/or compositions as herein described, comprising the methods of the present invention include those conditions which are associated with aging. In one embodiment, the compound as described herein is useful in a) Age-related functional decline (ARFD); b) reversal or prevention of ARFD; c) reversal or prevention of ARFD in elderly d) reversal or prevention of ARFD-induced sarcopenia or osteopenia; e) Andropause, andropausal vasomotor symptoms, f) andropausal gynecomastia, muscle strength/function; g) bone strength/function; h) Anger; i) Asthenia; j) Chronic fatigue syndrome; k) Cognitive impairment; and/or l) improving cognitive function.

In one embodiment, the compound as described herein is useful in treating inflammation and related disorders such as:a) prevention, treatment, or reversal of arthritis; b) prevention, treatment, or reveral of an arthritic condition such as Behcet's disease (autoimmune vasculitis), bursitis, calcium pyrophosphate dihydrate crystal (CPPD), deposition disease (or pseudogout), carpal tunnel syndrome, connective tissue disorders, Crohn's disease, Ehlers-Danlos syndrome (EDS), fibromyalgia, gout, infectious arthritis, inflammatory bowel disease (IBD), juvenile arthritis, systemic lupus erythematosus (SLE), Lyme's disease, Marfan syndrome, myositis, osteoarthritis, polyarteritis nodosa, polymyalgia rheumatica, psoriasis, psoriatic arthritis, Raynaud's phenomenon, reflex sympathetic dystrophy syndrome, Reiter's syndrome, rheumatoid arthritis, scleroderma, Sjögrens' syndrome, tendonitis or ulcerative colitis; c) preventing, treatment, or reversing an autoimmune disease.

In one embodiment, the compound as described herein is useful in prevention of iatrogenic effects comprising acute fatigue syndrome (post-surgical) or androgen-deprivation therapy (ADT) induced side effects such as reduced muscle mass, reduced muscle strength, frailty, hypogonadism, osteoporosis, osteopenia, decreased BMD and/or decreased bone mass.

In one embodiment, the compounds and/or compositions and/or methods of use thereof are for the treatment of human subjects, wherein, in one embodiment, the subject is male, or in another embodiment, the subject is female.

In one embodiment, the methods of the present invention comprise administering a compound of this invention as the sole active ingredient. However, also encompassed within the scope of the present invention are methods for diabetes and related disorders, hormone therapy, dry eye, obesity, treating prostate cancer, delaying the progression of prostate cancer, and for preventing and/or treating the recurrence of prostate cancer, male contraception; treatment of osteoporosis, treatment of conditions associated with ADIF and for treatment and/or prevention of chronic muscular wasting which comprise administering the compounds in combination with one or more therapeutic agents. These agents include, but are not limited to: LHRH analogs, reversible antiandrogens, antiestrogens, anticancer drugs, 5-alpha reductase inhibitors, aromatase inhibitors, progestins, agents acting through other nuclear hormone receptors, selective estrogen receptor modulators (SERM), progesterone, estrogen, PDE5 inhibitors, apomorphine, bisphosphonate, and one or more additional SARMs.

Thus, in one embodiment, the methods of the present invention comprise administering the compound of this invention in combination with diabetes drug such as Troglitazone, Rosiglitazone, and Pioglitazone. In another embodiment, the methods of the present invention comprise administering the compound in combination with an LHRH analog. In another embodiment, the methods of the present invention comprise administering the compound, in combination with a reversible antiandrogen. In another embodiment, the methods of the present invention comprise administering the compound, in combination with an antiestrogen. In another embodiment, the methods of the present invention comprise administering the compound, in combination with an anticancer drug. In another embodiment, the methods of the present invention comprise administering the compound, in combination with a 5-alpha reductase inhibitor. In another embodiment, the methods of the present invention comprise administering the compound, in combination with an aromatase inhibitor. In another embodiment, the methods of the present invention comprise administering the compound, in combination with a progestin. In another embodiment, the methods of the present invention comprise administering the compound, in combination with an agent acting through other nuclear hormone receptors. In another embodiment, the methods of the present invention comprise administering the compound, in combination with a selective estrogen receptor modulators (SERM). In another embodiment, the methods of the present invention comprise administering the compound, in combination with a progesterone. In another embodiment, the methods of the present invention comprise administering the compound, in combination with an estrogen. In another embodiment, the methods of the present invention comprise administering the compound, in combination with a PDE5 inhibitor. In another embodiment, the methods of the present invention comprise administering the compound, in combination with apomorphine. In another embodiment, the methods of the present invention comprise administering the compound, in combination with a bisphosphonate. In another embodiment, the methods of the present invention comprise administering the compound, in combination with one or more additional SARMs. In some embodiments, the methods of the present invention comprise combined preparations comprising the compound and an agent as described hereinabove. In some embodiments, the combined preparations can be varied, e.g., in order to cope with the needs of a patient subpopulation to be treated or the needs of the single patient which different needs can be due to the particular disease, severity of the disease, age, sex, or body weight as can be readily determined by a person skilled in the art. In some embodiments, the methods of the present invention comprise personalized medicine methods which treat the needs of a single patient. In one embodiment, different needs can be due to the particular disease, severity of the disease, the overall medical state of a patient, or the age of the patient. In some embodiments, personalized medicine is the application of genomic data to better target the delivery of medical interventions. Methods of personalized medicine, in some embodiments, serve as a tool in the discovery and clinical testing of new products of the present invention. In one embodiment, personalized medicine involves the application of clinically useful diagnostic tools that may help determine a patient's predisposition to a particular disease or condition. In some embodiments, personalized medicine is a comprehensive approach utilizing molecular analysis of both patients and healthy individuals to guide decisions throughout all stages of the discovery and development of pharmaceuticals and diagnostics; and applying this knowledge in clinical practice for a more efficient delivery of accurate and quality healthcare through improved prevention, diagnosis, treatment, and monitoring methods.

It is to be understood that any use of any of the compounds as herein described may be used in the treatment of any disease, disorder or condition as described herein, and represents an embodiment of this invention.

The following examples are presented in order to more fully illustrate the preferred embodiments of the invention. They should in no way, however, be construed as limiting the broad scope of the invention.

EXAMPLES

Example 1

Synthesis of (S) Enantiomer of Compound of Formula II

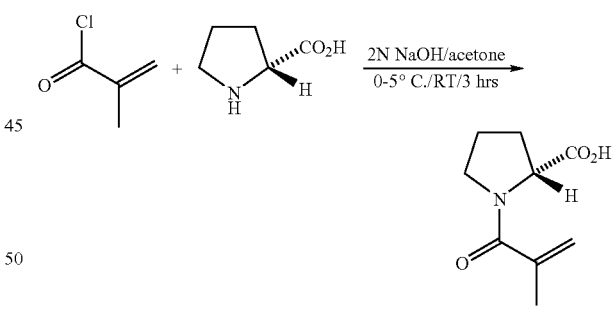

(2R)-1-Methacryloylpyrrolidin-2-carboxylic Acid. D-Proline, 14.93 g, 0.13 mol) was dissolved in 71 mL of 2 N NaOH and cooled in an ice bath; the resulting alkaline solution was diluted with acetone (71 mL). An acetone solution (71 mL) of metacryloly chloride (13.56 g, 0.13 mol) and 2N NaOH solution (71 mL) were simultaneously added over 40 min to the aqueous solution of D-proline in an ice bath. The pH of the mixture was kept at 10-11° C. during the addition of the metacryloly chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over Na$_2$SO$_4$, filtered through Celite, and evaporated in vacuo to give the crude product as a colorless oil. Recrystallization of the oil from ethyl ether and hexanes afforded 16.2 (68%) of the desired compound as colorless crystals: mp 102-103° C. (lit. [214] mp 102.5-103.5° C.); the NMR spectrum of this compound demonstrated the existence of two rotamers of the title compound. $^1$H NMR (300 MHz, DMSO-d$_6$) δ 5.28 (s) and 5.15 (s) for the first rotamer, 5.15 (s) and 5.03 (s) for the second rotamer (totally 2H for both rotamers, vinyl CH$_2$), 4.48-4.44 for the first rotamer, 4.24-4.20 (m) for the second rotamer (totally 1H for both rotamers, CH at the chiral canter), 3.57-3.38 (m, 2H, CH$_2$), 2.27-2.12 (1H, CH), 1.97-1.72 (m, 6H, CH$_2$, CH, Me); $^{13}$C NMR (75 MHz, DMSO-d$_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[\alpha]_D^{26}$+80.8° (c=1, MeOH); Anal. Calcd. for C$_9$H$_{13}$NO$_3$: C, 59.00; H, 7.15; N, 7.65. Found: C, 59.13; H, 7.19; N, 7.61.

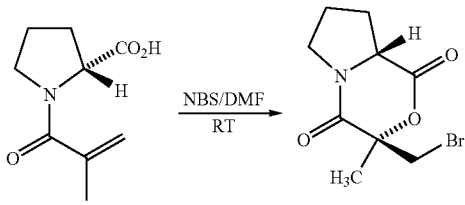

(3R,8aR)-3-Bromomethyl-3-methyl-tetrahydro-pyrrolo [2,1-c][1,4]oxazine-1,4-dione. A solution of NBS (23.5 g, 0.132 mol) in 100 mL of DMF was added dropwise to a stirred solution of the (methyl-acryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152-154° C. (lit. [214] mp 107-109° C. for the S-isomer); $^1$H NMR (300 MHz, DMSO-d$_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2H, Me); $^{13}$C NMR (75 MHz, DMSO-d$_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[\alpha]_D^{26}$+124.5° (c=1.3, chloroform); Anal. Calcd. for C$_9$H$_{12}$BrNO$_3$: C, 41.24; H, 4.61; N, 5.34. Found: C 41.46, H 4.64, N 5.32.

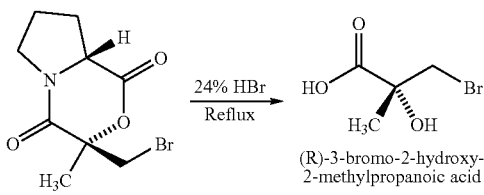

(2R)-3-Bromo-2-hydroxy-2-methylpropanoic Acid. A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite, and evaporated in vacuo to dryness. Recrystallization from toluene afforded 10.2 g (86%) of the desired compound as colorless crystals: mp 107-109° C. (lit. [214] mp 109-113° C. for the S-isomer); $^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[\alpha]_D^{26}$+10.5° (c=2.6, MeOH); Anal. Calcd. for C$_4$H$_7$BrO$_3$: C 26.25, H 3.86. Found: C 26.28, H 3.75.

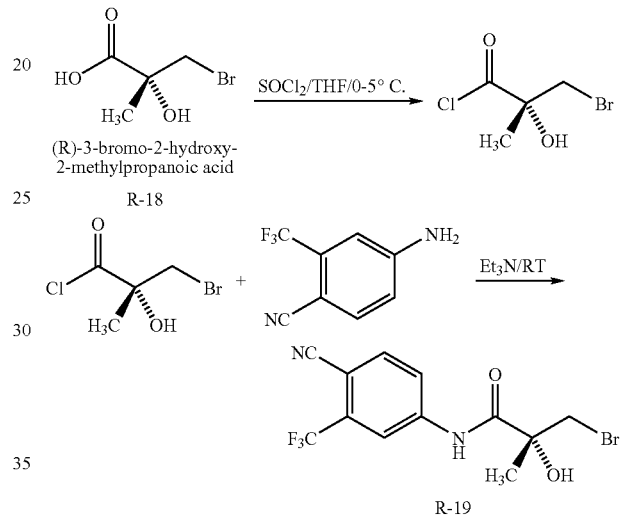

Synthesis of (2R)-3-Bromo-N-[4-cyano-3-(trifluoromethyl)phenyl]-2-hydroxy-2-methylpropanamide. Thionyl chloride (46.02 g, 0.39 mol) was added dropwise to a cooled solution (less than 4° C.) of R-18 (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid, which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-Bromo-N-[4-cyano-3-(trifluoromethyl)phenyl]-2-hydroxy-2-methylpropanamide (R-32a) as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M-H]$^-$ 349.0. M.p.: 124-126° C.,

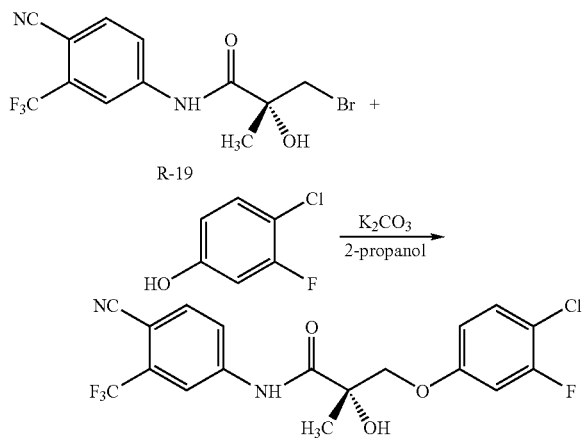

Synthesis of (S)-3-(4-chloro-3-fluorophenoxy)-N-(4-cyano-3-(trifluoromethyl)phenyl)-2-hydroxy-2-methylpropanamide. A mixture of bromoamide ((2R)-3-bromo-N-[4-cyano-3-(trifluoromethyl)phenyl]-2-hydroxy-2-methylpropanamide, (R-19) 2.0 g, 5.70 mmol), anhydrous $K_2CO_3$ (2.4 g, 17.1 mmol) was heated to reflux for 2 h and then concentrated under reduced pressure to give a solid. The resulting solid was treated with 4-chloro-3-fluorophenol (1.3 g, 8.5 mmol) and anhydrous $K_2CO_3$ (1.6 g, 11.4 mmol) in 50 mL of 2-propanol was heated to reflux for 3 h and then concentrated under reduced pressure to give a solid. The residue was treated with 100 mL of $H_2O$ and then extracted with EtOAc (2×100 mL). The combined EtOAc extracts were washed with 10% NaOH (4×100 mL) and brine, successively. The organic layer was dried over $MgSO_4$ and then concentrated under reduced pressure to give an oil which was purified by column chromatography using EtOAc/hexane (50:50) to give a solid which was recrystallized from $CH_2Cl_2$/hexane to give 1.7 g (70.5%) of (S)-3-(4-chloro-3-fluorophenoxy)-N-(4-cyano-3-(trifluoromethyl)phenyl)-2-hydroxy-2-methylpropanamide as a colorless solid.

$^1$H NMR ($CDCl_3$/TMS) δ 1.60 (s, 3H, $CH_3$), 3.28 (s, 1H, OH), 3.98 (d, J=9.05 Hz, 1H, CH), 6.64-6.76 (m, 2H, ArH), 7.30 (d, J=8.67 Hz, 1H, Arm), 7.81 (d, J=8.52 Hz, 1H, ArH), 7.96 (q, J=2.07, 8.52 Hz, 1H, ArH), 8.10 (d, J=2.07 Hz, 1H, ArH), 9.10 (s, 1H, NH). Calculated Mass: [M-H]-414.9. Mp: 132-134° C.

Example 2

Metabolic Stability of the Compounds of this Invention

Metabolic stability assays were performed in order to assess the in vitro half-life of compounds of formula II when incubated with human liver microsomes. The data generated was transformed to determine intrinsic clearance values. In a separate experiment, permeability across human, intestinal epithelial monolayers (Caco-2 cells) was used as a measure of intestinal permeability as well as an indicator of efflux potential. Caco-2 cells are often used as an early screening surrogate for oral bioavailability. Microsomal half-life can be converted to in vitro clearance values as a means to predict hepatic intrinsic clearance. Intrinsic clearance is defined as the functional ability of the liver to metabolize a drug or other compound.

Materials and Methods:

Metabolic Stability Measured in Human Liver Microsomes:

Compounds of formula II in this study were incubated at a final concentration of 0.6 μM. Microsome reactions were performed under either Phase I or "Phase I and II" conditions, where indicated. Compound stocks (10 mM ACN) were initially diluted to a concentration of 60 μM (in 60% ACN/$H_2O$) resulting in a "working stock" solution of 100×. Human liver microsomes were utilized at a final concentration of 0.6 mg/ml. Duplicate wells were used for each time point (0, 6, 10, 30, and 60 minutes). Reactions were carried out at 37° C. in a shaking water bath, and the final concentration of solvent was kept constant at 0.6%. The final volume for each reaction was 600 μl, comprised of 368 μl of 100 mM $KPO_4$ buffer, (pH 7.4); 12.6 μl of HLM (from a 20 mg/ml stock); 6 μl of 100×"working stock" drug compound, and 126 μl of NRS "master mix" solution. At each time point, 100 μl of reaction was removed and added to a sample well containing 100 μl of ice-cold, 100% ACN (plus internal standards), to stop the reaction. The NRS "master mix" is a solution of glucose 6-phosphate dehydrogenase, $NADP^+$, $MgCl_2$, and glucose 6-phosphate, prepared per manufacturer's instructions (BD Biosciences, Waltham, Mass.). Each 6.0 ml stock of NRS "master mix" solution contains 3.8 ml $H_2O$, 1.0 ml solution "A" (Cat. #461220), and 0.2 ml solution "B" (Cat. #461200). Human liver microsomes (lot #0610279, Xenotech Corp.) represented a pool of 60 donors.

Samples were centrifuged at 3,000 rpm for 10 minutes at 4° C. to remove debris and precipitated protein. Approximately 160 μl of supernatant was subsequently transferred to a new sample block for analysis. The concentration of parent drug remaining in each well (expressed as percent remaining versus Time '0', at the beginning of the reaction) was measured by LC/MS, as detailed below. The intrinsic clearance rates (CLint) were calculated from 0-60 minutes based on first order decay kinetics as a function of microsomal protein concentration.

Permeability across Human, Intestinal Epithelial Monolayers:

Permeability was measured in the Apical (pH 6.6) to Basolateral (pH 7.4) and Basolateral (pH 7.4) to Apical (pH 6.6) directions across polarized, Caco-2 epithelial monolayers. Compound stocks (10 mM acetonitrile) were tested in the study at a final concentration of 10 μM. The concentration of drug in the receiver well was measured by LC/MS/MS using a standard curve. The apparent permeability (Papp) for each compound was calculated, and values (A-B) were classified as:

Poor (Papp: <1), Low (Papp 1-2), Medium (Papp 2-10) or High (Papp>10).

Papp(×$10^{-6}$ cm/sec)=Amount transported/ (Area*Initial concentration*Time)

Papp(cm/s)=[$V/(A*Ci)$]*($Cf/T$)

V=volume of the receptor chamber (ml, or $cm^3$)
A=area of the membrane insert ($cm^2$)
Ci=initial concentration of drug (μM)
Cf=final concentration of drug (μM)
T=assay time (seconds)

Analytical Methods:

All samples were analyzed on the MDS/Sciex API4000 Q Trap system with electrospray ionization (ESI) in the positive or negative SIM mode, depending on the compounds. The mobile phases were isocratic at 30% A (0.1% formic acid in water) and 70% B (0.1% formic acid in acetonitrile) with a flow rate of 0.4 m/min. A Phenomenex Luna Phenyl-Hexyl column (60×2.0 mm ID, 6µ) was used. The injection volume was 10 µL. The total run time per sample was 1.6 to 3.0 minutes. Tamoxifen and diclofenac were used as internal standards for the positive and negative mode, respectively. The percentage of parent drug compound remaining after each time point was determined relative to the initial measured concentration at the beginning of the reaction ($T_0$ min).

Data Analysis:

For half-life determination, data was fitted using GraphPad Prism, v 4.03 with the non-linear regression equation "one phase exponential decay" defined as:

$$Y=Span*exp(-K*X)+Plateau \text{ (decays to Plateau with a first-order rate constant, } K).$$

"-K" is the slope of the curve. The half life (minutes), $T_{1/2}$, =ln 0.6/−K and is therefore defined as −0.693/−K, or 0.693/K, a/k/a −0.693/slope). Intrinsic Clearance (µl/min/mg protein) is defined as: CLint=0.693*(1/$T_{1/2}$)*(ml incubation/mg protein)*1000; This equation can also be expressed as (K*1000)/microsome conc.

Results:

TABLE 1

Metabolic Stability Measured in Human Liver Microsomes:

| Compound having formula | Half Life (minutes) Phase I only | $CL_{int}$ (ul/min/mg) Phase I only | Half Life (minutes) Phase I + II | $CL_{int}$ (ul/min/mg) Phase I + II |
|---|---|---|---|---|
| II | Stable | <1 | Stable | <1 |

The results had shown that in vitro half-life as determined from the microsomal assays demonstrated that compound of formula (II) under both phase I and phase I/II metabolic conditions. As shown in Table 1, the compound didn't exhibit an intrinsic clearance (CLint) value greater than 10 µl/min/mg. It is generally accepted that an in vitro CLint value of less than 10 µl/min/mg protein represents favorable metabolic stability of the test compound. Compound of formula II exhibited low clearance in human liver microsomes. In conclusion, based on the data reported herein, compound of formula (II) exhibited favorable metabolic stability profiles in vivo studies.

Example 3

Androgen Receptor Binding Affinity of SARMs

Materials and Methods:

The androgen receptor (AR) binding affinity of SARMs was determined by using an in vitro competitive radioligand binding assay with [17α-methyl-$^3$H]-Mibolerone ([$^3$H]MIB, PerkinElmer), a high affinity AR ligand. Recombinant androgen receptor ligand binding domain (AR LBD) was combined with [$^3$H]MIB in buffer A (10 mM Tris, pH 7.4, 1.6 mM disodium EDTA, 0.26 M sucrose, 10 mM sodium molybdate, 1 mM PMSF) to determine the equilibrium dissociation constant ($K_d$) of [$^3$H]MIB. Protein was incubated with increasing concentrations of [$^3$H]MIB with and without a high concentration of unlabeled MIB in order to determine total and non-specific binding. Non-specific binding was then subtracted from total binding to determine specific binding and graphed using SigmaPlot and non-linear regression for ligand binding curve with one site saturation to determine the $K_d$ of MIB (1.84 nM). In addition, the concentration of [$^3$H]MIB required to saturate AR LBD was determined to be 4 nM.

Compound of formula (II) was tested in a range of concentrations from $10^{-11}$ to $10^{-6}$ M using the conditions described above. Following incubation, plates were harvested with GF/B filters on the Unifilter-96 Harvester (PerkinElmer) and washed three times with ice-cold buffer B (60 mM Tris, pH 7.2). The filter plates were dried at RT, then 36 µl Microscint-O cocktail was added to each well and sealed with TopSeal-A. The receptor bound radioligand was then determined with the TopCount® NXT Microplate Scintillation Counter (PerkinElmer).

The specific binding of [$^3$H]MIB at each concentration of SARM was determined by subtracting the nonspecific binding of [$^3$H]MIB (determined by incubating with $10^{-6}$ M unlabeled MIB), and expressed as a percentage of the specific binding in the absence of each SARM. The concentration of SARM required to decrease the [$^3$H]MIB binding by 60%, $IC_{60}$ value, was determined by computer-fitting the data with SigmaPlot and non-linear regression with the standard curve four parameter logistic curve. The equilibrium binding constant ($K_i$) of each compound was then determined with the following equation:

$$K_i = K_d \times IC_{60}/(K_d+L)$$

where $K_d$ is the equilibrium dissociation constant of [$^3$H]MIB (1.84 nM), and L is the concentration of [$^3$H]MIB (4 nM).

Results:

The binding affinity for compound of formula (II) was tested in the radioligand binding assay with AR LBD as the receptor with $K_i$ (nM)=8.1

Example 4

Preclinical Anabolic and Androgenic Pharmacology of Compound (II) in Intact and Castrate Male Rats Anabolic and androgenic efficacy of Compound (II) administered by daily oral gavage were tested. The S-isomer of Compound (II) was synthesized and tested as described herein Materials and Methods:

Male Sprague-Dawley rats weighing approximately 200 g were purchased from Harlan Bioproducts for Science (Indianapolis, Ind.). The animals were maintained on a 12-h light/dark cycle with food (7012C LM-485 Mouse/Rat Sterilizable Diet, Harlan Teklad, Madison, Wis.) and water available ad libitum. The animal protocol was reviewed and approved by the Institutional Animal Care and Use Committee of the University of Tennessee. The anabolic and androgenic activity of Compound (II) in intact animals, acutely orchidectomized (ORX) animals and chronically (9 days) ORX rats.

The test article for this study was weighed and dissolved in 10% DMSO (Fisher) diluted with PEG 300 (Acros Organics, NJ) for preparation of the appropriate dosage concentrations. The animals were housed in groups of 2 to 3 animals per cage. Animals were randomly assigned to one of seven groups consisting of 4 to 5 animals per group. Control groups (intact and ORX) were administered vehicle daily. Compound (II) was administered via oral gavage at doses of 0.01, 0.03, 0.1, 0.3, 0.75, and 1 mg/day to both intact and ORX groups. Where appropriate, animals were castrated on day one of the study. Treatment with Compound (II) began nine days post ORX and was administered daily via oral gavage for fourteen days.

The animals were sacrificed under anesthesia (ketamine/xyalzine, 87:13 mg/kg) and body weights were recorded. In addition, ventral prostate, seminal vesicles, and levator ani muscle were removed, individually weighed, normalized to body weight, and expressed as a percentage of intact control. Student's T-test was used to compare individual dose groups to the intact control group. Significance was defined a priori as a P-value <0.05. Ventral prostate and seminal vesicle weights were evaluated as a measure of androgenic activity, whereas levator ani muscle weight was evaluated as a measure of anabolic activity. Blood was collected from the abdominal aorta, centrifuged, and sera were frozen at −80° C. prior to determination of serum hormone levels. Serum luteinizing hormone (LH) and follicle stimulating hormone (FSH) concentrations were determined.

Results:

A series of dose-response studies in intact and castrated rats in order to evaluate the potency and efficacy of Compound (II) in both androgenic (prostate and seminal vesicles) and anabolic (levator ani muscle) tissue was conducted. In intact animals, Compound (II) treatment resulted in decreases in the weight of both prostate and seminal vesicles while the levator ani muscle weight was significantly increased. Levator ani muscle weight following Compound II treatment were 100%±10%, 98%±7%, 110%±5%, 110%±5%, 125%±10%, and 129%±10% of intact controls following doses of 0.01, 0.03, 0.1, 0.3, 0.75, and 1 mg/day, respectively. The prostate weights were 117%±20%, 98%±15%, 82%±20%, 62%±5%, 107%±30%, and 110%±14% of intact controls following doses of 0.01, 0.03, 0.1, 0.3, 0.75, and 1 mg/day, respectively. These results are significant since current androgen therapies are contraindicated in some patient populations due to the proliferative androgenic effects in prostate and breast tissues. However, many patients in these populations could benefit from the anabolic actions of androgens in muscle and bone. Since Compound (II) exhibited tissue selective anabolic effects, it may be possible to treat patient groups in which androgens were contraindicated in the past.

Figure 2:
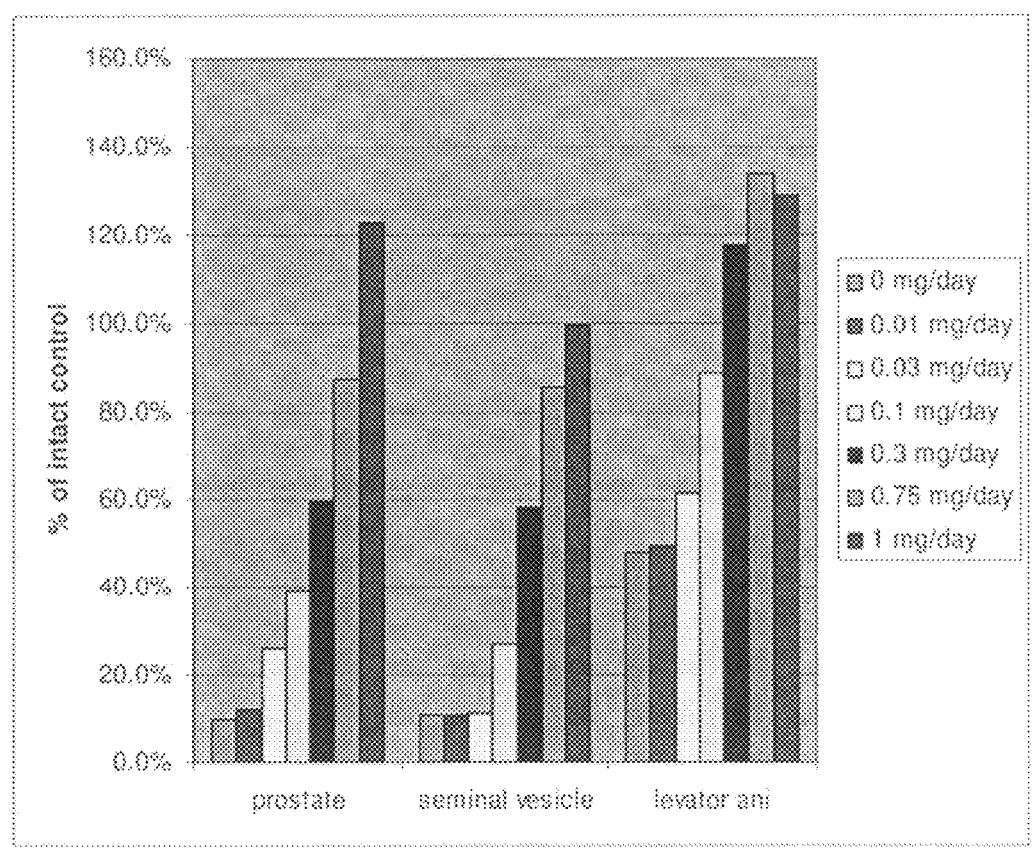
FIG. 2: Anabolic and androgenic pharmacology of Compound II.

In castrated, ORX animals, prostate weights following Compound II treatment were 10%±3%, 12%±3%, 26%±7%, 39%±6%, 60%±14%, 88%±16%, and 123%±22% of intact controls following doses of 0, 0.01, 0.03, 0.1, 0.3, 0.75, and 1 mg/day, respectively (FIG. 2). Similarly, seminal vesicle weights were 11%±1%, 11%±1%, 11%±1%, 27%±14%, 58%±18%, 86%±12%, and 100%±8% of intact controls following doses of 0, 0.01, 0.03, 0.1, 0.3, 0.75, and 1 mg/day, respectively (FIG. 2). Significant increases were seen in levator ani muscle weights of in all dose groups, when compared to intact controls. The levator ani muscle weights were 48%±8%, 50%±5%, 62%±6%, 89%±10%, 118%±6%, 134%±8% and 129%±14% of intact controls corresponding to 0, 0.01, 0.03, 0.1, 0.3, 0.75, and 1.0 mg/day dose groups, respectively (FIG. 2).

Testosterone propionate (TP) and S-3-(4-Acetylaminophenoxy)-2-hydroxy-2-methyl-N-(4-nitro-3-trifluoromethylphenyl) propionamide (S-4), maximally stimulated the levator ani muscle weight to 104% and 101%, respectively. These data show that Compound (II) exhibited significantly greater efficacy and potency than either TP or S-4. As a whole, these data show that Compound II is able to stimulate muscle growth in the presence or absence of testosterone while exerting anti-proliferative effects on the prostate. These data show that Compound (II) restore lost muscle mass in patients with sarcopenia or cachexia. Additionally, the antiproliferative effects of Compound (II) on the prostate may allow some patient populations, in which androgens are currently contraindicated, access to anabolic agents.

Compound II exhibited anabolic muscle/prostate ratio in castrated rats of 4.10, 2.39, 2.28, 1.97, 1.53, 1.05 following doses of 0.01, 0.03, 0.1, 0.3, 0.75 and 1 mg/day, respectively.

Pharmacology results following 1 mg/day of compound II exhibited that prostate weight was 110%±14% of intact control and levator ani muscle weight was 129%±10% of intact control. Compound II maintained prostate weight following orchidectomy at 123±22% of intact controls and levator ani muscle weight at 129±14% of intact controls. A range of between 0.1 mg/day to 0.3 mg/day of Compound II restored 100% of levator ani muscle weight, while between 39 to 60% prostate weight was restored.

Example 5

In Vitro CYP Inhibition Assay

Materials and Methods:

P450 enzyme inhibition was measured using human cDNA-expressed CYP3A4, 2D6, 2C19, 2C9, and 1A2 recombinant enzymes and fluorogenic substrates (coumarin analogues) that are converted to fluorescent products. The analogues utilized for each isoenzyme are as follows: 7-Benzyloxy-trifluoromethylcoumarin, (BFC) for 3A4; 3-[2-(N,N-diethyl-N-methyl amino)ethyl] 7-methoxy-4-methylcoumarin, (AMMC) for 2D6; 3-Cyano-7-Ethoxycoumarin, (CEC) for 2C19 and 1A2; and 7-Methoxy-4-trifluoro-methylcoumarin, (MFC) for 2C9. These substrates were utilized at a single concentration (either 50 μM or 75 μM) at or near the apparent Km for each substrate. Fluorescence intensity was measured using a Wallac 1420 Victor$^3$ Multi-label Counter Model (Perkin-Elmer, Wellesley, Mass.), with an excitation wavelength filter of 405 nm, and an emission filter of 460 nm (535 nm for the 3A4 and 2C9 substrates). Compound stocks (10 mM in a 4:1 ratio of acetonitrile: DMSO) were tested in this study using an 8-point dose response curve in duplicate (ranging from 0.15 μM-20.0 μM). The concentration of acetonitrile was kept constant at 0.4%, and the reaction was carried out at 37° C. for 30 minutes. Averages (minus background) and $IC_{50}$ values were calculated.

Results:

The in-vitro screening results for potential drug-drug interactions (DD1) of SARM compound of formula II is presented in Table 2:

TABLE 2

| | CYP (P450) Inhibition, IC50 (μM) | | | | |
|---|---|---|---|---|---|
| Compound | 3A4 | 2D6 | 2C19 | 2C9 | 1A2 |
| II | >20 | 17.7 | 2.4 | 1.3 | >20 |

Example 6

Pharmacokinetics of Compound (II) in Dogs

In order to determine the pharmacokinetics of Compound II, the compound was administered to beagle dogs perorally, and circulating plasma levels, terminal elimination half-life (t½), total body clearance (CL), terminal volume distribution (Vz) and absolute bioavailability (F %) (Table 3) were determined. Compound I was rapidly and completely.

TABLE 3

|  | Compound II |
|---|---|
| T½ (hr) | 37 ± 26.8 |
| CL (mL/min/kg) | 0.36 ± 0.12 |
| Vz (mL/kg) | 1266 ± 352 |
| F % | 72.5% |

Example 7

Figure 3:
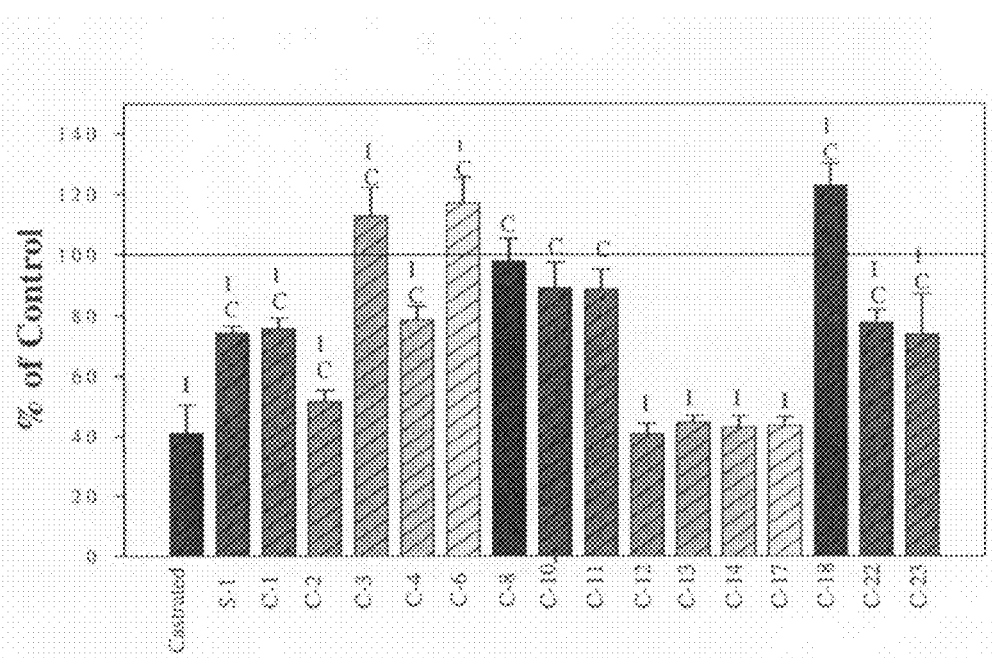
FIG. 3: Levator ani weight in castrated rats.
Figure 4:
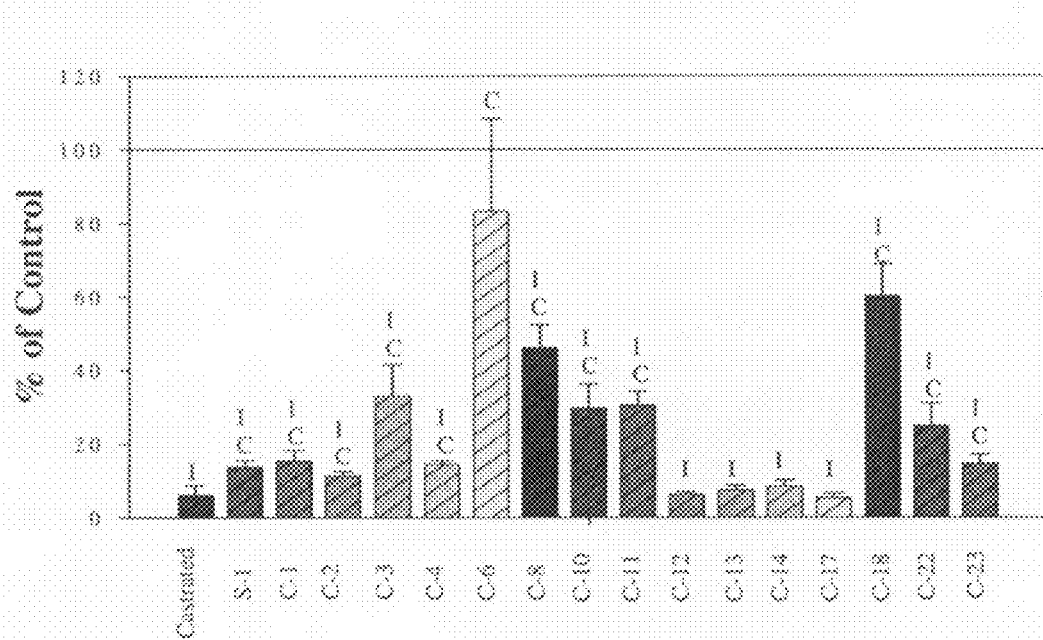
FIG. 4: Prostate weight in castrated rats.

Anabolic and Androgenic Activity of SARM Compounds in Intact and Castrated Male Rats The in vivo pharmacological activity of each synthetic AR ligand (listed in Table 4, below) was examined in five male Sprague-Dawley rats weighing approximately 200 g. Animals were castrated via a scrotal incision under anesthesia 24 h before drug treatments and received daily sc injections of the compound of interest at a dose rate of 1 mg/d for 14 d. All compounds of interest were freshly dissolved in vehicle containing dimethylsulfoxide (5%, vol/vol) in polyethylene glycol 300 before dose administration. An additional two groups of animals with or without castration received vehicle only and served as castrated or intact control groups, respectively. Animals were killed at the end of the treatment. Plasma samples were collected and stored at −80 C for future use. The ventral prostate, seminal vesicles, and levator ani muscle were removed, cleared of extraneous tissue, and weighed. All organ weights were normalized to body weight and compared. The weights of prostate and seminal vesicles were used to evaluate androgenic activity, whereas the levator ani muscle weight was used as a measure of anabolic activity. The results are summarized in FIGS. 2 and 3.

TABLE 4

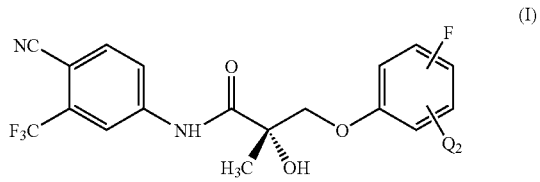

| Compound | $R_1$ | $R_2$ | $R_3$ | $R_4$ | $R_5$ |
|---|---|---|---|---|---|
| S-1 | H | H | F | H | H |
| C-1 | F | H | F | H | H |
| C-2 | $CH_3$ | H | F | H | H |
| C-3 | H | F | F | H | H |
| C-4 | H | Cl | F | H | H |
| C-6 | H | F | Cl | H | H |
| C-8 | F | H | Cl | H | H |
| C-10 | H | Cl | Cl | H | H |
| C-11 | H | F | $NO_2$ | H | H |
| C-12 | F | H | $NO_2$ | H | H |
| C-13 | F | F | F | H | H |
| C-14 | F | F | H | F | H |
| C-17 | F | H | F | H | F |
| C-18 | F | H | F | F | H |
| C-22 | Cl | H | Cl | Cl | H |
| C-23 | F | F | F | F | F |

It will be appreciated by a person skilled in the art that the present invention is not limited by what has been particularly shown and described hereinabove. Rather, the scope of the invention is defined by the claims that follow:

What is claimed is:

1. A compound represented by the structure of formula (I):

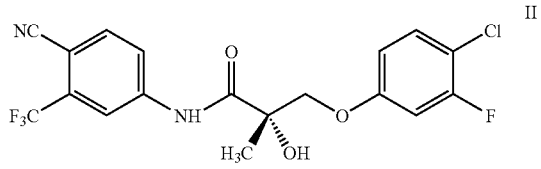

wherein $Q_2$ is alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; and R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

or its isomer, pharmaceutically acceptable salt or any combination thereof.

2. The compound of claim 1, wherein said compound is represented by the structure of formula II:

or its isomer, or pharmaceutically acceptable salt, or any combination thereof.

3. A composition comprising a compound of claim 1, and a pharmaceutically acceptable carrier, diluent, salt or a combination thereof.

4. A method of hormone therapy comprising the step of contacting an androgen receptor of a subject with a compound of claim 1 or its isomer, pharmaceutically acceptable salt or any combination thereof, in an amount effective to effect a change in an androgen-dependent condition.

5. A method of treating a subject wherein said subject suffers from osteoporosis, osteopenia, increased bone resorption, bone fracture, bone frailty, loss of bone mineral density (BMD), or any combination thereof, comprising the step of administering to said subject a compound of claim 1, or its isomer, pharmaceutically acceptable salt or any combination thereof, in an amount effective to treat osteoporosis, increase bone resorption, bone fracture, bone frailty, or loss of bone mineral density (BMD) in said subject.

6. A method of treating, reducing the incidence of, delaying progression of, reducing the severity of, or alleviating symptoms associated with a muscle wasting disorder in a subject, comprising the step of administering to said subject a compound of claim 1 or its isomer, pharmaceutically acceptable salt or any combination thereof, in an amount effective to treat said muscle wasting disorder in said subject.

7. The method of claim 6, wherein said muscle wasting disorder is due to a pathology, illness, disease or condition.

\* \* \* \* \*

UNITED STATES PATENT AND TRADEMARK OFFICE
CERTIFICATE OF CORRECTION

PATENT NO. : 7,772,433 B2  Page 1 of 4
APPLICATION NO. : 11/785250
DATED : April 16, 2007
INVENTOR(S) : James T. Dalton et al.

It is certified that error appears in the above-identified patent and that said Letters Patent is hereby corrected as shown below:

In Figure 1A the title should be:

--I. Synthetic Scheme for (*S*)–II Compound:--

And not

--I. Synthetic Scheme for (*S*)–[[III]] II Compound:--

In Figure 1B the title should be:

--II. Synthetic Scheme for (*R*)–II Compound:--

And not

--II. Synthetic Scheme for (*R*)–[[III]] II Compound:--

In Figure 1C the title should be:

--III. Synthetic Scheme for (*S*)–II (oxirane intermediate) Compound:--

And not

--III. Synthetic Scheme for (*S*)–[[III]] II (oxirane intermediate) Compound:--

In Figure 1D the title should be:

--IV. Synthetic Scheme for (*R*)–II (oxirane intermediate) Compound:--

And not

--IV. Synthetic Scheme for (*R*)–[[III]] II (oxirane intermediate) Compound:--

Signed and Sealed this

Seventh Day of December, 2010

David J. Kappos
*Director of the United States Patent and Trademark Office*

In Figure 1E the title should be:

--V. Synthetic Scheme for (*S*)–II involving B-ring addition prior to A-ring addition:--

And not

--V. Synthetic Scheme for (*S*)–[[III]] II involving B-ring addition prior to A-ring addition:--

In Figure 1F the title should be:

--VI. Synthetic Scheme of (*R*)–II involving B-ring addition prior to A-ring addition:--

And not

--VI. Synthetic Scheme of (*R*)–[[III]] II involving B-ring addition prior to A-ring addition:--

In Figure 1G the title should be:

--VII. Synthetic Scheme of (*S*)–II Using Chiral Intermediate and Involving B-ring Addition prior to A-ring Addition:--

And not

--VII. Synthetic Scheme of (*S*)–[[III]] II Using Chiral Intermediate and Involving B-ring Addition prior to A-ring Addition:--

In Figure 1H the title should be:

--VIII. Synthetic Scheme for (*R*)–II Using Chiral Intermediate and Involving B-ring Addition prior to A-ring Addition:--

And not

--VIII. Synthetic Scheme for (*R*)–[[III]] II Using Chiral Intermediate and Involving B-ring Addition prior to A-ring Addition:--

In Figure 1I the title should be:

--IX. Synthetic Scheme for Racemic Compound II Involving Oxazolidinedione Intermediate:--

And not

--IX. Synthetic Scheme for Racemic Compound [[III]] II Involving Oxazolidinedione Intermediate:--

In Figure 1J the title should be:

--X. Racemic Synthetic Scheme for Compound II:--

And not

--X. Racemic Synthetic Scheme for Compound [[III]] II:--

CERTIFICATE OF CORRECTION (continued)

In Figure 1K the title should be:

--XI. Large-scale Synthetic Scheme for (*S*)- II:--

And not

--XI. Large-scale Synthetic Scheme for (*S*)- [[III]] II:--

In Figure 1L the title should be:

--XII. Large-scale Synthetic Scheme for (*SR*)- II:--

And not

--XII. Large-scale Synthetic Scheme for (*S*)- [[III]] II:--

In column 135, lines 40-45 the represented structure should be:

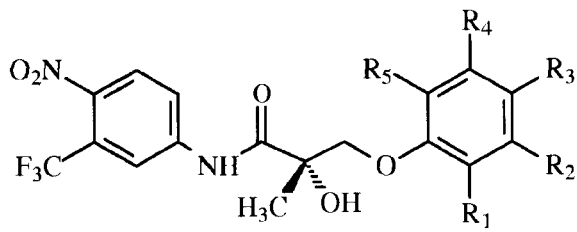

And not

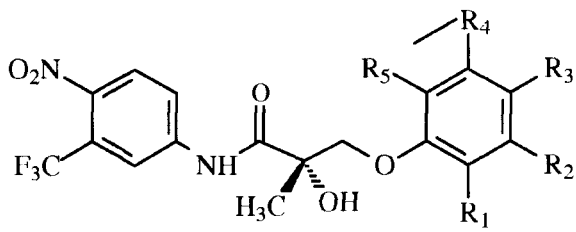

In column 136, lines 47-55:

Claim 5 should read:

--5. A method of treating a subject wherein said subject suffers from osteoporosis, osteopenia, increased bone resorption, bone fracture, bone frailty, loss of bone mineral density (BMD), or any combination thereof, comprising the step of administering to said subject a compound of claim 1, or its isomer, pharmaceutically acceptable salt or any combination thereof, in an amount effective to treat osteoporosis, increased bone resorption, bone fracture, bone frailty, or loss of bone mineral density (BMD) in said subject.--

And not

--5. A method of treating a subject wherein said subject suffers from osteoporosis, osteopenia, increased bone resorption, bone fracture, bone frailty, loss of bone mineral density (BMD), or any combination thereof, comprising the step of administering to said subject a compound of claim 1, or its isomer, pharmaceutically acceptable salt or any combination thereof, in an amount effective to treat osteoporosis, increase bone resorption, bone fracture, bone frailty, or loss of bone mineral density (BMD) in said subject.--